(12) United States Patent
Kishimoto

(10) Patent No.: US 10,071,114 B2
(45) Date of Patent: *Sep. 11, 2018

(54) METHODS AND COMPOSITIONS FOR ATTENUATING GENE EXPRESSION MODULATING ANTI-VIRAL TRANSFER VECTOR IMMUNE RESPONSES

(71) Applicant: Selecta Biosciences, Inc., Watertown, MA (US)

(72) Inventor: Takashi Kei Kishimoto, Lexington, MA (US)

(73) Assignee: Selecta Biosciences, Inc., Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/846,964

(22) Filed: Sep. 7, 2015

(65) Prior Publication Data

US 2016/0074427 A1 Mar. 17, 2016

Related U.S. Application Data

(60) Provisional application No. 62/101,841, filed on Jan. 9, 2015, provisional application No. 62/101,861, filed on Jan. 9, 2015, provisional application No. 62/101,872, filed on Jan. 9, 2015, provisional application No. 62/101,882, filed on Jan. 9, 2015, provisional application No. 62/051,255, filed on Sep. 16, 2014, provisional application No. 62/051,258, filed on Sep. 16, 2014, provisional application No. 62/051,263, filed on Sep. 16, 2014, provisional application No. 62/051,267, filed on Sep. 16, 2014, provisional application No. 62/047,034, filed on Sep. 7, 2014, provisional application No. 62/047,044, filed on Sep. 7, 2014, provisional application No. 62/047,054, filed on Sep. 7, 2014, provisional application No. 62/047,051, filed on Sep. 7, 2014.

(51) Int. Cl.
| | | |
|---|---|---|
| *A61K 35/00* | (2006.01) | |
| *A61K 31/7088* | (2006.01) | |
| *A61K 31/439* | (2006.01) | |
| *A61K 31/00* | (2006.01) | |

(52) U.S. Cl.
CPC .......... *A61K 31/7088* (2013.01); *A61K 31/00* (2013.01); *A61K 31/439* (2013.01)

(58) Field of Classification Search
None
See application file for complete search history.

(56) References Cited

U.S. PATENT DOCUMENTS

| | | |
|---|---|---|
| 5,100,669 A | 3/1992 | Hyon et al. |
| 5,543,158 A | 8/1996 | Gref et al. |
| 5,679,347 A | 10/1997 | Porcelli et al. |
| 5,762,904 A | 6/1998 | Okada et al. |
| 5,912,017 A | 6/1999 | Mathiowitz et al. |
| 6,060,082 A | 5/2000 | Chen et al. |
| 6,197,229 B1 | 3/2001 | Ando et al. |
| 6,251,957 B1 | 6/2001 | Wilson |
| 6,306,640 B1 | 10/2001 | Nicolette |
| 6,387,397 B1 | 5/2002 | Chen et al. |
| 6,838,089 B1 | 1/2005 | Carlsson et al. |
| 7,045,508 B2 | 5/2006 | Scaria |
| 8,629,151 B2 | 1/2014 | Zepp et al. |
| 8,652,487 B2 | 2/2014 | Maldonado et al. |
| 8,865,487 B2 | 10/2014 | Kostka et al. |
| 9,005,665 B2 | 4/2015 | Gourapura |
| 9,006,254 B2 | 4/2015 | Zepp et al. |
| 9,017,697 B2 | 4/2015 | Thomas |
| 9,066,978 B2 | 6/2015 | Ilyinskii et al. |
| 9,265,815 B2 | 2/2016 | Fraser et al. |
| 9,289,476 B2 | 3/2016 | Fraser et al. |
| 9,289,477 B2 | 3/2016 | Fraser et al. |
| 9,295,718 B2 | 3/2016 | Fraser et al. |
| 9,764,031 B2 | 9/2017 | Ilyinskii et al. |
| 9,884,112 B2 | 2/2018 | Zepp et al. |
| 2002/0014242 A1 | 2/2002 | Scaria et al. |
| 2002/0019361 A1 | 2/2002 | Scaria |
| 2002/0086049 A1 | 7/2002 | Bolton et al. |
| 2002/0095135 A1 | 7/2002 | Meeker |
| 2004/0038406 A1 | 2/2004 | Unger et al. |
| 2004/0043483 A1 | 3/2004 | Qian et al. |
| 2006/0002852 A1 | 1/2006 | Saltzman et al. |
| 2006/0002971 A1 | 1/2006 | Saltzman et al. |
| 2006/0147432 A1 | 7/2006 | Moore et al. |
| 2006/0210638 A1 | 9/2006 | Liversidge et al. |
| 2006/0222652 A1 | 10/2006 | Sebbel et al. |
| 2006/0251677 A1 | 11/2006 | Bachmann et al. |
| 2006/0251710 A1 | 11/2006 | Kwon et al. |

(Continued)

FOREIGN PATENT DOCUMENTS

| | | |
|---|---|---|
| CA | 2815422 A1 | 4/2012 |
| CN | 101437491 A | 5/2009 |
| CN | 101646418 A | 2/2010 |
| CN | 101703781 A | 5/2010 |
| CN | 101861165 A | 10/2010 |
| EP | 0759941 B1 | 9/2000 |
| EP | 1 932 538 A1 | 6/2008 |
| EP | 2073848 A2 | 7/2009 |
| EP | 2345412 A1 | 7/2011 |
| EP | 2522338 A2 | 11/2012 |
| JP | H01-502909 A | 10/1989 |
| JP | 2006-257095 | 9/2006 |

(Continued)

OTHER PUBLICATIONS

U.S. Appl. No. 12/788,260, filed May 26, 2010, Zepp et al.

(Continued)

*Primary Examiner* — James S Ketter
(74) *Attorney, Agent, or Firm* — Wolf, Greenfield & Sacks, P.C.

(57) ABSTRACT

Provided herein are methods and related compositions for administering viral transfer vectors and antigen-presenting cell targeted immunosuppressants.

14 Claims, 10 Drawing Sheets

Specification includes a Sequence Listing.

(56) References Cited

U.S. PATENT DOCUMENTS

| | | |
|---|---|---|
| 2006/0251711 A1 | 11/2006 | Konduri et al. |
| 2006/0269540 A1 | 11/2006 | Robert et al. |
| 2007/0110685 A1 | 5/2007 | Auspitz et al. |
| 2007/0254897 A1 | 11/2007 | Gjorstrup |
| 2008/0031899 A1 | 2/2008 | Reddy et al. |
| 2008/0145441 A1 | 6/2008 | Penades et al. |
| 2008/0160089 A1 | 7/2008 | Vitiello et al. |
| 2008/0254045 A1 | 10/2008 | Donda et al. |
| 2008/0311140 A1 | 12/2008 | Lee et al. |
| 2009/0004259 A1 | 1/2009 | Rabinovich et al. |
| 2009/0028910 A1 | 1/2009 | DeSimone et al. |
| 2009/0074828 A1 | 3/2009 | Alexis et al. |
| 2009/0082260 A1 | 3/2009 | Lamb et al. |
| 2009/0155292 A1 | 6/2009 | Santamaria et al. |
| 2009/0226525 A1 | 9/2009 | de los Rios et al. |
| 2010/0008932 A1 | 1/2010 | Bensussan et al. |
| 2010/0055076 A1 | 3/2010 | Lim et al. |
| 2010/0055189 A1 | 3/2010 | Hubbell et al. |
| 2010/0062968 A1 | 3/2010 | Pulendran et al. |
| 2010/0068261 A1 | 3/2010 | Tamarkin et al. |
| 2010/0068286 A1 | 3/2010 | Troiano et al. |
| 2010/0080816 A1 | 4/2010 | Hadeiba et al. |
| 2010/0112077 A1 | 5/2010 | Desai et al. |
| 2010/0129392 A1 | 5/2010 | Shi et al. |
| 2010/0129439 A1 | 5/2010 | Alexis et al. |
| 2010/0151000 A1 | 6/2010 | Thomas et al. |
| 2010/0172994 A1 | 7/2010 | Sigmund et al. |
| 2010/0183602 A1 | 7/2010 | Carballido Herrera et al. |
| 2010/0183727 A1 | 7/2010 | Iannacone et al. |
| 2010/0196401 A1 | 8/2010 | Scaria |
| 2010/0233197 A1 | 9/2010 | Wakatsuki Pedersen et al. |
| 2010/0233251 A1 | 9/2010 | Von Andrian et al. |
| 2010/0273220 A1 | 10/2010 | Yanik et al. |
| 2010/0303850 A1 | 12/2010 | Lipford et al. |
| 2011/0004148 A1 | 1/2011 | Ishii et al. |
| 2011/0020388 A1 | 1/2011 | Zepp et al. |
| 2011/0027217 A1 | 2/2011 | Zepp et al. |
| 2011/0070153 A1 | 3/2011 | Hyde et al. |
| 2011/0070154 A1 | 3/2011 | Hyde et al. |
| 2011/0076273 A1 | 3/2011 | Adler et al. |
| 2011/0110965 A1 | 5/2011 | Fraser et al. |
| 2011/0171248 A1 | 7/2011 | Pittet et al. |
| 2011/0223201 A1 | 9/2011 | Lipford et al. |
| 2011/0262491 A1 | 10/2011 | Keegan et al. |
| 2011/0272836 A1 | 11/2011 | Keegan et al. |
| 2011/0293700 A1 | 12/2011 | Bratzler et al. |
| 2011/0293701 A1 | 12/2011 | Bratzler et al. |
| 2011/0293723 A1 | 12/2011 | Bratzler et al. |
| 2012/0014966 A1 | 1/2012 | Solinger et al. |
| 2012/0027806 A1 | 2/2012 | Ilyinskii et al. |
| 2012/0027808 A1 | 2/2012 | Iannacone et al. |
| 2012/0058153 A1 | 3/2012 | Ilyinskii et al. |
| 2012/0058154 A1 | 3/2012 | Ilyinskii et al. |
| 2012/0064110 A1 | 3/2012 | Ilyinskii et al. |
| 2012/0070493 A1 | 3/2012 | Fraser et al. |
| 2012/0077860 A1 | 3/2012 | Garcia |
| 2012/0114677 A1 | 5/2012 | Zepp et al. |
| 2012/0171229 A1 | 7/2012 | Zepp et al. |
| 2012/0244222 A1 | 9/2012 | Altreuter et al. |
| 2012/0276109 A1 | 11/2012 | Fraser et al. |
| 2012/0276133 A1 | 11/2012 | Maldonado et al. |
| 2012/0276134 A1 | 11/2012 | Fraser et al. |
| 2012/0276155 A1 | 11/2012 | Kishimoto et al. |
| 2012/0276156 A1 | 11/2012 | Fraser et al. |
| 2012/0276157 A1 | 11/2012 | Fraser et al. |
| 2012/0276158 A1 | 11/2012 | Fraser et al. |
| 2012/0276159 A1 | 11/2012 | Fraser et al. |
| 2012/0276160 A1 | 11/2012 | Maldonado et al. |
| 2012/0294888 A1 | 11/2012 | Kishimoto et al. |
| 2012/0301498 A1 | 11/2012 | Altreuter et al. |
| 2012/0301510 A1 | 11/2012 | Kishimoto et al. |
| 2012/0308563 A1 | 12/2012 | Arya et al. |
| 2013/0028857 A1 | 1/2013 | Gao et al. |
| 2013/0028941 A1 | 1/2013 | Altreuter et al. |
| 2013/0039954 A1 | 2/2013 | Pittet et al. |
| 2013/0058894 A1 | 3/2013 | Maldonado et al. |
| 2013/0058901 A1 | 3/2013 | Maldonado et al. |
| 2013/0058902 A1 | 3/2013 | Kishimoto et al. |
| 2013/0058963 A1 | 3/2013 | Maldonado et al. |
| 2013/0058970 A1 | 3/2013 | Kishimoto et al. |
| 2013/0058974 A1 | 3/2013 | Maldonado et al. |
| 2013/0058975 A1 | 3/2013 | Maldonado et al. |
| 2013/0058976 A1 | 3/2013 | Kishimoto et al. |
| 2013/0058977 A1 | 3/2013 | Maldonado et al. |
| 2013/0058978 A1 | 3/2013 | Maldonado et al. |
| 2013/0059009 A1 | 3/2013 | Kishimoto et al. |
| 2014/0030344 A1 | 1/2014 | Zepp et al. |
| 2014/0199340 A1 | 7/2014 | Maldonado |
| 2014/0212462 A1 | 7/2014 | Kang et al. |
| 2014/0242173 A1 | 8/2014 | Zepp et al. |
| 2014/0294982 A1 | 10/2014 | Freund et al. |
| 2014/0328854 A1 | 11/2014 | Maldonado et al. |
| 2014/0328921 A1 | 11/2014 | Maldonado |
| 2014/0328922 A1 | 11/2014 | Maldonado |
| 2014/0328923 A1 | 11/2014 | Maldonado et al. |
| 2014/0328924 A1 | 11/2014 | Kishimoto |
| 2014/0335186 A1 | 11/2014 | Kishimoto et al. |
| 2014/0356361 A1 | 12/2014 | Maldonado et al. |
| 2015/0024007 A1 | 1/2015 | Hessel et al. |
| 2015/0320728 A1 | 11/2015 | Fraser et al. |
| 2015/0320856 A1 | 11/2015 | Altreuter et al. |
| 2015/0320870 A1 | 11/2015 | Maldonado |
| 2015/0320884 A1 | 11/2015 | Fraser et al. |
| 2015/0328300 A1 | 11/2015 | Zepp et al. |
| 2015/0328309 A1 | 11/2015 | Ilyinskii et al. |
| 2015/0328333 A1 | 11/2015 | Fraser et al. |
| 2015/0335762 A1 | 11/2015 | Fraser et al. |
| 2015/0359865 A1 | 12/2015 | Kishimoto |
| 2015/0374815 A1 | 12/2015 | Kishimoto et al. |
| 2016/0022650 A1 | 1/2016 | Fraser et al. |
| 2016/0030554 A1 | 2/2016 | Kishimoto et al. |
| 2016/0030555 A1 | 2/2016 | Kishimoto et al. |
| 2016/0067228 A1 | 3/2016 | Kishimoto et al. |
| 2016/0074372 A1 | 3/2016 | Kishimoto |
| 2016/0074531 A1 | 3/2016 | Kishimoto |
| 2016/0074532 A1 | 3/2016 | Kishimoto |
| 2016/0128986 A1 | 5/2016 | O'Neil et al. |
| 2016/0128987 A1 | 5/2016 | Griset et al. |
| 2016/0220501 A1 | 8/2016 | Fraser et al. |
| 2016/0243253 A1 | 8/2016 | Fraser et al. |
| 2016/0256401 A1 | 9/2016 | Fraser et al. |
| 2016/0279234 A1 | 9/2016 | Kishimoto et al. |
| 2017/0258927 A1 | 9/2017 | Johnston |
| 2017/0349433 A1 | 12/2017 | Lipford et al. |
| 2018/0043023 A1 | 2/2018 | Ilyinski et al. |
| 2018/0071394 A1 | 3/2018 | O'Neil et al. |
| 2018/0085319 A1 | 3/2018 | Kishimoto |

FOREIGN PATENT DOCUMENTS

| | | |
|---|---|---|
| JP | 2007-532517 A | 11/2007 |
| JP | 2008-515806 | 5/2008 |
| JP | 2008-532953 A | 8/2008 |
| JP | 2009-531068 | 9/2009 |
| JP | 2005-516893 A | 5/2010 |
| JP | 2010-100578 A | 5/2010 |
| JP | 2010-514805 | 5/2010 |
| JP | 2014-517828 A | 4/2014 |
| JP | 2014-514334 A | 6/2014 |
| KR | 10-2010-0099849 A | 9/2010 |
| WO | WO 88/06451 A1 | 9/1988 |
| WO | WO 95/11696 A1 | 5/1995 |
| WO | WO 1996/012406 A1 | 2/1996 |
| WO | WO 96/20698 A2 | 7/1996 |
| WO | WO 1998/010056 A1 | 12/1998 |
| WO | WO 99/22762 A1 | 5/1999 |
| WO | WO 99/34826 A1 | 7/1999 |
| WO | WO 02/09770 A1 | 2/2002 |
| WO | WO 2002/088304 A2 | 11/2002 |
| WO | WO 2003/033526 A2 | 4/2003 |
| WO | WO 2005/097116 A1 | 10/2005 |
| WO | WO 2006/041890 A2 | 4/2006 |
| WO | WO 2006/094507 A1 | 9/2006 |
| WO | WO 2007/067683 A2 | 6/2007 |

(56) References Cited

FOREIGN PATENT DOCUMENTS

| WO | WO 2007/087341 A2 | 8/2007 |
|---|---|---|
| WO | WO 2007/098254 A2 | 8/2007 |
| WO | WO 2007/133835 A2 | 11/2007 |
| WO | WO 2008/036374 A2 | 3/2008 |
| WO | WO 2008/043157 A1 | 4/2008 |
| WO | WO 2008/083331 A2 | 7/2008 |
| WO | WO 2008/109163 A1 | 9/2008 |
| WO | WO 2008/150868 A1 | 12/2008 |
| WO | WO-2009/007750 A1 | 1/2009 |
| WO | WO 2009/022154 A2 | 2/2009 |
| WO | WO 2009/039502 A1 | 3/2009 |
| WO | WO 2009/051837 A2 | 4/2009 |
| WO | WO 2009/106999 A2 | 9/2009 |
| WO | WO 2009/131712 A2 | 10/2009 |
| WO | WO 2009/145238 A1 | 12/2009 |
| WO | WO 2010/018384 A1 | 2/2010 |
| WO | WO 2010/027471 A2 | 3/2010 |
| WO | WO 2010/037402 A1 | 4/2010 |
| WO | WO 2010/042863 A1 | 4/2010 |
| WO | WO 2010/042866 | 4/2010 |
| WO | WO 2010/042870 A1 | 4/2010 |
| WO | WO 2010/042876 | 4/2010 |
| WO | WO 2010/047839 A1 | 4/2010 |
| WO | WO 2010/075072 A2 | 7/2010 |
| WO | WO 2010/116141 A2 | 10/2010 |
| WO | WO 2010/123569 A2 | 10/2010 |
| WO | WO 2010/125565 A2 | 11/2010 |
| WO | WO 2010/138192 A2 | 12/2010 |
| WO | WO 2010/138193 A2 | 12/2010 |
| WO | WO 2010/138194 | 12/2010 |
| WO | WO 2011/033090 A1 | 3/2011 |
| WO | WO 2011/109833 A2 | 9/2011 |
| WO | WO 2011/150240 A1 | 12/2011 |
| WO | WO 2011/156119 A1 | 12/2011 |
| WO | WO 2012/019041 A2 | 2/2012 |
| WO | WO 2012/021512 A2 | 2/2012 |
| WO | WO 2012/054920 A2 | 4/2012 |
| WO | WO 2012/149247 A2 | 11/2012 |
| WO | WO 2012/149252 A2 | 11/2012 |
| WO | WO 2012/149255 A2 * | 11/2012 |
| WO | WO-2012/149259 A1 | 11/2012 |
| WO | WO 2012/149265 A2 | 11/2012 |
| WO | WO 2012/149268 A1 | 11/2012 |
| WO | WO 2012/149393 A2 | 11/2012 |
| WO | WO 2012/149405 A2 | 11/2012 |
| WO | WO 2012/149411 A1 | 11/2012 |
| WO | WO 2012/158362 A1 | 11/2012 |
| WO | WO 2013/058812 A1 | 4/2013 |
| WO | WO-2014/179771 A1 | 11/2014 |

OTHER PUBLICATIONS

Aalbers et al., Preclinical Potency and Biodistribution Studies of an AAV 5 Vector Expressing Human Interferon-β for Local Treatment of Patients with Rheumatoid Arthritis. PLoS One. Jun. 24, 2015;10(6):e0130612. doi:10.1371/journal.pone.0130612. 17 pages.

Anguela et al., Robust ZFN-mediated genome editing in adult hemophilic mice. Blood. Nov. 7, 2013;122(19):3283-7. doi: 10.1182/blood-2013-04-497354. Epub Oct. 1, 2013.

Arruda et al., Strategies to modulate immune responses: a new frontier for gene therapy. Mol Ther. Sep. 2009;17(9):1492-503. doi: 10.1038/mt.2009.150. Epub Jul. 7, 2009. Review.

Barzel et al., Promoterless gene targeting without nucleases ameliorates haemophilia B in mice. Nature. Jan. 15, 2015;517(7534):360-4. doi: 10.1038/nature13864. Epub Jul. 15, 2015. 21 pages.

Bisset et al., Therapeutic impact of systemic AAV-mediated RNA interference in a mouse model of myotonic dystrophy. Hum Mol Genet. Sep. 1, 2015;24(17):4971-83. doi: 10.1093/hmg/ddv219. Epub Jun. 16, 2015.

Brown et al., Endogenous microRNA regulation suppresses transgene expression in hematopoietic lineages and enables stable gene transfer. Nat Med. May 2006;12(5):585-91. Epub Apr. 23, 2006.

Caccamo et al., Rapamycin rescues TDP-43 mislocalization and the associated low molecular mass neurofilament instability. J Biol Chem. Oct. 2, 2009;284(40):27416-24. doi: 10.1074/jbc.M109.031278. Epub Aug. 3, 2009.

Carpentier et al., Effect of alipogene tiparvovec (AAV1-LPL(S447X)) on postprandial chylomicron metabolism in lipoprotein lipase-deficient patients. J Clin Endocrinol Metab. May 2012;97(5):1635-44. doi: 10.1210/jc.2011-3002. Epub Mar. 21, 2012.

Chen et al., Targeting transgene to the heart and liver with AAV9 by different promoters. Clin Exp Pharmacol Physiol. Oct. 2015;42(10):1108-17. doi: 10.1111/1440-1681.12453. Original Article. 24 pages.

Cheng et al., Efficient gene editing in adult mouse livers via adenoviral delivery of CRISPR/Cas9. FEBS Lett. Nov. 3, 2014;588(21):3954-8. doi: 10.1016/j.febslet.2014.09.008. Epub Sep. 19, 2014.

Corti et al., B-Cell Depletion is Protective Against Anti-AAV Capsid Immune Response: A Human Subject Case Study. Mol Ther Methods Clin Dev. 2014;1. pii: 14033. 7 pages.

Denti et al., Body-wide gene therapy of Duchenne muscular dystrophy in the mdx mouse model. Proc Natl Acad Sci U S A. Mar. 7, 2006;103(10):3758-63. Epub Feb. 24, 2006.

Eghtesad et al., Effect of rapamycin on immunity induced by vector-mediated dystrophin expression in mdx skeletal muscle. Sci Reports. May 8, 2012;2:399. doi: 10.1038/srep00399. 6 pages.

Goyenvalle et al., Engineering multiple U7snRNA constructs to induce single and multiexon-skipping for Duchenne muscular dystrophy. Mol Ther. Jun. 2012;20(6):1212-21. doi: 10.1038/mt.2012.26. Epub Feb. 21, 2012.

Händel et al., Versatile and efficient genome editing in human cells by combining zinc-finger nucleases with adeno-associated viral vectors. HumGene Ther. Mar. 2012;23(3):321-9. doi: 10.1089/hum.2011.140. Epub Dec. 14, 2011.

Hui et al., Modulation of CD8+ T cell responses to AAV vectors with IgG-derived MHC class II epitopes. Mol Ther. Sep. 2013;21(9):1727-37. doi: 10.1038/mt.2013.166. Epub Jul. 16, 2013.

Ito et al., A convenient enzyme-linked immunosorbent assay for rapid screening of anti-adeno-associated virus neutralizing antibodies. Ann Clin Biochem. Nov. 2009;46(Pt 6):508-10. doi: 10.1258/acb.2009.009077. Epub Sep. 3, 2009.

Jiang et al., Effects of transient immunosuppression on adenoassociated, virus-mediated, liver-directed gene transfer in rhesus macaques and implications for human gene therapy. Blood. Nov. 15, 2006;108(10):3321-8. Epub Jul. 25, 2006.

Le Hir et al., AAV genome loss from dystrophic mouse muscles during AAV-U7 snRNA-mediated exon-skipping therapy. Mol Ther. Aug. 2013;21(8):1551-8. doi: 10.1038/mt.2013.121. Epub Jun. 11, 2013.

Louis Jeune et al., Pre-existing anti-adeno-associated virus antibodies as a challenge in AAV gene therapy. Hum Gene Ther Methods. Apr. 2013;24(2):59-67. doi: 10.1089/hgtb.2012.243. Epub Apr. 3, 2013. Review.

Manno et al., Successful transduction of liver in hemophilia by AAV-Factor IX and limitations imposed by the host immune response. Nat Med. Mar. 2006;12(3):342-7. Epub Feb. 12, 2006. Erratum in: Nat Med. May 2006;12(5):592.

Martino et al., Engineered AAV vector minimizes in vivo targeting of transduced hepatocytes by capsid-specific CD8+ T cells. Blood. Mar. 21, 2013;121(12):2224-33. doi: 10.1182/blood-2012-10-460733. Epub Jan. 16, 2013.

Meliani et al., Determination of anti-adeno-associated virus vector neutralizing antibody titer with an in vitro reporter system. Hum Gene Ther Methods. Apr. 2015;26(2):45-53. doi: 10.1089/hgtb.2015.037.

Mingozzi et al., Modulation of tolerance to the transgene product in a nonhuman primate model of AAV-mediated gene transfer to liver. Blood. Oct. 1, 2007;110(7):2334-41. Epub Jul. 3, 2007.

Moghimi et al., Induction of tolerance to factor VIII by transient co-administration with rapamycin. J Thromb Haemost. Aug. 2011;9(8):1524-33. doi: 10.1111/j.1538-7836.2011.04351.x.

(56) References Cited

OTHER PUBLICATIONS

Nathwani et al., Adenovirus-associated virus vector-mediated gene transfer in hemophilia B. N Engl J Med. Dec. 22, 2011;365(25):2357-65. doi: 10.1056/NEJMoa1108046. Epub Dec. 10, 2011.

Nathwani et al., Long-term safety and efficacy of factor IX gene therapy in hemophilia B. N Engl J Med. Nov. 20, 2014;371(21):1994-2004. doi: 10.1056/NEJMoa1407309. Epub May 20, 2015. 17 pages.

Nathwani et al., Self-complementary adeno-associated virus vectors containing a novel liverspecific human factor IX expression cassette enable highly efficient transduction of murine and nonhuman primate liver. Blood. Apr. 1, 2006;107(7):2653-61. doi: 10.1182/blood2005104035. Epub Dec. 1, 2005.

Nayak et al., Prevention and Reversal of Antibody Responses Against Factor IX in Gene Therapy for Hemophilia B. Front Microbiol. Dec. 7, 2011;2:244. doi: 10.3389/fmicb.2011.00244. eCollection 2011.

Platt et al., CRISPR-Cas9 knockin mice for genome editing and cancer modeling. Cell. Oct. 9, 2014;159(2):440-55. doi: 10.1016/j.cell.2014.09.014. Epub Sep. 25, 2014.

Post et al., Adenoviral PR39 improves blood flow and myocardial function in a pig model of chronic myocardial ischemia by enhancing collateral formation. Am J Physiol Regul Integr Comp Physiol. Mar. 2006;290(3):R494-500. Epub Oct. 27, 2005.

Ran et al., In vivo genome editing using *Staphylococcus aureus* Cas9. Nature. Apr. 9, 2015;520(7546):186-91. doi: 10.1038/nature14299. Epub Apr. 1, 2015.

Schmidt et al., CRISPR genome engineering and viral gene delivery: a case of mutual attraction. Biotechnol J. Feb. 2015;10(2):258-72. doi: 10.1002/biot.201400529. Epub Feb. 6, 2015.

Senís et al., CRISPR/Cas9-mediated genome engineering: an adeno-associated viral (AAV) vector toolbox. Biotechnol J. Nov. 2014;9(11):1402-12. doi: 10.1002/biot.201400046. Epub Oct. 6, 2014. Supporting Information. 26 pages.

Shen et al., Combined effect of cyclosporine and sirolimus on improving the longevity of recombinant adenovirus-mediated transgene expression in the retina. Arch Ophthalmol. Jul. 2001;119(7):1033-43.

Stanek et al., Silencing mutant huntingtin by adeno-associated virus-mediated RNA interference ameliorates disease manifestations in the YAC128 mouse model of Huntington's disease. Hum Gene Ther. May 2014;25(5):461-74. doi: 10.1089/hum.2013.200. Epub Mar. 21, 2014.

Weber et al., AAV-mediated delivery of zinc finger nucleases targeting hepatitis B virus inhibits active replication. PLoS One. May 14, 2014;9(5):e97579. doi: 10.1371/journal.pone.0097579. eCollection 2014. 14 pages.

Yuan et al., Preparation of rapamycin-loaded chitosan/PLA nanoparticles for immunosuppression in corneal transplantation. Int J Pharm. Feb. 12, 2008;349(1-2):241-8. Epub Aug. 11, 2007.

U.S. Appl. No. 14/717,451, filed May 20, 2015, Ilyinskii et al.

PCT/US2015/048770, Mar. 16, 2017, International Preliminary Report on Patentability.

International Search Report and Written Opinion dated Jan. 18, 2016 in connection with PCT/US2015/048770.

"Pluronic."Oxford Dictionary entry accessed via www.oxforddictionary.com on May 6, 2016. 8 pages.

Adorini et al., Tolerogenic dendritic cells induced by vitamin D receptor ligands enhance regulatory T cells inhibiting allograft rejection and autoimmune diseases. J Cell Biochem. Feb. 1, 2003;88(2):227-33.

Amu et al., Regulatory B cells prevent and reverse allergic airway inflammation via FoxP3-positive T regulatory cells in a murine model. J Allergy Clin Immunol. 2010;125:1114-24.

Ashe et al., Inhibition of glycogen biosynthesis via mTORC1 suppression as an adjunct therapy for Pompe disease. Mol Genet Metab. Aug. 2010;100(4):309-15. doi: 10.1016/j.ymgme.2010.05.001. Epub May 5, 2010.

Bae et al., Vinyl sulfone-terminated PEG-PLLA diblock copolymer for thiol-reactive polymeric micelle. Apr. 9, 2009;42(10):3437-42.

Battaglia et al., Rapamycin promotes expansion of functional CD4+CD25+FOXP3+ regulatory T cells of both healthy subjects and type 1 diabetic patients. J Immunol. Dec. 15, 2006;177(12):8338-47.

Bawarski et al., Emerging nanopharmaceuticals. Nanomed: Nanotechnol Biol Med. 2008;4:273-82.

Beevers et al., Curcumin inhibits the mammalian target of rapamycin-mediated signaling pathways in cancer cells. Int J Cancer. Aug. 15, 2006;119(4):757-64.

Binder et al., Tumor necrosis factor-inhibiting therapy preferentially targets bone destruction but not synovial inflammation in a tumor necrosis factor-driven model of rheumatoid arthritis. Arthritis Rheum. Mar. 2013;65(3):608-17. doi: 10.1002/art.37797.

Bocian et al., Rapamycin, unlike cyclosporine A, enhances suppressive functions of in vitro-induced CD4+CD25+ Tregs. Nephrol Dial Transplant. Mar. 2010;25(3):710-7. doi: 10.1093/ndt/gfp586. Epub Nov. 9, 2009.

Boden et al., Regulatory T cells in inflammatory bowel disease. Curr Opin Gastroenterol. Nov. 2008;24(6):733-41.

Bouaziz et al., Regulatory B cells as inhibitors of immune responses and inflammation. Immunol Rev. Aug. 2008;224:201-14. doi: 10.1111/j.1600-065X.2008.00661.x. Review.

Bryant et al., Nanoparticle delivery of donor antigens for transplant tolerance in allogeneic islet transplantation. Biomaterials. Oct. 2014;35(31):8887-94. doi: 10.1016/j.biomaterials.2014.06.044.

Cappellano et al., Subcutaneous inverse vaccination with PLGA particles loaded with a MOG peptide and IL-10 decreases the severity of experimental autoimmune encephalomyelitis. Vaccine. Aug. 20, 2014. pii: S0264-410X(14)01129-3. doi: 10.1016/j.vaccine.2014.08.016. 9 pages.

Colman et al., Effects of amino acid sequence changes on antibody-antigen interactions. Res Immunol. Jan. 1994;145(1):33-6.

Coombes et al., A functionally specialized population of mucosal CD103+ DCs induces Foxp3+ regulatory T cells via a TGF-beta and retinoic acid-dependent mechanism. J Exp Med. Aug. 6, 2007;204(8):1757-64. Epub Jul. 9, 2007.

Cvetanovich et al., Human regulatory T cells in autoimmune diseases. Curr Opin Immunol. Dec. 2010;22(6):753-60. Epub Sep. 24, 2010.

Dao et al., Pharmacokinetics and pharmacodynamics evaluation of therapeutic protein drugs. China Pharm. Dec. 31, 2007;18(32):2546-7.

Das et al., Delivery of rapamycin-loaded nanoparticle down regulates ICAM-1 expression and maintains an immunosuppressive profile in human CD34+ progenitor-derived dendritic cells. J Biomed Mater Res A. Jun. 15, 2008;85(4):983-92.

Davila et al., Cell-based immunotherapy with suppressor CD8+ T cells in rheumatoid arthritis. J Immunol. Jun. 1, 2005;174(11):7292-301.

Delgoffe et al., The mTOR kinase differentially regulates effector and regulatory T cell lineage commitment. Immunity. Jun. 19, 2009;30(6):832-44. doi:10.1016/j.immuni.2009.04.014.

DiLillo et al., B10 cells and regulatory B cells balance immune responses during inflammation, autoimmunity, and cancer. Ann N Y Acad Sci. Jan. 2010;1183:38-57. doi:.10.1111/j.1749-6632.2009.05137.x. Review.

DiNarvand et al., Polylactide-co-glycolide nanoparticles for controlled delivery of anticancer agents. Int J Nanomedicine. 2011;6:877-95. doi: 10.2147/IJN.S18905. Epub May 27, 2011.

DiNesh et al., CD8+ Tregs in lupus, autoimmunity, and beyond. Autoimmun Rev. Jun. 2010;9(8):560-8. doi: 10.1016/j.autrev.2010.03.006. Epub Jun. 1, 2011. 21 pages.

Dobrolovskaja et al., Immunological properties of engineered nonomaterials. Nat Nanotechnol. Aug. 2007;2(8):469-78. Review.

Düchs, Dissertation entitled: Effects of Toll-like receptor agonists on the pathogenesis of atopic asthma in mice, University of Wilrzburg, Sep. 2011. 147 pages.

Endharti et al., Cutting edge: CD8+CD122+ regulatory T cells produce IL-10 to suppress IFN-gamma production and proliferation of CD8+ T cells. J Immunol. Dec. 1, 2005;175(11):7093-7.

Falk et al., Induction and suppression of an autoimmune disease by oligomerized T cell epitopes: enhanced in vivo potency of encephalitogenic peptides. J Exp Med. Feb. 21, 2000;191(4):717-30.

(56) References Cited

OTHER PUBLICATIONS

Fasier et al., Antagonistic peptides specifically inhibit proliferation, cytokine production, CD40L expression, and help for IgE synthesis by Der p 1-specific human T-cell clones. J Allergy Clin Immunol. Apr. 1998;101(4 Pt 1):521-30.

Faunce et al., Cutting edge: in vitro-generated tolerogenic APC induce CD8+ T regulatory cells that can suppress ongoing experimental autoimmune encephalomyelitis. J Immunol. Feb. 15, 2004;172(4):1991-5.

Fifis et al., Size-dependent immunogenicity: therapeutic and protective properties of nano-vaccines against tumors. J Immunol. Sep. 1, 2004;173(5):3148-54.

Fiorino et al., A single cohort, dose escalation phase 1 study of intravenous infusion of pegsiticase (formerly Uricase-PEG 20), a drug for managing hyperuricemia in refractory gout [Abstract]. Abstracts of the American College of Rheumatology/Association of Rheumatology Health Professionals Annual Scientific Meeting. Atlanta, Georgia. Nov. 6-11, 2010. Arthritis Rheum. Nov. 2010;62 Suppl 10: 144. DOI: 10.1002/art.27913. 2 pages.

Fischer et al., Rapamycin-conditioned, alloantigen-pulsed myeloid dendritic cells present donor MHC class I/peptide via the semi-direct pathway and inhibit survival of antigen-specific CD8(+) T cells in vitro and in vivo. Transpl Immunol. Jul. 2011;25(1):20-6. Epub May 10, 2011.

Fourtounas et al., Different immunosuppressive combinations on T-cell regulation in renal transplant recipients. Am J Nephrol. 2010;32(1):1-9. doi:10.1159/000313940. Epub May 20, 2010.

Fraser et al., Nanoparticle therapy for allergic and inflammatory disease. Anti-Inflammatory & Anti-Allergy Agents Med Chem. Mar. 2010;9(1):54-70.

Gajofatto et al., Treatment strategies for multiple sclerosis: When to start, when to change, when to stop? World J Clin Cases. Jul. 16, 2015;3(7):545-55. doi: 10.12998/wjcc.v3.i7.545.

Gao et al., Contrasting effects of cyclosporine and rapamycin in de novo generation of alloantigen-specific regulatory T cells. Am J Transplant. Jul. 2007;7(7):1722-32. Epub May 19, 2007.

Garcia et al., CCR9+ and CD103+ tolerogenic dendritic cell populations in food allergy patients undergoing oral immunotherapy. Clin Transl Allergy. 2011; 1(Suppl 1): O51.

Getts et al., Harnessing nanoparticles for immune modulation. Trends Immunol. Jul. 2015;36(7):419-27.

Gray et al., Apoptotic cells protect mice from autoimmune inflammation by the induction of regulatory B cells. Proc Natl Acad Sci U S A. Aug. 28, 2007;104(35):14080-5. Epub Aug. 21, 2007.

Gray et al., What are regulatory B cells? Eur J Immunol. Oct. 2010;40(10):2677-9.

Haddadi et al., Delivery of rapamycin by PLGA nanoparticles enhances its suppressive activity on dendritic cells. J Biomed Mater Res A. Mar. 15, 2008;84(4):885-98.

Hahn et al., Cellular and molecular mechanisms of regulation of autoantibody production in lupus. Ann N Y Acad Sci. Jun. 2005;1051:433-41. Review. Epub Apr. 10, 2008. 9 pages.

Hahn et al., Tolerogenic treatment of lupus mice with consensus peptide induces Foxp3-expressing, apoptosis-resistant, TGFbeta-secreting CD8+ T cell suppressors. J Immunol. Dec. 1, 2005;175(11):7728-37.

Hamdy et al., Co-delivery of cancer-associated antigen and Toll-like receptor 4 ligand in PLGA nanoparticles induces potent CD8+ T cell-mediated anti-tumor immunity. Vaccine. Sep. 15, 2008;26(39):5046-57. doi: 10.1016/j.vaccine.2008.07.035. Epub Aug. 3, 2008.

Hamdy et al., Part I: targeted particles for cancer immunotherapy. Curr Drug Deliv. May 2011;8(3):261-73.

Hamdy et al., Targeting dendritic cells with nano-particulate PLGA cancer vaccine formulations. Adv Drug Deliv Rev. Sep. 10, 2011;63(10-11):943-55. doi: 10.1016/j.addr.2011.05.021. Epub Jun. 6, 2011. Review.

Hamdy et al., The immunosuppressive activity of polymeric micellar formulation of cyclosporine A: in vitro and in vivo studies. AAPS J. Jun. 2011;13(2):159-68. doi: 10.1208/s12248-011-9259-8. Epub Feb. 19, 2011.

Hashimoto et al., Stimulation of host NKT cells by synthetic glycolipid regulates acute graft-versus-host disease by inducing Th2 polarization of donor T cells. J Immunol. Jan. 1, 2005;174(1):551-6.

Imamura et al., Pravastatin attenuates allergic airway inflammation by suppressing antigen sensitisation, interleukin 17 production and antigen presentation in the lung. Thorax. Jan. 2009;64(1):44-9. doi: 10.1136/thx.2007.094540. Epub Oct. 3, 2008.

Jhunjhunwala et al., Delivery of rapamycin to dendritic cells using degradable microparticles. J Control Release. Feb. 10, 2009;133(3):191-7. doi: 10.1016/j.jconrel.2008.10.011. Epub Oct. 26, 2008.

Jones, Critically assessing the state-of-the-art in protein structure prediction. Pharmacogenomics J. 2001;1(2):126-34. Review.

Kang et al., Very low-dose tolerance with nucleosomal peptides controls lupus and induces potent regulatory T cell subsets. J Immunol. Mar. 15, 2005;174(6):3247-55.

Karamloo et al., Prevention of allergy by a recombinant multi-allergen vaccine with reduced IgE binding and preserved T cell epitopes. Eur J Immunol. Nov. 2005;35(11):3268-76.

Keselowsky et al., Multifunctional dendritic cell-targeting polymeric microparticles: engineering new vaccines for type 1 diabetes. Hum Vaccin. Jan. 1, 2011;7(1):37-44. Epub Jan. 1, 2011. Review.

Kim et al., Effects of cyclosporine and rapamycin on immunoglobulin production by preactivated human B cells. Clin Exp Immunol. Jun. 1994;96(3):508-12.

Kim et al., Inhibition of follicular T-helper cells by CD8(+) regulatory T cells is essential for self. Nature. Sep. 16, 2010;467(7313):328-32.

Kim et al., Simvastatin induces Foxp3+ T regulatory cells by modulation of transforming growth factor-beta signal transduction. Immunology. Aug. 2010;130(4):484-93. doi: 10.1111/j.1365-2567.2010.03269.x. Epub Apr. 12, 2010.

Kingsley et al., Transplantation tolerance: lessons from experimental rodent models. Transpl Int. Oct. 2007;20(10):828-41. Epub Aug. 17, 2007.

Konya et al., Treating autoimmune disease by targeting CD8(+) T suppressor cells. Expert Opin Biol Ther. Aug. 2009;9(8):951-65. doi: 10.1517/14712590903020759. Review. Epub Aug. 1, 2010. 22 pages.

Lassmann et al., The molecular basis of neurodegeneration in multiple sclerosis. FEBS Lett. Dec. 1, 2011;585(23):3715-23. doi: 10.1016/j.febslet.2011.08.004. Epub Aug. 16, 2011.

Lu et al., Rapamycin promotes the expansion of CD4(+) Foxp3(+) regulatory T cells after liver transplantation. Transplant Proc. Jun. 2010;42(5):1755-7. doi: 10.1016/j.transproceed.2009.10.008.

Lutsiak et al., Analysis of poly(D,L-lactic-co-glycolic acid) nanosphere uptake by human dendritic cells and macrophages in vitro. Pharm Res. Oct. 2002;19(10):1480-7.

Maldonado et al., Polymeric synthetic nanoparticles for the induction of antigen-specific immunological tolerance. Proc Natl Acad Sci U S A. Jan. 13, 2015;112(2):E156-65. doi: 10.1073/pnas.1408686111. Epub Dec. 29, 2014.

Mason, Functional Analysis of the Cysteine Residues of Activin A. Mol Endocrinol. 1994;8(3):325-32.

McMahon et al., Epitope spreading initiates in the CNS in two mouse models of multiple sclerosis. Nat Med. Mar. 2005;11(3):335-9. Epub Feb. 27, 2005.

Menzies et al., Simvastatin does not exhibit therapeutic anti-inflammatory effects in asthma. J Allergy Clin Immunol. Feb. 2007;119(2):328-35. Epub Dec. 4, 2006.

Miyara et al., Therapeutic approaches to allergy and autoimmunity based on FoxP3+ regulatory T-cell activation and expansion. J Allergy Clin Immunol. Apr. 2009;123(4):749-55.

Moraes-Fontes et al., Steroid treatments in mice do not alter the number and function of regulatory T cells, but amplify cyclophosphamide-induced autoimmune disease. J Autoimmun. Sep. 2009;33(2):109-20. doi: 10.1016/j.jaut.2009.03.008. Epub Apr. 11, 2009.

Mottram et al., Type 1 and 2 immunity following vaccination is influenced by nanoparticle size: formulation of a model vaccine for respiratory syncytial virus. Mol Pharm. Jan.-Feb. 2007;4(1):73-84.

Neuhaus et al., mTOR inhibitors: an overview. Liver Transpl. Jun. 2001;7(6):473-84.

(56) References Cited

OTHER PUBLICATIONS

Ngo et al., In the Protein Folding Problem and Tertiary Structure Prediction, 1994. Eds Mertz et al. Birkhauser. Boston, MA. 1994:433,491-5.

Nixon et al., Synthetic peptides entrapped in microparticles can elicit cytotoxic T cell activity. Vaccine. Nov. 1996;14(16):1523-30.

Oh et al., CD4+CD25+ regulatory T cells in autoimmune arthritis. Immunol Rev. Jan. 2010;233(1):97-111.

Omata et al., Ovalbumin-specific IgE modulates ovalbumin-specific T-cell response after repetitive oral antigen administration. J Allergy Clin Immunol. Apr. 2005;115(4):822-7.

Paolicelli et al., Surface-modified PLGA-based nanoparticles that can efficiently associate and deliver virus-like particles. Nanomedicine (Lond). Aug. 2010;5(6):843-53.

Papisov, Acyclic polyacetals from polysaccharides: biomimetic biomedical "stealth" polymers. Chapter 19. ACS Symposium Series. Feb. 15, 2001:786:301-14.

Reichardt et al., Impact of Mammalian Target of Rapamycin Inhibition on Lymphoid Homing and Tolerogenic Function of Nanoparticle-Labeled Dendritic Cells following Allogeneic Hematopoietic Cell Transplantation. J Immunol. 2008;181:4770-9.

Samuel et al., Nanoparticle delivery systems for control of immunity. Proceedings of the 2004 Intl. Conference on MEMS, NANO and Smart Systems (ICMENS '04). IEEE 2004. 3 pages.

Samuel et al., Polymeric nanoparticles for targeted delivery of Therapeutic Vaccines to dendritic cells. Proceedings of the International Conference on MEMS, NANO and Smart Systems. (ICMENS '03). IEEE 2003. 5 pages.

Sbiera et al., Influence of short-term glucocorticoid therapy on regulatory T cells in vivo. PLoS One. 2011;6(9):e24345. doi: 10.1371/journal.pone.0024345. Epub Sep. 2, 2011.

Seffernick et al., Melamine deaminase and atrazine chlorohydrolase: 98 percent identical but functionally different. J Bacteriol. Apr. 2001;183(8):2405-10.

Sharabi et al., The suppression of murine lupus by a tolerogenic peptide involves foxp3-expressing CD8 cells that are required for the optimal induction and function of foxp3-expressing CD4 cells. J Immunol. Sep. 1, 2008;181(5):3243-51.

Shimizu et al., Direct anti-inflammatory mechanisms contribute to attenuation of experimental allograft arteriosclerosis by statins. Circulation. Oct. 28, 2003;108(17):2113-20. Epub Sep. 29, 2003.

Skolnick et al., From genes to protein structure and function: novel applications of computational approaches in the genomic era. Trends Biotechnol. Jan. 2000;18(1):34-9. Review.

Soroosh et al., Th9 and allergic disease. Immunology. Aug. 2009;127(4):450-8. doi: 10.1111/j.1365-2567.2009.03114.x.

Stepkowski et al., Inhibition of host-versus-graft and graft-versus-host responses after small bowel transplantation in rats by rapamycin. Transplantation. Feb. 1992;53(2):258-64.

Suzuki et al., Inhibitory CD8+ T cells in Autoimmune Disease. Hum Immunol. Nov. 2008;69(11):781-9. doi:10.1016/j.humimm.2008.08.283. Epub Nov. 1, 2009.

Tai et al., A novel rapamycin-polymer conjugate based on a new poly(ethylene glycol) multiblock copolymer. Pharm Res. Mar. 2014;31(3):706-19. doi: 10.1007/s11095-013-1192-3. Epub Sep. 26, 2013.

Tarzi et al., Peptide immunotherapy for allergic disease. Expert Opin Biol Ther. Jul. 2003;3(4):617-26. Review.

Thomson et al., Immunoregulatory functions of mTOR inhibition. Nat Rev Immunol. May 2009;9(5):324-37. doi: 10.1038/nri2546.

Tosatto et al., Large-scale prediction of protein structure and function from sequence. Curr Pharm Des. 2006;12(17):2067-86. Review.

Tuohy, Peptide determinants of myelin proteolipid protein (PLP) in autoimmune demyelinating disease: a review. Neurochem Res. Aug. 1994;19(8):935-44.

Turnquist et al., Rapamycin-conditioned dendritic cells are poor stimulators of allogeneic CD4+ T cells, but enrich for antigen-specific Foxp3+ T regulatory cells and promote organ transplant tolerance. J Immunol. Jun. 1, 2007;178(11):7018-31.

Vila et al., Regulatory T cells and autoimmunity. Curr Opin Hematol. Jul. 2009;16(4):274-9.

Wang et al., A systematic assessment of MHC class II peptide binding predictions and evaluation of a consensus approach. PLoS Comput Biol. Apr. 4, 2008;4(4):e1000048. doi: 10.1371/journal.pcbi.1000048.

Witkowski et al., Conversion of a beta-ketoacyl synthase to a malonyl decarboxylase by replacement of the active-site cysteine with glutamine. Biochemistry. Sep. 7, 1999;38(36):11643-50.

Wu et al., Humanization of a murine monoclonal antibody by simultaneous optimization of framework and CDR residues. J Mol Biol. Nov. 19, 1999;294(1):151-62.

Yamaguchi et al., Around hematological malignancies. Trends in Hematological Malignancies. 2010;2(2):96-98.

Yamaki et al., Preventive and therapeutic effects of rapamycin, a mammalian target of rapamycin inhibitor, on food allergy in mice. Allergy. Oct. 2012;67(10):1259-70. doi: 10.1111/all.12000. Epub Aug. 23, 2012.

Yeste et al., Nanoparticle-mediated codelivery of myelin antigen and a tolerogenic small molecule suppresses experimental autoimmune encephalomyelitis. Proc Natl Acad Sci U S A. Jul. 10, 2012;109(28):11270-5. doi: 10.1073/pnas.1120611109. Epub Jun. 27, 2012.

Zhang et al., The mechanism of B lymphocytes in inducing immune tolerance. Immunol J. Jul. 2010;26(7):643-6.

Zhang-Hoover et al., Tolerogenic APC generate CD8+ T regulatory cells that modulate pulmonary interstitial fibrosis. J Immunol. Jan. 1, 2004;172(1):178-85.

Zhou et al., Updates of mTOR inhibitors. Anticancer Agents Med Chem. Sep. 2010;10(7):571-81.

Zweers, Biodegradable nanoparticles of intravascular drug delivery. Unversiteit Twente, 2003.

[No Author Listed] Selecta Biosciences Announces Dosing of First Patent in Phase 1b Clinical Trial of SEL-212, Designed to be the First Non-Immunogenic Biologic Treatment for Gout. Press Release. Dec. 23, 2015. Retrieved from the Internet via http://selectabio.com/2015/12/23/selecta-biosciences-announces-dosing-of-first-patient-in-phase-1b-clinical-trial-of-sel-212-designed-to-be-the-first-non-immunogenic-biologic-treatment-for-gout. Last access on May 10, 2017.

Berhanu et al., Pegloticase failure and a possible solution: Immunosuppression to prevent intolerance and inefficacy in patients with gout. Semin Arthritis Rheum. Jun. 2017;46(6):754-758. doi: 10.1016/j.semarthrit.2016.09.007. Epub Sep. 20, 2016.

Hershfield et al., Induced and pre-existing anti-polyethylene glycol antibody in a trial of every 3-week dosing of pegloticase for refractory gout, including in organ transplant recipients. Arthritis Res Ther. Mar. 7, 2014;16(2):R63. doi: 10.1186/ar4500.

Ishii, [Allergen-specific immunotherapy utilizing mechanisms for immune; regulation]. Nihon Rinsho Meneki Gakkai Kaishi. Oct. 2008;31(5):392-8. Review.

Kishimoto et al., Improving the efficacy and safety of biologic drugs with; tolerogenic nanoparticles. Nat Nanotechnol. Oct. 2016;11(10):890-899. doi:; 10.1038/nnano.2016.135. Epub Aug. 1, 2016.

Kunisawa et al., Fusogenic liposome functions as an efficient immunoadjuvant in inducing humoral immune-responses to soluble antigen. Drug Delivery System. Jan 1998;13(1):21-26.

Lipsky et al., Pegloticase immunogenicity: the relationship between efficacy and antibody development in patients treated for refractory chronic gout. Arthritis Res Ther. Mar. 4, 2014;16(2):R60. doi: 10.1186/ar4497.

Macary et al., Ovalbumin-specific, MHC class 1-restricted, alpha beta-positive, Tc1 and Tc0 CD8+ T cell clones mediate the in vivo inhibition of rat IgE. J Immunol. Jan. 15, 1998;160(2):580-7.

McKay et al., A novel anti-inflammatory role of simvastatin in a murine model of allergic asthma. J Immunol. Mar. 1, 2004;172(5):2903-8.

Mine et al., Epitope characterization of ovalbumin in BALB/c mice using different entry routes. Biochim Biophys Acta. Feb. 2007;1774(2):200-12. Epub Dec. 19, 2006.

Quarcoo et al., Resiquimod, a new immune response modifier from the family of imidazoquinolinamines, inhibits allergen-induced Th2

(56) References Cited

OTHER PUBLICATIONS responses, airway inflammation and airway hyper-reactivity in mice. Clin Exp Allergy. Aug. 2004;34(8):1314-20.
Renz et al., Comparison of the allergenicity of ovalbumin and ovalbumin peptide 323-339. Differential expansion of V beta-expressing T cell populations. J Immunol. Dec. 15, 1993;151(12):7206-13.
U.S. Appl. No. 13/948,129, filed Jul. 22, 2013, Zepp et al.
U.S. Appl. No. 14/273,099, filed May 8, 2014, Zepp et al.
U.S. Appl. No. 12/788,261, filed May 26, 2010, Lipford et al.
U.S. Appl. No. 14/658,040, filed Mar. 13, 2015, Zepp et al.
U.S. Appl. No. 12/862,076, filed Aug. 24, 2010, Fraser et al.
U.S. Appl. No. 13/116,453, filed May 26, 2011, Bratzler et al.
U.S. Appl. No. 12/764,569, filed Apr. 21, 2010, Lipford et al.
U.S. Appl. No. 15/629,973, filed Jun. 22, 2017, Lipford et al.
U.S. Appl. No. 13/116,488, filed May 26, 2011, Bratzler et al.
U.S. Appl. No. 15/684,896, filed Aug. 23, 2017, Ilyinskii et al.
U.S. Appl. No. 13/116,556, filed May 26, 2011, Bratzler et al.
U.S. Appl. No. 13/289,211, filed Nov. 4, 2011, Zepp et al.
U.S. Appl. No. 13/428,340, filed Mar. 23, 2012, Altreuter et al.
U.S. Appl. No. 15/050,397, filed Feb. 22, 2016, Fraser et al.
U.S. Appl. No. 14/810,418, filed Jul. 27, 2015, Fraser et al.
U.S. Appl. No. 14/802,260, filed Jul. 17, 2015, Altreuter et al.
U.S. Appl. No. 13/560,955, filed Jul. 27, 2012, Altreuter et al.
U.S. Appl. No. 14/810,427, filed Jul. 27, 2015, Fraser et al.
U.S. Appl. No. 15/061,096, filed Mar. 4, 2016, Fraser et al.
U.S. Appl. No. 13/457,994, filed Apr. 27, 2012, Fraser et al.
U.S. Appl. No. 14/810,442, filed Jul. 27, 2015, Fraser et al.
U.S. Appl. No. 14/810,450, filed Jul. 27, 2015, Fraser et al.
U.S. Appl. No. 14/810,457, filed Jul. 27, 2015, Kishimoto et al.
U.S. Appl. No. 15/061,204, filed Mar. 4, 2016, Kishimoto et al.
U.S. Appl. No. 13/457,936, filed Apr. 27, 2012, Kishimoto et al.
U.S. Appl. No. 14/810,466, filed Jul. 27, 2015, Kishimoto et al.
U.S. Appl. No. 13/458,220, filed Apr. 27, 2012, Fraser et al.
U.S. Appl. No. 14/810,472, filed Jul. 27, 2015, Fraser et al.
U.S. Appl. No. 14/161,660, filed Jan. 22, 2014, Maldonado.
U.S. Appl. No. 14/810,476, filed Jul. 27, 2015, Maldonado.
U.S. Appl. No. 14/269,047, filed May 2, 2014, Maldonado et al.
U.S. Appl. No. 14/296,204, filed Jun. 4, 2014, Maldonado et al.
U.S. Appl. No. 14/269,048, filed May 2, 2014, Maldonado.
U.S. Appl. No. 14/269,054, filed May 2, 2014, Maldonado.
U.S. Appl. No. 14/269,058, filed May 2, 2014, Kishimoto.
U.S. Appl. No. 14/269,056, filed May 2, 2014, Maldonado et al.
U.S. Appl. No. 14/269,042, filed May 2, 2014, Kishimoto et al.
U.S. Appl. No. 14/742,583, filed Jun. 17, 2015, Kishimoto.
U.S. Appl. No. 14/751,106, filed Jun. 25, 2015, Kishimoto et al.
U.S. Appl. No. 14/846,949, filed Sep. 7, 2015, Kishimoto.
U.S. Appl. No. 14/846,952, filed Sep. 7, 2015, Kishimoto.
U.S. Appl. No. 14/846,958, filed Sep. 7, 2015, Kishimoto.
U.S. Appl. No. 14/934,132, filed Nov. 5, 2015, Griset et al.
U.S. Appl. No. 14/934,135, filed Nov. 5, 2015, Griset et al.
U.S. Appl. No. 14/846,967, filed Sep. 7, 2015, Kishimoto.
U.S. Appl. No. 15/456,520, filed Mar. 11, 2017, Johnston.
U.S. Appl. No. 15/685,648, filed Aug. 24, 2017, O'Neil.
U.S. Appl. No. 15/717,710, filed Sep. 27, 2017, Kishimoto.
U.S. Appl. No. 15/863,076, filed Jan. 5, 2018, Ilyinskii et al.
Alewine et al., Efficacy of RG7787, a next-generation mesothelin-targeted immunotoxin, against triple-negative breast and gastric cancers. Mol Cancer Ther. Nov. 2014;13(11):2653-61. doi: 10.1158/1535-7163.MCT-14-0132. Epub Sep. 19, 2014.
Baker et al., Immunogenicity of protein therapeutics: The key causes, consequences and challenges. Self Nonself—Immune Recognition and Signaling. Dec. 1, 2010;1(4):314-22.
Hassan et al., Major cancer regressions in mesothelioma after treatment with an anti-mesothelin immunotoxin and immune suppression. Sci Transl Med. Oct. 23, 2013;5(208):208ra147. doi: 10.1126/scitranslmed.3006941.

Maldonado et al., How tolerogenic dendritic cells induce regulatory T cells. Adv Immunol. 2010;108:111-65. doi: 10.1016/B978-0-12-380995-7.00004-5. Review.
Mazor et al., Immunogenicity of therapeutic recombinant immunotoxins. Immunol Rev. Mar. 2016;270(1):152-64. doi: 10.1111/imr.12390. Review.
Onda et al., Tofacitinib suppresses antibody responses to protein therapeutics in murine hosts. J Immunol. Jul. 1, 2014;193(1):48-55. doi: 10.4049/jimmunol.1400063. Epub Jun. 2, 2014.
Pastan et al., Immunotoxin therapy of cancer. Nat Rev Cancer. Jul. 2006;6(7):559-65. Review.
Rizvi et al., Activity and safety of nivolumab, an anti-PD-1 immune checkpoint inhibitor, for patients with advanced, refractory squamous non-small-cell lung cancer (CheckMate 063): a phase 2, single-arm trial. Lancet Oncol. Mar. 2015;16(3):257-65. doi: 10.1016/S1470-2045(15)70054-9. Epub Feb. 20, 2015.
Zhang, Introduction to basic medicine. China University of Science and Technology Press. Aug. 31, 2012:423.
Anaphylaxis. Manuals for Management of Individual Serious Adverse Drug Reactions. Ministry of Health, Labor and Welfare. Mar. 2008:1-34. Accessed online via http://www.info.pmda.go.jp/juutoku/file/jfm0803003.pdf.
Drug delivery system. Nankodo Co., Ltd. Apr. 15, 1986:70-1.
New pharmacology. Nankodo Co. Ltd. 3rd Revised Ed. 1996:p468.
Azzi et al., Polylactide-cyclosporin A nanoparticles for targeted immunosuppression. FASEB J. Oct. 2010; 24(10):3927-38. doi: 10.1096/fj.10-154690. Epub Jun. 14, 2010.
Bayle et al., Rapamycin analogs with differential binding specificity permit orthogonal control of protein activity. Chem Biol. Jan. 2006; 13(1):99-107.
Bi et al., High-efficiency targeted editing of large viral genomes by RNA-guided nucleases. PLoS Pathog. May 1, 2014; 10(5):e1004090. doi: 10.1371/journal.ppat.1004090. eCollection May 2014.
Esposito et al., Rapamycin inhibits relapsing experimental autoimmune encephalomyelitis by both effector and regulatory T cells modulation. J Neuroimmunol. Mar. 30, 2010; 220(1-2):52-63. doi: 10.1016/j.jneuroim.2010.01.001. Epub Feb. 11, 2010.
Goyenvalle et al., Rescue of dystrophic muscle through U7 snRNA-mediated exon skipping. Science. Dec. 3, 2004; 306(5702):1796-9. Epub Nov. 4, 2004.
Maher et al., Targeting cytotoxic T lymphocytes for cancer immunotherapy. Br J Cancer. Aug. 31, 2004; 91(5):817-21. Review.
McFarland et al., Ovalbumin(323-339) peptide binds to the major histocompatibility complex class II I-A(d) protein using two functionally distinct registers. Biochemistry. Dec. 14, 1999; 38(50):16663-70.
Mori et al., Biological drug for refractory juvenile idiopathic arthritis. Clin Rheum. 2006; 18(2):191-6.
Nayak et al., Prophylactic immune tolerance induced by changing the ratio of antigen-specific effector to regulatory T cells. J Thromb Haemost. Sep. 2009;7(9):1523-32. doi: 10.1111/j.1538-7836.2009.03548.x. Epub Jul. 6, 2009.
Reddy et al., Detection of autoreactive myelin proteolipid protein 139-151-specific T cells by using MHC II (IAs) tetramers. J Immunol. Jan. 15, 2003; 170(2):870-7.
Rice-Ficht et al., Polymeric particles in vaccine delivery. Curr Opin Microbiol. Feb. 2010;13(1):106-12. doi: 10.1016/j.mib.2009.12.001. Epub Jan. 14, 2010. Review.
Rybak-Smith et al., Complement activation by carbon nanotubes. Adv Drug Deliv Rev. Sep. 16, 2011;63(12):1031-41. doi: 10.1016/j.addr.2011.05.012. Epub Jun. 12, 2011. Review.
Sato et al., Induction of immunotolerance by the application of chase-sulzberger effect. JP J Translpant. 1995; 30(3):231-9.
Sato et al., Prolongation of the immunosuppression by repeated injections of donor antigen via the portal vein. JP J Transplant. 1995;30(2):149-54.
Zhang et al., Induction of tolerance of FVIII using nanoparticles in a murine model of hemophilia A. Blood. Nov. 15, 2013; 122:2337.

* cited by examiner

METHODS AND COMPOSITIONS FOR ATTENUATING GENE EXPRESSION MODULATING ANTI-VIRAL TRANSFER VECTOR IMMUNE RESPONSES

RELATED APPLICATIONS

This application claims the benefit under 35 U.S.C. § 119 of U.S. provisional application 62/047,034, filed Sep. 7, 2014; 62/051,255, filed Sep. 16, 2014; 62/101,841, filed Jan. 9, 2015; 62/047,044, filed Sep. 7, 2014, 62/051,258, filed Sep. 16, 2014; 62/101,861, filed Jan. 9, 2015; 62/047,054, filed Sep. 7, 2014; 62/051,263, filed Sep. 16, 2014; 62/101,872, filed Jan. 9, 2015; 62/047,051, filed Sep. 7, 2014, 62/051,267, filed Sep. 16, 2014; and 62/101,882, filed Jan. 9, 2015; the entire contents of each of which are incorporated herein by reference.

FIELD OF THE INVENTION

The invention relates to methods and compositions for administering viral transfer vectors and antigen-presenting cell targeted immunosuppressants.

SUMMARY OF THE INVENTION

Provided herein are methods and compositions for administering gene expression modulating viral transfer vectors and antigen-presenting cell targeted immunosuppressants. The viral transfer vector comprises a gene expression modulating transgene that encodes a protein, peptide or nucleic acid that may have a therapeutic benefit for any one of the purposes provided herein in any one of the methods or compositions provided herein.

In one aspect is a method comprising establishing an anti-viral transfer vector attenuated response in a subject by concomitant administration of an antigen-presenting cell targeted immunosuppressant and viral transfer vector to the subject. In one embodiment, the subject does not have pre-existing immunity against the viral transfer vector.

In one embodiment of any one of the methods provided herein, the anti-viral transfer vector attenuated response is a T cell response against the viral transfer vector, and the method further comprises administering the viral transfer vector to the subject without an antigen-presenting cell targeted immunosuppressant prior to the concomitant administration of the antigen-presenting cell targeted immunosuppressant and viral transfer vector.

In one embodiment of any one of the methods provided herein, the concomitant administration of the antigen-presenting cell targeted immunosuppressant and viral transfer vector is repeated, concomitant administration of the antigen-presenting cell targeted immunosuppressant and viral transfer vector.

In another aspect is a method comprising establishing an anti-viral transfer vector attenuated response in a subject by concomitant administration of an antigen-presenting cell targeted immunosuppressant and viral transfer vector to the subject, and administering to the subject one or more repeat doses of the viral transfer vector.

In one embodiment of any one of the methods provided herein, the anti-viral transfer vector attenuated response is a T cell response against the viral transfer vector, and the method further comprises administering the viral transfer vector to the subject without an antigen-presenting cell targeted immunosuppressant prior to both the concomitant administration of the antigen-presenting cell targeted immunosuppressant and viral transfer vector and the one or more repeat doses of the viral transfer vector.

In one embodiment of any one of the methods provided herein, the method further comprises providing or obtaining an antigen-presenting cell targeted immunosuppressant alone or in combination with a viral transfer vector.

In another aspect is a method comprising attenuating an anti-viral transfer vector response, wherein the anti-viral transfer vector response is a T cell response, by first administering to a subject a viral transfer vector without an antigen-presenting cell targeted immunosuppressant, and subsequently concomitantly administering the viral transfer vector and an antigen-presenting cell targeted immunosuppressant to the subject.

In one embodiment of any one of the methods provided, the method further comprises administering to the subject one or more repeat doses of the viral transfer vector subsequent to the concomitant administration of the viral transfer vector and the antigen-presenting cell targeted immunosuppressant to the subject.

In another aspect is a method comprising determining a level of pre-existing immunity to a viral transfer vector in a subject prior to administration of the viral transfer vector to the subject, concomitantly administering to the subject an antigen-presenting cell targeted immunosuppressant and viral transfer vector, and administering to the subject a dose of the viral transfer vector.

In one embodiment of any one of the methods provided, the determining comprises measuring a level of anti-viral transfer vector antibodies in the subject prior to administration of the viral transfer vector to the subject. In another embodiment of any one of the methods provided, the determining comprises measuring a level of a T cell response against the viral transfer vector in the subject prior to administration of the viral transfer vector to the subject.

In one embodiment of any one of the methods provided, the method further comprises one or more repeat doses of the viral transfer vector.

In one embodiment of any one of the methods provided, the level of pre-existing immunity is to a viral antigen of the viral transfer vector. In one embodiment of any one of the methods provided, the level of pre-existing immunity is to an antigen of a protein transgene expression product of the viral transfer vector.

In another aspect is a method comprising escalating transgene expression of a viral transfer vector in a subject by repeatedly, concomitantly administering to the subject an antigen-presenting cell targeted immunosuppressant and viral transfer vector.

In one embodiment of any one of the methods provided, the method further comprises determining the frequency and dosing of the repeated, concomitant administration of the antigen-presenting cell targeted immunosuppressant and viral transfer vector that increase the transgene expression in a subject.

In another aspect is a method comprising repeatedly, concomitantly administering to a subject an antigen-presenting cell targeted immunosuppressant and viral transfer vector, and selecting one or more doses of the viral transfer vector to be less than the dose of the viral transfer vector that would be selected for the subject if the subject were expected to develop anti-viral transfer vector immune responses due to the repeated administration of the viral transfer vector.

In another aspect is a method comprising inducing an entity to purchase or obtain an antigen-presenting cell targeted immunosuppressant alone or in combination with a viral transfer vector by communicating to the entity that concomitant administration of the antigen-presenting cell targeted immunosuppressant and viral transfer vector results in an anti-viral transfer vector attenuated response in a subject.

In another aspect is a method comprising inducing an entity to purchase or obtain an antigen-presenting cell targeted immunosuppressant alone or in combination with a viral transfer vector by communicating to the entity that efficacious repeated viral transfer vector dosing is possible by concomitant administration of the antigen-presenting cell targeted immunosuppressant and viral transfer vector to a subject.

In one embodiment of any one of the methods provided herein, the communicating further includes instructions for practicing any one of the methods described herein or information describing the benefits of concomitant administration of a viral transfer vector with an antigen-presenting cell targeted immunosuppressant.

In one embodiment of any one of the methods provided herein, the method further comprises distributing an antigen-presenting cell targeted immunosuppressant or a viral transfer vector or both to an entity.

In another aspect is a method comprising determining the frequency and dosing of concomitant administration of an antigen-presenting cell targeted immunosuppressant and viral transfer vector in order to generate an anti-viral transfer vector attenuated response in a subject.

In one embodiment of any one of the methods provided herein, the method further comprises directing the concomitant administration of the antigen-presenting cell targeted immunosuppressant and viral transfer vector to a subject according to the determined frequency and dosing.

In another aspect is a method comprising determining the frequency and dosing of concomitant administration of an antigen-presenting cell targeted immunosuppressant and viral transfer vector in combination with one or more repeat doses of the viral tranfer vector in order to generate an anti-viral transfer vector attenuated response in a subject.

In one embodiment of any one of the methods provided herein, the method further comprises directing both the concomitant administration of the antigen-presenting cell targeted immunosuppressant and viral transfer vector and administration of the one or more repeat doses of the viral transfer vector to a subject according to the determined frequency and dosing.

In one embodiment of any one of the methods provided herein, the method further comprises directing the administration of a dose of the viral transfer vector to the subject prior to both the concomitant administration of the antigen-presenting cell targeted immunosuppressant and viral transfer vector and administration of the one or more repeat doses of the viral transfer vector to the subject.

In one embodiment of any one of the methods provided herein, the subject is one to which the viral transfer vector has not been previously administered.

In one embodiment of any one of the methods provided herein, the subject is one to which the viral transfer vector has been previously administered no more than once.

In one embodiment of any one of the methods provided, the amount of the viral transfer vector in the repeat dose(s) is at least equal to the amount of the viral transfer vector in a prior dose. In one embodiment of any one of the methods provided, the amount of the viral transfer vector in the repeat dose(s) is less than the amount of the viral transfer vector in a prior dose.

In one embodiment of any one of the methods provided, the antigen-presenting cell targeted immunosuppressant is also administered to the subject concomitantly with the one or more repeat doses of the viral transfer vector. In one embodiment of any one of the methods provided, the antigen-presenting cell targeted immunosuppressant is not also administered to the subject concomitantly with at least one of the one or more repeat doses of the viral transfer vector.

In one embodiment of any one of the methods provided, the subject does not have pre-existing immunity against the viral transfer vector.

In one embodiment of any one of the methods provided, the concomitant administration is simultaneous administration.

In one embodiment of any one of the methods provided, the method further comprises determining a level of pre-existing immunity to the viral transfer vector in the subject.

In one embodiment of any one of the methods provided herein, the viral transfer vector is a retroviral transfer vector, an adenoviral transfer vector, a lentiviral transfer vector or an adeno-associated viral transfer vector.

In one embodiment of any one of the methods provided herein, the viral transfer vector is an adenoviral transfer vector, and the adenoviral transfer vector is a subgroup A, subgroup B, subgroup C, subgroup D, subgroup E, or subgroup F adenoviral transfer vector.

In one embodiment of any one of the methods provided herein, the viral transfer vector is a lentiviral transfer vector, and the lentiviral transfer vector is an HIV, SIV, FIV, EIAVor ovine lentiviral vector.

In one embodiment of any one of the methods provided herein, the viral transfer vector is an adeno-associated viral transfer vector, and the adeno-associated viral transfer vector is an AAV1, AAV2, AAV5, AAV6, AAV6.2, AAV7, AAV8, AAV9, AAV10 or AAV11 adeno-associated viral transfer vector.

In one embodiment of any one of the methods provided herein, the viral transfer vector is a chimeric viral transfer vector. In one embodiment of any one of the methods provided herein, the chimeric viral transfer vector is an AAV-adenoviral transfer vector.

In one embodiment of any one of the methods provided herein, the gene expression modulating transgene encodes a DNA-binding protein or a therapeutic RNA. In one embodiment of any one of the methods provided herein, the DNA-binding protein is an artificial transcription factor. In one embodiment of any one of the methods provided herein, the therapeutic RNA is an inhibitor of mRNA translation, agent of RNA interference (RNAi), catalytically active RNA molecule (ribozyme), transfer RNA (tRNA) or a RNA that binds a protein or other molecular ligand (aptamer). In one embodiment of any one of the methods provided herein, the agent of RNAi is double-stranded RNA, single-stranded RNA, micro RNA, short interfering RNA, short hairpin RNA or a triplex-forming oligonucleotide.

In one embodiment of any one of the methods provided herein, the antigen-presenting cell targeted immunosuppressant comprises an erythrocyte-binding therapeutic. In one embodiment of any one of the methods provided herein, the erythrocyte-binding therapeutic comprises ERY1, ERY19, ERY59, ERY64, ERY123, ERY141 and ERY162. In one embodiment of any one of the methods provided herein, the erythrocyte-binding therapeutic further comprises a viral transfer vector antigen. In one embodiment of any one of the methods provided herein, the viral transfer vector antigen is a viral antigen.

In one embodiment of any one of the methods provided herein, the antigen-presenting cell targeted immunosuppressant comprises a negatively-charged particle. In one embodiment of any one of the methods provided herein, the negatively-charged particle is a polystyrene, PLGA, or diamond particle. In one embodiment of any one of the methods provided herein, the zeta potential of the particle is negative. In one embodiment of any one of the methods provided herein, the zeta potential of the particle is less than −50 mV. In one embodiment of any one of the methods provided herein, the zeta potential of the particle is less than −100 mV.

In one embodiment of any one of the methods provided herein, the antigen-presenting cell targeted immunosuppressant comprises an apoptotic-body mimic and one or more viral transfer vector antigens. In one embodiment of any one of the methods provided herein, the apoptotic-body mimic is a particle that comprises the one or more viral transfer vector antigens. In one embodiment of any one of the methods provided herein, the one or more viral transfer vector antigens comprise one or more viral antigens. In one embodiment of any one of the methods provided herein, the particle may also comprise an apoptotic signaling molecule. In one embodiment of any one of the methods provided herein, the particle comprises a polyglycolic acid polymer (PGA), polylactic acid polymer (PLA), polysebacic acid polymer (PSA), poly(lactic-co-glycolic) acid copolymer (PLGA), poly(lactic-co-sebacic) acid copolymer (PLSA), poly(glycolic-co-sebacic) acid copolymer (PGSA), polylactide co-glycolide (PLG), or polyethylene glycol (PEG). In one embodiment of any one of the methods provided herein, the average diameter of the particle is between 0.1 and 5 μm, between 0.1 and 4 μm, between 0.1 and 3 μm, between 0.1 and 2 μm, between 0.1 and 1 μm or between 0.1 and 500 nm.

In one embodiment of any one of the methods provided herein, the antigen-presenting cell targeted immunosuppressant comprises synthetic nanocarriers comprising an immunosuppressant. In one embodiment of any one of the methods provided herein, the synthetic nanocarriers further comprise a viral transfer vector antigen. In one embodiment of any one of the methods provided herein, the viral transfer vector antigen is a viral antigen. In one embodiment of any one of the methods provided herein, the immunosuppressant and/or the antigen, if present, are/is encapsulated in the synthetic nanocarriers.

In one embodiment of any one of the methods provided herein, the synthetic nanocarriers comprise lipid nanoparticles, polymeric nanoparticles, metallic nanoparticles, surfactant-based emulsions, dendrimers, buckyballs, nanowires, virus-like particles or peptide or protein particles. In one embodiment of any one of the methods provided herein, the synthetic nanocarriers comprise polymeric nanoparticles. In one embodiment of any one of the methods provided herein, the polymeric nanoparticles comprise a polymer that is a non-methoxy-terminated, pluronic polymer. In one embodiment of any one of the methods provided herein, the polymeric nanoparticles comprise a polyester, polyester attached to a polyether, polyamino acid, polycarbonate, polyacetal, polyketal, polysaccharide, polyethyloxazoline or polyethyleneimine. In one embodiment of any one of the methods provided herein, the polyester comprises a poly(lactic acid), poly(glycolic acid), poly(lactic-co-glycolic acid) or polycaprolactone. In one embodiment of any one of the methods provided herein, the polymeric nanoparticles comprise a polyester and a polyester attached to a polyether. In one embodiment of any one of the methods provided herein, the polyether comprises polyethylene glycol or polypropylene glycol.

In one embodiment of any one of the methods provided herein, the mean of a particle size distribution obtained using dynamic light scattering of a population of the synthetic nanocarriers is a diameter greater than 110 nm. In one embodiment of any one of the methods provided herein, the diameter is greater than 150 nm. In one embodiment of any one of the methods provided herein, the diameter is greater than 200 nm. In one embodiment of any one of the methods provided herein, the diameter is greater than 250 nm. In one embodiment of any one of the methods provided herein, the diameter is less than 5 μm. In one embodiment of any one of the methods provided herein, the diameter is less than 4 μm. In one embodiment of any one of the methods provided herein, the diameter is less than 3 μm. In one embodiment of any one of the methods provided herein, the diameter is less than 2 μm. In one embodiment of any one of the methods provided herein, the diameter is less than 1 μm. In one embodiment of any one of the methods provided herein, the diameter is less than 500 nm. In one embodiment of any one of the methods provided herein, the diameter is less than 450 nm. In one embodiment of any one of the methods provided herein, the diameter is less than 400 nm. In one embodiment of any one of the methods provided herein, the diameter is less than 350 nm. In one embodiment of any one of the methods provided herein, the diameter is less than 300 nm.

In one embodiment of any one of the methods provided herein, the load of immunosuppressant comprised in the synthetic nanocarriers, on average across the synthetic nanocarriers, is between 0.1% and 50% (weight/weight). In one embodiment of any one of the methods provided herein, the load is between 0.1% and 25%. In one embodiment of any one of the methods provided herein, the load is between 1% and 25%. In one embodiment of any one of the methods provided herein, the load is between 2% and 25%.

In one embodiment of any one of the methods provided herein, the immunosuppressant is an inhibitor of the NF-kB pathway. In one embodiment of any one of the methods provided herein, the immunosuppressant is rapamycin.

In one embodiment of any one of the methods provided herein, an aspect ratio of a population of the synthetic nanocarriers is greater than 1:1, 1:1.2, 1:1.5, 1:2, 1:3, 1:5, 1:7 or 1:10.

In one embodiment of any one of the methods provided herein, the method further comprises performing the method according to a protocol that attenuates an anti-viral transfer vector response, such as an antibody, T cell or B cell response, escalates transgene expression or that establishes an anti-viral transfer vector response. In one embodiment of any one of the methods provided herein, the method further comprises determining a protocol that attenuates an anti-viral transfer vector response, such as an antibody, T cell or B cell response, escalates transgene expression or that establishes an anti-viral transfer vector response.

In another embodiment of any one of the methods provided, the method further comprises assessing an antibody immune response against the viral transfer vector prior to, during or subsequent to the administering to the subject.

In another aspect a method or composition as described in any one of the Examples is provided.

In another aspect, any one of the compositions is for use in any one of the methods provided.

In another aspect, any one of the methods is for use in treating any one of the disease or disorders described herein. In another aspect, any one of the methods is for use in attenuating an anti-viral transfer vector response, establishing an attenuated anti-viral transfer vector response, escalating transgene expression or for repeated administration of a viral transfer vector.

DETAILED DESCRIPTION OF THE INVENTION

Figure 1:
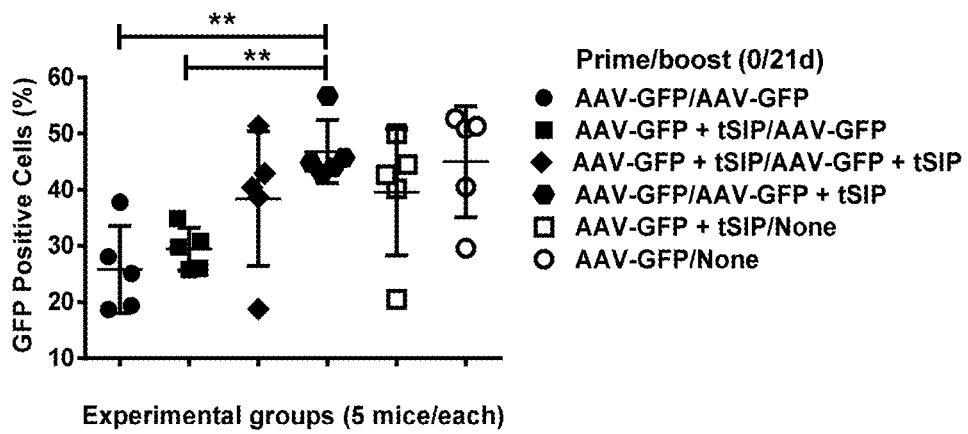
FIG. 1. shows GFP expression in livers of mice injected with AAV with or without synthetic nanocarriers comprising rapamycin at prime or boost. All cells in suspension have been analyzed for GFP expression with the exception of high side-scatter debris (2-3% of total, a by-product of collagenase treatment) excluded by the first 'clean' gate. All the remaining cells were gated for relative GFP strength (FL-1 channel). Numbers shown represent the percentage of GFP-positive cells of the total parent population.

Before describing the present invention in detail, it is to be understood that this invention is not limited to particularly exemplified materials or process parameters as such may, of course, vary. It is also to be understood that the terminology used herein is for the purpose of describing particular embodiments of the invention only, and is not intended to be limiting of the use of alternative terminology to describe the present invention.

All publications, patents and patent applications cited herein, whether supra or infra, are hereby incorporated by reference in their entirety for all purposes. Such incorporation by reference is not intended to be an admission that any of the incorporated publications, patents and patent applications cited herein constitute prior art.

As used in this specification and the appended claims, the singular forms "a," "an" and "the" include plural referents unless the content clearly dictates otherwise. For example, reference to "a polymer" includes a mixture of two or more such molecules or a mixture of differing molecular weights of a single polymer species, reference to "a synthetic nanocarrier" includes a mixture of two or more such synthetic nanocarriers or a plurality of such synthetic nanocarriers, reference to "a DNA molecule" includes a mixture of two or more such DNA molecules or a plurality of such DNA molecules, reference to "an immunosuppressant" includes a mixture of two or more such immunosuppressant molecules or a plurality of such immunosuppressant molecules, and the like.

As used herein, the term "comprise" or variations thereof such as "comprises" or "comprising" are to be read to indicate the inclusion of any recited integer (e.g. a feature, element, characteristic, property, method/process step or limitation) or group of integers (e.g. features, elements, characteristics, properties, method/process steps or limitations) but not the exclusion of any other integer or group of integers. Thus, as used herein, the term "comprising" is inclusive and does not exclude additional, unrecited integers or method/process steps.

In embodiments of any of the compositions and methods provided herein, "comprising" may be replaced with "consisting essentially of" or "consisting of". The phrase "consisting essentially of" is used herein to require the specified integer(s) or steps as well as those which do not materially affect the character or function of the claimed invention. As used herein, the term "consisting" is used to indicate the presence of the recited integer (e.g. a feature, element, characteristic, property, method/process step or limitation) or group of integers (e.g. features, elements, characteristics, properties, method/process steps or limitations) alone.

A. Introduction

Anti-viral transfer vectors are promising therapeutics for a variety of applications such as gene expression modulation. Viral transfer vectors, therefore, may comprise transgenes that encode proteins or nucleic acids. Examples of such include microRNA (miRNA), small interfering RNA (siRNA), as well as antisense oligonucleotides that bind mutation sites in messenger RNA (such as small nuclear RNA (snRNA)). Unfortunately, the promise of these therapeutics has not yet been realized in the art in a large part due to cellular and humoral immune responses against the viral transfer vector. These immune responses include antibody, B cell and T cell responses and can be specific to viral antigens of the viral transfer vector, such as viral capsid or coat proteins or peptides thereof.

Currently, many possible patients harbor some level of pre-existing immunity against the viruses on which viral transfer vectors are based. In fact, antibodies against viral antigens, such as antibodies against adeno-associated viruses, are highly prevalent in the human population. In addition, even if the level of pre-existing immunity is low, for example due to the low immunogenicity of the viral transfer vector, such low levels may still prevent successful transduction (e.g., Jeune, et al., Human Gene Therapy Methods, 24:59-67 (2013)). Thus, even low levels of pre-existing immunity may hinder the use of a specific viral transfer vector and may require a clinician to choose a viral transfer vector based on a virus of a different serotype, that may not be as efficacious, or even opt for a different type of therapy if another viral transfer vector therapy is not available.

Additionally, viral vectors, such as adeno-associated vectors, can be highly immunogenic and elicit humoral and cell-mediated immunity that can compromise efficacy, particularly with respect to re-administration. In fact, cellular and humoral immune responses against a viral transfer vector can develop after a single administration of the viral transfer vector. After viral transfer vector administration, neutralizing antibody titers can increase and remain high for several years and can reduce the effectiveness of readministration of the viral transfer vector, as repeated administration of a viral transfer vector generally results in enhanced undesired immune responses. In addition, viral transfer vector-specific CD8+ T cells may arise that eliminate transduced cells expressing a desired transgene product, such as, for example, on reexposure to a viral antigen, such as a capsid protein. Indeed, it has been shown that AAV capsid antigen triggered immune-mediated destruction of hepatocytes transduced with an AAV viral transfer vector (e.g., Manno et al., Nature Medicine, Vol. 12, No. 3, 2006). For many therapeutic applications, it is anticipated that multiple rounds of administration of viral transfer vectors will be needed for long-term benefits, and, without the methods and compositions provided herein, the ability to do so would be expected to be severely limited particularly if readministration is needed.

The problems associated with the use of viral transfer vectors for therapy is further compounded because viral transfer vector antigens can persist for some time, such as for at least several weeks, after a single administration (e.g., Nathawani et al., N Engl J Med 365; 25, 2011; Nathwani, et al., N Engl J Med 371; 21, 2014). As an example, it has been found that long-lasting capsid-specific humoral immunity developed in patients that received a single infusion of an adeno-associated virus serotype 8 (AAV8) viral transfer vector (e.g., Nathwani, et al., N Engl J Med 371; 21, 2014). The persistence of antigen further hinders the ability to use viral transfer vectors successfully. It is important to evade immune responses against viral transfer vectors in order for therapy with viral transfer vectors to be successful. Prior to this invention, however, there was no way to do so and achieve long-term immune response attenuation without the need for long-term administration of an immunosuppressant.

The inventors have surprisingly and unexpectedly discovered that the problems and limitations noted above can be overcome by practicing the invention disclosed herein. Methods and compositions are provided that offer solutions to the aforementioned obstacles to effective use of viral transfer vectors for treatment. In particular, it has been unexpectedly discovered that anti-viral transfer vector immune responses can be attenuated with the methods and related compositions provided herein. The methods and compositions can increase the efficacy of treatment with viral transfer vectors and provide for long-term immune attenuation even if the administration of the viral transfer vector need be repeated.

The invention will now be described in more detail below.

B. Definitions

"Administering" or "administration" or "administer" means giving or dispensing a material to a subject in a manner that is pharmacologically useful. The term is intended to include "causing to be administered". "Causing to be administered" means causing, urging, encouraging, aiding, inducing or directing, directly or indirectly, another party to administer the material. Any one of the methods provided herein may comprise or further comprise a step of administering concomitantly an antigen-presenting cell targeted immunosuppressant and a viral transfer vector. In some embodiments, the concomitant administration is performed repeatedly. In still further embodiments, the concomitant administration is simultaneous administration.

"Amount effective" in the context of a composition or dosage form for administration to a subject as provided herein refers to an amount of the composition or dosage form that produces one or more desired results in the subject, for example, the reduction or elimination of an immune response against a viral transfer vector or the generation of an anti-viral transfer vector attenuated response. The amount effective can be for in vitro or in vivo purposes. For in vivo purposes, the amount can be one that a clinician would believe may have a clinical benefit for a subject that may experience undesired immune responses as a result of administration of a viral transfer vector. In any one of the methods provided herein, the composition(s) administered may be in any one of the amounts effective as provided herein.

Amounts effective can involve reducing the level of an undesired immune response, although in some embodiments, it involves preventing an undesired immune response altogether. Amounts effective can also involve delaying the occurrence of an undesired immune response. An amount effective can also be an amount that results in a desired therapeutic endpoint or a desired therapeutic result. Amounts effective, preferably, result in a tolerogenic immune response in a subject to an antigen, such as a viral transfer vector antigen. Amounts effective, can also preferably result in increased transgene expression (the transgene being delivered by the viral transfer vector). This can be determined by measuring transgene protein concentrations in various tissues or systems of interest in the subject. This increased expression may be measured locally or systemically. The achievement of any of the foregoing can be monitored by routine methods.

In some embodiments of any one of the compositions and methods provided, the amount effective is one in which the desired immune response, such as the reduction or elimination of an immune response against a viral transfer vector or the generation of an anti-viral transfer vector attenuated response, persists in the subject for at least 1 week, at least 2 weeks or at least 1 month. In other embodiments of any one of the compositions and methods provided, the amount effective is one which produces a measurable desired immune response, such as the reduction or elimination of an immune response against a viral transfer vector or the generation of an anti-viral transfer vector attenuated response. In some embodiments, the amount effective is one that produces a measurable desired immune response (e.g., to a specific viral transfer vector antigen), for at least 1 week, at least 2 weeks or at least 1 month.

Amounts effective will depend, of course, on the particular subject being treated; the severity of a condition, disease or disorder; the individual patient parameters including age, physical condition, size and weight; the duration of the treatment; the nature of concurrent therapy (if any); the specific route of administration and like factors within the knowledge and expertise of the health practitioner. These factors are well known to those of ordinary skill in the art and can be addressed with no more than routine experimentation.

"Anti-viral transfer vector immune response" or "immune response against a viral transfer vector" or the like refers to any undesired immune response against a viral transfer vector. In some embodiments, the undesired immune response is an antigen-specific immune response against the viral transfer vector or an antigen thereof. In some embodiments, the immune response is specific to a viral antigen of the viral transfer vector. In other embodiments, the immune response is specific to a protein or peptide encoded by the transgene of the viral transfer vector. In some embodiments, the immune response is specific to a viral antigen of the viral transfer vector and not to a protein or peptide that is encoded by the transgene of the viral transfer vector. The immune response may be an anti-viral transfer vector antibody response, an anti-viral transfer vector T cell immune response, such as a CD4+ T cell or CD8+ T cell immune response, or an anti-viral transfer vector B cell immune response.

An anti-viral transfer vector immune response is said to be an "anti-viral transfer vector attenuated response" when it is in some manner reduced or eliminated in the subject or as compared to an expected or measured response in the subject or another subject. In some embodiments, the anti-viral transfer vector attenuated response in a subject comprises a reduced anti-viral transfer vector immune response (such as a T cell, B cell or antibody response) measured using a biological sample obtained from the subject following a concomitant administration as provided herein as compared to an anti-viral transfer vector immune response measured using a biological sample obtained from another subject, such as a test subject, following administration to this other subject of the viral transfer vector without concomitant administration of the antigen-presenting cell targeted immunosuppressant. In some embodiments, the biological sample is obtained from the other subject following administration to this other subject of the viral transfer vector without any administration of the antigen-presenting cell targeted immunosuppressant. In some embodiments, the anti-viral transfer vector attenuated response is a reduced anti-viral transfer vector immune response (such as a T cell, B cell or antibody response) in a biological sample obtained from the subject following a concomitant administration as provided herein upon a subsequent viral transfer vector in vitro challenge performed on the subject's biological sample as compared to the anti-viral transfer vector immune response detected upon viral transfer vector in vitro challenge performed on a biological sample obtained from another subject, such as a test subject, following administration to this other subject of the viral transfer vector without concomitant administration of the antigen-presenting cell targeted immunosuppressant. In some embodiments, the anti-viral transfer vector attenuated response is a reduced anti-viral transfer vector immune response (such as a T cell, B cell or antibody response) in the subject following a concomitant administration as provided herein upon a subsequent viral transfer vector challenge administered to the subject as compared to the anti-viral transfer vector immune response in another subject, such as a test subject, upon a viral transfer vector challenge administered to this other subject following administration to this other subject of the viral transfer vector without concomitant administration of the antigen-presenting cell targeted immunosuppressant. In some embodiments, the viral transfer vector is administered without any administration of the antigen-presenting cell targeted immunosuppressant.

"Antigen" means a B cell antigen or T cell antigen. "Type(s) of antigens" means molecules that share the same, or substantially the same, antigenic characteristics. In some embodiments, antigens may be proteins, polypeptides, peptides, lipoproteins, glycolipids, polynucleotides, polysaccharides, etc.

"Antigen-presenting cell targeted immunosuppressant" means an agent that results in antigen-presenting cells (APCs) having a tolerogenic effect. Such an immunosuppressant can include immunosuppressants coupled to a carrier that results in delivery to APCs and a tolerogenic effect as well as agents that by virtue of their form or characteristics can result in APC tolerogenic effects. Examples of antigen-presenting cell targeted immunosuppressants include, but are not limited to synthetic nanocarriers that comprise an immunosuppressant as described herein; immunosuppressants, as described herein, coupled to antibodies or antigen-binding fragments thereof that target APCs (or other ligand that targets an APC), erythrocyte-binding therapeutics, as well as particles that by virtue of their characteristics lead to APC tolerogenic immune responses, etc.

When the antigen-presenting cell targeted immunosuppressant is a synthetic nanoarrier coupled to an immunosuppressant, in some embodiments, the immunosuppressant is an element that is in addition to the material that makes up the structure of the synthetic nanocarrier. For example, in one embodiment, where the synthetic nanocarrier is made up of one or more polymers, the immunosuppressant is a compound that is in addition and, in some embodiments, attached to the one or more polymers. As another example, in one embodiment, where the synthetic nanocarrier is made up of one or more lipids, the immunosuppressant is again in addition to and, in some embodiments, attached to the one or more lipids. In embodiments where the antigen-presenting cell targeted immunosuppressant is a synthetic nanoarrier coupled to an immunosuppressant, and the material of the synthetic nanocarrier also results in a tolerogenic effect, the immunosuppressant is an element present in addition to the material of the synthetic nanocarrier that results in a tolerogenic effect.

"Antigen-specific" refers to an immune response that results from the presence of an antigen of interest or that generates molecules that specifically recognize or bind the antigen of interest. Generally, while such responses are measurable against the antigen of interest, the responses are reduced or negligible in regard to other antigens. For example, where the immune response is antigen-specific antibody production, antibodies are produced that selectively bind the antigen of interest but not to other antigens. As another example, where the immune response involves the production of CD4+ or CD8+ T cells, antigen-specific CD4+ or CD8+ T cells can bind to an antigen of interest or portion thereof when presented in the context of MHC class I or II antigens, respectively, by an antigen-presenting cell (APC) or, in case of CD8+ T cells, by any other cell in which the antigen is produced (e.g., a cell infected with a virus). In the case of immune tolerance, antigen specificity refers to the selective prevention or inhibition of a specific immune response to a target antigen versus other unrelated or unassociated antigens (e.g. antigens that are temporally or spatially dislocated from the target antigen).

"Assessing an immune response" refers to any measurement or determination of the level, presence or absence, reduction, increase in, etc. of an immune response in vitro or in vivo. Such measurements or determinations may be performed on one or more samples obtained from a subject. Such assessing can be performed with any one of the methods provided herein or otherwise known in the art. The assessing may be assessing the number or percentage of antibodies or T cells, such as those specific to a viral transfer vector, such as in a sample from a subject. The assessing also may be assessing any effect related to the immune response, such as measuring the presence or absence of a cytokine, cell phenotype, etc. Any one of the methods provided herein may comprise or further comprise a step of assessing an immune response to a viral transfer vector or antigen thereof. The assessing may be done directly or indirectly. The term is intended to include actions that cause, urge, encourage, aid, induce or direct another party to assess an immune response.

"Attach" or "Attached" or "Couple" or "Coupled" (and the like) means to chemically associate one entity (for example a moiety) with another. In some embodiments, the attaching is covalent, meaning that the attachment occurs in the context of the presence of a covalent bond between the two entities. In non-covalent embodiments, the non-covalent attaching is mediated by non-covalent interactions including but not limited to charge interactions, affinity interactions, metal coordination, physical adsorption, host-guest interactions, hydrophobic interactions, TT stacking interactions, hydrogen bonding interactions, van der Waals interactions, magnetic interactions, electrostatic interactions, dipole-dipole interactions, and/or combinations thereof. In embodiments, encapsulation is a form of attaching.

"Average", as used herein, refers to the arithmetic mean unless otherwise noted.

"Concomitantly" means administering two or more materials/agents to a subject in a manner that is correlated in time, preferably sufficiently correlated in time so as to provide a modulation in an immune response, and even more preferably the two or more materials/agents are administered in combination. In embodiments, concomitant administration may encompass administration of two or more materials/agents within a specified period of time, preferably within 1 month, more preferably within 1 week, still more preferably within 1 day, and even more preferably within 1 hour. In embodiments, the materials/agents may be repeatedly administered concomitantly; that is concomitant administration on more than one occasion, such as provided in the Examples.

"Determining" means objectively ascertaining something, such as a fact, relationship or quantity. In some embodiments, whether or not a subject has a pre-existing immunity to a viral transfer vector may be determined. The term is intended to include "causing to be determined". "Causing to be determined" means causing, urging, encouraging, aiding, inducing or directing another party to perform a step of determining as provided herein. In some embodiments, the step of determining may be determining whether or not a subject has a pre-existing immunity to a viral transfer vector. Any one of the methods provided herein may comprise or further comprise a step of determining as described herein including a step of determining whether or not a subject has a pre-existing immunity to a viral transfer vector.

"Directing" means influencing, such as taking some action to influence, in some manner the actions of another party, such as causing or controlling the acts of the other party in such a manner that they perform one or more steps as provided herein. In some embodiments, the other party is an agent of the party that is doing the directing. In other embodiments, the other party is not an agent of the party that is doing the directing, but the step(s) performed by the other party is/are attributable to or the result of the directing. Accordingly, directing includes instructing or providing instructions to perform one or more steps in order to receive a benefit conditioned on the performance of the one or more steps.

"Dosage form" means a pharmacologically and/or immunologically active material in a medium, carrier, vehicle, or device suitable for administration to a subject. Any one of the compositions or doses provided herein may be in a dosage form.

"Dose" refers to a specific quantity of a pharmacologically and/or immunologically active material for administration to a subject for a given time. A "prior dose" refers to an earlier dose of a material. In general, doses of the antigen-presenting cell targeted immunosuppressants and/or viral transfer vectors in the methods and compositions of the invention refer to the amount of the antigen-presenting cell targeted immunosuppressants and/or viral transfer vectors. Alternatively, the dose can be administered based on the number of synthetic nanocarriers that provide the desired amount of antigen-presenting cell targeted immunosuppressant, in instances where the antigen-presenting cell targeted immunosuppressant is a synthetic nanocarrier that comprises an immunosuppressant. When dose is used in the context of a repeated dosing, dose refers to the amount of each of the repeated doses, which may be the same or different.

"Encapsulate" means to enclose at least a portion of a substance within a synthetic nanocarrier. In some embodiments, a substance is enclosed completely within a synthetic nanocarrier. In other embodiments, most or all of a substance that is encapsulated is not exposed to the local environment external to the synthetic nanocarrier. In other embodiments, no more than 50%, 40%, 30%, 20%, 10% or 5% (weight/weight) is exposed to the local environment. Encapsulation is distinct from absorption, which places most or all of a substance on a surface of a synthetic nanocarrier, and leaves the substance exposed to the local environment external to the synthetic nanocarrier.

"Escalating transgene expression" refers to increasing the level of the transgene expression product of a viral transfer vector in a subject, the transgene being delivered by the viral transfer vector. In some embodiments, the level of the transgene expression product may be determined by measuring transgene protein concentrations in various tissues or systems of interest in the subject. Alternatively, when the transgene expression product is a nucleic acid, the level of transgene expression may be measured by transgene nucleic acid products. Escalating transgene expression can be determined, for example, by measuring the amount of the transgene expression product in a sample obtained from a subject and comparing it to a prior sample. The sample may be a tissue sample. In some embodiments, the transgene expression product can be measured using flow cytometry.

"Establishing" or "establish" means to generate an outcome or result or to deduce something, such as a fact or relationship. Which use of this term will be apparent based on the context in which it is used. For generating an outcome or result, the establishing may be accomplished in a number of ways, including but not limited to, taking steps to accomplish the outcome or result. For example, in some embodiments, administration of material(s) as provided herein can generate the outcome or result. For determining something, such as a fact or relationship, the establishing may be accomplished by performing experiments, making projections, etc. For instance, establishing that administration of a viral transfer vector is likely to generate an anti-viral transfer vector immune response in a subject may be based on results of experiments on a subject, including on one or more samples obtained therefrom. Generally, the likelihood of generating an anti-viral transfer vector immune response in a subject is the likelihood of generating such a response with the administration (or repeated administration, in some embodiments) of a viral transfer vector in the absence of administration of an antigen-presenting cell targeted immunosuppressant as provided herein. Likewise, establishing that a subject has a pre-existing immunity to a viral transfer vector may also be based on the result of experiments on a subject, including on one or more samples obtained therefrom. In another embodiment, such establishing may be determined by assessing an immune response in the subject. In regard to establishing a dose for administration, a dose of an antigen-presenting cell targeted immunosuppressant or a viral transfer vector may be determined by starting with a test dose and using known scaling techniques (such as allometric or isometric scaling) to determine the dose for administration. Such may also be used to establish a protocol as provided herein. "Establishing" or "establish" comprises "causing to be established." "Causing to be established" means causing, urging, encouraging, aiding, inducing or directing or acting in coordination with an entity for the entity to perform a step of establishing as provided herein. In some embodiments of any one of the methods provided herein, the method may comprise or further comprise any one of the steps of establishing as described herein.

"Frequency" refers to the interval of time at which the antigen-presenting cell targeted immunosuppressant, the viral transfer vector or both in combination (such as with concomitant administration) are administered to a subject.

"Gene expression modulating transgene" refers to any nucleic acid that encodes a gene expression modulator. "Gene expression modulator" refers to a molecule that can enhance, inhibit or modulate the expression of one or more endogenous genes. Gene expression modulators, therefore, include DNA-binding proteins (e.g., artificial transcription factors) as well as molecules that mediate RNA interference. Gene expression modulators include RNAi molecules (e.g., dsRNAs or ssRNAs), miRNA, and triplex-forming oligonucleotides (TFOs). Gene expression modulators also may include modified RNAs, including modified versions of any of the foregoing RNA molecules.

"Immunosuppressant" means a compound that causes a tolerogenic effect, preferably through its effects on APCs. A tolerogenic effect generally refers to the modulation by the APC or other immune cells systemically and/or locally, that reduces, inhibits or prevents an undesired immune response to an antigen in a durable fashion. In one embodiment, the immunosuppressant is one that causes an APC to promote a regulatory phenotype in one or more immune effector cells. For example, the regulatory phenotype may be characterized by the inhibition of the production, induction, stimulation or recruitment of antigen-specific CD4+ T cells or B cells, the inhibition of the production of antigen-specific antibodies, the production, induction, stimulation or recruitment of Treg cells (e.g., CD4+CD25highFoxP3+ Treg cells), etc. This may be the result of the conversion of CD4+ T cells or B cells to a regulatory phenotype. This may also be the result of induction of FoxP3 in other immune cells, such as CD8+ T cells, macrophages and iNKT cells. In one embodiment, the immunosuppressant is one that affects the response of the APC after it processes an antigen. In another embodiment, the immunosuppressant is not one that interferes with the processing of the antigen. In a further embodiment, the immunosuppressant is not an apoptotic-signaling molecule. In another embodiment, the immunosuppressant is not a phospholipid.

Immunosuppressants include, but are not limited to, statins; mTOR inhibitors, such as rapamycin or a rapamycin analog (i.e., rapalog); TGF-β signaling agents; TGF-β receptor agonists; histone deacetylase inhibitors, such as Trichostatin A; corticosteroids; inhibitors of mitochondrial function, such as rotenone; P38 inhibitors; NF-κβ inhibitors, such as 6Bio, Dexamethasone, TCPA-1, IKK VII; adenosine receptor agonists; prostaglandin E2 agonists (PGE2), such as Misoprostol; phosphodiesterase inhibitors, such as phosphodiesterase 4 inhibitor (PDE4), such as Rolipram; proteasome inhibitors; kinase inhibitors; G-protein coupled receptor agonists; G-protein coupled receptor antagonists; glucocorticoids; retinoids; cytokine inhibitors; cytokine receptor inhibitors; cytokine receptor activators; peroxisome proliferator-activated receptor antagonists; peroxisome proliferator-activated receptor agonists; histone deacetylase inhibitors; calcineurin inhibitors; phosphatase inhibitors; PI3 KB inhibitors, such as TGX-221; autophagy inhibitors, such as 3-Methyladenine; aryl hydrocarbon receptor inhibitors; proteasome inhibitor I (PSI); and oxidized ATPs, such as P2X receptor blockers. Immunosuppressants also include IDO, vitamin D3, retinoic acid, cyclosporins, such as cyclosporine A, aryl hydrocarbon receptor inhibitors, resveratrol, azathiopurine (Aza), 6-mercaptopurine (6-MP), 6-thioguanine (6-TG), FK506, sanglifehrin A, salmeterol, mycophenolate mofetil (MMF), aspirin and other COX inhibitors, niflumic acid, estriol and triptolide. Other exemplary immunosuppressants include, but are not limited, small molecule drugs, natural products, antibodies (e.g., antibodies against CD20, CD3, CD4), biologics-based drugs, carbohydrate-based drugs, RNAi, antisense nucleic acids, aptamers, methotrexate, NSAIDs; fingolimod; natalizumab; alemtuzumab; anti-CD3; tacrolimus (FK506), abatacept, belatacept, etc. "Rapalog" refers to a molecule that is structurally related to (an analog) of rapamycin (sirolimus). Examples of rapalogs include, without limitation, temsirolimus (CCI-779), everolimus (RAD001), ridaforolimus (AP-23573), and zotarolimus (ABT-578). Additional examples of rapalogs may be found, for example, in WO Publication WO 1998/002441 and U.S. Pat. No. 8,455,510, the rapalogs of which are incorporated herein by reference in their entirety.

The immunosuppressant can be a compound that directly provides the tolerogenic effect on APCs or it can be a compound that provides the tolerogenic effect indirectly (i.e., after being processed in some way after administration). Immunosuppressants, therefore, include prodrug forms of any of the compounds provided herein. Further immunosuppressants, are known to those of skill in the art, and the invention is not limited in this respect. In embodiments, the immunosuppressant may comprise any one of the agents provided herein.

"Inducing to purchase" refers to any act that suggests to an entity to purchase an antigen-presenting cell targeted immunosuppressant, a viral transfer vector or both to achieve a beneficial effect as described herein or to perform any one of the methods provided herein. Such acts includes packaging an antigen-presenting cell targeted immunosuppressant, a viral transfer vector or both that describes the benefits of concomitant administration of an antigen-presenting cell targeted immunosuppressant and a viral transfer vector in order to attenuate an anti-viral transfer vector response, escalate transgene expression or allow for repeated administration of a viral transfer vector. Alternatively, the packaging may describe or suggest the performance of any one of the methods provided herein. Acts that induce an entity to purchase also include marketing an antigen-presenting cell targeted immunosuppressant, a viral transfer vector or an antigen-presenting cell targeted immunosuppressant and a viral transfer vector product with information describing or suggesting the use of such product for carrying out any of the beneficial effects described herein or any one of the methods provided herein. Alternatively, the marketing includes materials that describe or suggest the use of such product for attenuating an anti-viral transfer vector response, escalating transgene expression or for repeated administration of a viral transfer vector. As a further example, acts of inducing may also comprise acts of communicating information describing or suggesting any of the foregoing. The communicating is an action that can be performed in any form whether written, oral, etc. If in written form, the communicating may be performed via any medium including an electronic or a paper-based medium. Further, acts of inducing also include acts of distributing an antigen-presenting cell targeted immunosuppressant, a viral transfer vector or both. Acts of distributing include any action to make available the antigen-presenting cell targeted immunosuppressant, viral transfer vector or both to an entity with information, packaging, marketing materials, etc. that describes, instructs or communicates any of the benefits described herein or the steps of any one of the methods provided herein or the ability to attenuate an anti-viral transfer vector response, escalate transgene expression or allow for repeated administration of a viral transfer vector. Acts of distributing include selling, offering for sale, and transporting for sale (e.g., transporting to pharmacies, hospitals, etc.)

"Load", when coupled to a synthetic nanocarrier, is the amount of the immunosuppressant coupled to the synthetic nanocarrier based on the total dry recipe weight of materials in an entire synthetic nanocarrier (weight/weight). Generally, such a load is calculated as an average across a population of synthetic nanocarriers. In one embodiment, the load on average across the synthetic nanocarriers is between 0.1% and 99%. In another embodiment, the load is between 0.1% and 50%. In another embodiment, the load is between 0.1% and 20%. In a further embodiment, the load is between 0.1% and 10%. In still a further embodiment, the load is between 1% and 10%. In still a further embodiment, the load is between 7% and 20%. In yet another embodiment, the load is at least 0.1%, at least 0.2%, at least 0.3%, at least 0.4%, at least 0.5%, at least 0.6%, at least 0.7%, at least 0.8%, at least 0.9%, at least 1%, at least 2%, at least 3%, at least 4%, at least 5%, at least 6%, at least at least 7%, at least 8%, at least 9%, at least 10%, at least 11%, at least 12%, at least 13%, at least 14%, at least 15%, at least 16%, at least 17%, at least 18%, at least 19%, at least 20%, at least 25%, at least 30%, at least 40%, at least 50%, at least 60%, at least 70%, at least 80%, at least 90%, at least 95%, at least 96%, at least 97%, at least 98% or at least 99% on average across the population of synthetic nanocarriers. In yet a further embodiment, the load is 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19% or 20% on average across the population of synthetic nanocarriers. In some embodiments of the above embodiments, the load is no more than 25% on average across a population of synthetic nanocarriers. In embodiments, the load is calculated as may be described in the Examples or as otherwise known in the art. In some embodiments, when the form of the immunosuppressant is itself a particle or particle-like, such as a nanocrystalline immunosuppressant, the load of immunosuppressant is the amount of the immunosuppressant in the particles or the like (weight/weight). In such embodiments, the load can approach 97%, 98%, 99% or more.

"Maximum dimension of a synthetic nanocarrier" means the largest dimension of a nanocarrier measured along any axis of the synthetic nanocarrier. "Minimum dimension of a synthetic nanocarrier" means the smallest dimension of a synthetic nanocarrier measured along any axis of the synthetic nanocarrier. For example, for a spheroidal synthetic nanocarrier, the maximum and minimum dimension of a synthetic nanocarrier would be substantially identical, and would be the size of its diameter. Similarly, for a cuboidal synthetic nanocarrier, the minimum dimension of a synthetic nanocarrier would be the smallest of its height, width or length, while the maximum dimension of a synthetic nanocarrier would be the largest of its height, width or length. In an embodiment, a minimum dimension of at least 75%, preferably at least 80%, more preferably at least 90%, of the synthetic nanocarriers in a sample, based on the total number of synthetic nanocarriers in the sample, is equal to or greater than 100 nm. In an embodiment, a maximum dimension of at least 75%, preferably at least 80%, more preferably at least 90%, of the synthetic nanocarriers in a sample, based on the total number of synthetic nanocarriers in the sample, is equal to or less than 5 μm. Preferably, a minimum dimension of at least 75%, preferably at least 80%, more preferably at least 90%, of the synthetic nanocarriers in a sample, based on the total number of synthetic nanocarriers in the sample, is greater than 110 nm, more preferably greater than 120 nm, more preferably greater than 130 nm, and more preferably still greater than 150 nm. Aspects ratios of the maximum and minimum dimensions of synthetic nanocarriers may vary depending on the embodiment. For instance, aspect ratios of the maximum to minimum dimensions of the synthetic nanocarriers may vary from 1:1 to 1,000,000:1, preferably from 1:1 to 100,000:1, more preferably from 1:1 to 10,000:1, more preferably from 1:1 to 1000:1, still more preferably from 1:1 to 100:1, and yet more preferably from 1:1 to 10:1. Preferably, a maximum dimension of at least 75%, preferably at least 80%, more preferably at least 90%, of the synthetic nanocarriers in a sample, based on the total number of synthetic nanocarriers in the sample is equal to or less than 3 μm, more preferably equal to or less than 2 μm, more preferably equal to or less than 1 μm, more preferably equal to or less than 800 nm, more preferably equal to or less than 600 nm, and more preferably still equal to or less than 500 nm. In preferred embodiments, a minimum dimension of at least 75%, preferably at least 80%, more preferably at least 90%, of the synthetic nanocarriers in a sample, based on the total number of synthetic nanocarriers in the sample, is equal to or greater than 100 nm, more preferably equal to or greater than 120 nm, more preferably equal to or greater than 130 nm, more preferably equal to or greater than 140 nm, and more preferably still equal to or greater than 150 nm. Measurement of synthetic nanocarrier dimensions (e.g., effective diameter) may be obtained, in some embodiments, by suspending the synthetic nanocarriers in a liquid (usually aqueous) media and using dynamic light scattering (DLS) (e.g. using a Brookhaven ZetaPALS instrument). For example, a suspension of synthetic nanocarriers can be diluted from an aqueous buffer into purified water to achieve a final synthetic nanocarrier suspension concentration of approximately 0.01 to 0.1 mg/mL. The diluted suspension may be prepared directly inside, or transferred to, a suitable cuvette for DLS analysis. The cuvette may then be placed in the DLS, allowed to equilibrate to the controlled temperature, and then scanned for sufficient time to acquire a stable and reproducible distribution based on appropriate inputs for viscosity of the medium and refractive indicies of the sample. The effective diameter, or mean of the distribution, is then reported. Determining the effective sizes of high aspect ratio, or non-spheroidal, synthetic nanocarriers may require augmentative techniques, such as electron microscopy, to obtain more accurate measurements. "Dimension" or "size" or "diameter" of synthetic nanocarriers means the mean of a particle size distribution, for example, obtained using dynamic light scattering.

"Measurable level" refers to any level that is above a negative control level or would be considered to be above background or signal noise. A measurable level is one that would be considered to be a level indicating the presence of the molecule being measured.

"Non-methoxy-terminated polymer" means a polymer that has at least one terminus that ends with a moiety other than methoxy. In some embodiments, the polymer has at least two termini that ends with a moiety other than methoxy. In other embodiments, the polymer has no termini that ends with methoxy. "Non-methoxy-terminated, pluronic polymer" means a polymer other than a linear pluronic polymer with methoxy at both termini. Polymeric nanoparticles as provided herein can comprise non-methoxy-terminated polymers or non-methoxy-terminated, pluronic polymers.

"Obtaining" means an act of acquiring a material(s) by any means. The material may be acquired by producing it, purchasing it, receiving it, etc. This term is intended to include "causing to obtain". "Causing to obtain" means causing, urging, encouraging, aiding, inducing or directing or acting in coordination with an entity for the entity to obtain a material(s) as provided herein. In some embodiments of any one of the methods provided herein, the method may comprise or further comprise any one of the steps of obtaining as described herein.

"Pharmaceutically acceptable excipient" or "pharmaceutically acceptable carrier" means a pharmacologically inactive material used together with a pharmacologically active material to formulate the compositions. Pharmaceutically acceptable excipients comprise a variety of materials known in the art, including but not limited to saccharides (such as glucose, lactose, and the like), preservatives such as antimicrobial agents, reconstitution aids, colorants, saline (such as phosphate buffered saline), and buffers.

"Pre-existing immunity against the viral transfer vector" refers to the presence of antibodies, T cells and/or B cells in a subject, which cells have been previously primed by prior exposure to antigens of the viral transfer vector or to crossreactive antigens, including but not limited to other viruses. In some embodiments, this pre-existing immunity is at a level that is expected to result in anti-viral transfer vector immune response(s) that interferes with the efficacy of the viral transfer vector. In some embodiments, this pre-existing immunity is at a level that is expected to result in anti-viral transfer vector immune response(s) upon subsequent exposure to the viral transfer vector. Pre-existing immunity can be assessed by determining the level of antibodies, such as neutralizing antibodies, against a viral transfer vector present in a sample, such as a blood sample, from the subject. Assays for assessing the level of antibodies, such as neutralizing antibodies, are described herein at least in the Examples and are also known to those of ordinary skill in the art. Such an assay is an ELISA assay. Pre-existing immunity can also be assessed by determining antigen recall responses of immune cells, such as B or T cells, stimulated in vivo or in vitro with viral transfer vector antigens presented by APCs or viral antigen epitopes presented on MHC class I or MHC class II molecules. Assays for antigen-specific recall responses include, but are not limited to, ELISpot, intracellular cytokine staining, cell proliferation, and cytokine production assays. Generally, these and other assays are known to those of ordinary skill in the art. In some embodiments, a subject that does not exhibit pre-existing immunity against the viral transfer vector is one with a level of anti-viral transfer vector antibodies, such as neutralizing antibodies, or memory B or T cells that would be considered to be negative. In other embodiments, a subject that does not exhibit pre-existing immunity against the viral transfer vector is one with a level of an anti-viral transfer vector response that is no more than 3 standard deviations above a mean negative control.

"Producing" refers to any action that results in a material being made. An act of producing includes preparing the material or processing it in some manner. In some embodiments, an act of producing includes any act that makes that material available for use by another. This term is intended to include "causing to produce". "Causing to produce" means causing, urging, encouraging, aiding, inducing or directing or acting in coordination with an entity for the entity to make a material(s) as provided herein. In some embodiments of any one of the methods provided herein, the method may comprise or further comprise any one of the steps of producing as described herein.

"Protocol" means a pattern of administering to a subject and includes any dosing regimen of one or more substances to a subject. Protocols are made up of elements (or variables); thus a protocol comprises one or more elements. Such elements of the protocol can comprise dosing amounts (doses), dosing frequency, routes of administration, dosing duration, dosing rates, interval between dosing, combinations of any of the foregoing, and the like. In some embodiments, a protocol may be used to administer one or more compositions of the invention to one or more test subjects. Immune responses in these test subjects can then be assessed to determine whether or not the protocol was effective in generating a desired or desired level of an immune response or therapeutic effect. Any therapeutic and/or immunologic effect may be assessed. One or more of the elements of a protocol may have been previously demonstrated in test subjects, such as non-human subjects, and then translated into human protocols. For example, dosing amounts demonstrated in non-human subjects can be scaled as an element of a human protocol using established techniques such as alimetric scaling or other scaling methods. Whether or not a protocol had a desired effect can be determined using any of the methods provided herein or otherwise known in the art. For example, a sample may be obtained from a subject to which a composition provided herein has been administered according to a specific protocol in order to determine whether or not specific immune cells, cytokines, antibodies, etc. were reduced, generated, activated, etc. An exemplary protocol is one previously demonstrated to result in a tolerogenic immune response against a viral transfer vector antigen or to achieve any one of the beneficial results described herein. Useful methods for detecting the presence and/or number of immune cells include, but are not limited to, flow cytometric methods (e.g., FACS), ELISpot, proliferation responses, cytokine production, and immunohistochemistry methods. Antibodies and other binding agents for specific staining of immune cell markers, are commercially available. Such kits typically include staining reagents for antigens that allow for FACS-based detection, separation and/or quantitation of a desired cell population from a heterogeneous population of cells. In embodiments, a composition as provided herein is administered to a subject using one or more or all or substantially all of the elements of which a protocol is comprised, provided the selected element(s) are expected to achieve the desired result in the subject. Such expectation may be based on protocols determined in test subjects and scaling if needed. Any one of the methods provided herein may comprise or further comprise a step of administering a dose of the antigen-presenting cell targeted immunosuppressant alone or in combination as described herein with one or more doses of a viral transfer vector according to a protocol that has been shown to attenuate an anti-viral transfer vector immune response or allow for the repeated administration of a viral transfer vector. Any one of the method provided herein may comprise or further comprise determining such a protocol that achieves any one of the beneficial results described herein.

"Providing" means an action or set of actions that an individual performs that supplies a material for practicing the invention. Providing may include acts of producing, distributing, selling, giving, making available, prescribing or administering the material. The action or set of actions may be taken either directly oneself or indirectly. Thus, this term is intended to include "causing to provide". "Causing to provide" means causing, urging, encouraging, aiding, inducing or directing or acting in coordination with an entity for the entity to supply a material for practicing of the present invention. In some embodiments of any one of the methods provided herein, the method may comprise or further comprise any one of the steps of providing as described herein.

"Repeat dose" or "repeat dosing" or the like means at least one additional dose or dosing that is administered to a subject subsequent to an earlier dose or dosing of the same material. For example, a repeated dose of a viral transfer vector is at least one additional dose of the viral transfer vector after a prior dose of the same material. While the material may be the same, the amount of the material in the repeated dose may be different from the earlier dose. For example, in an embodiment of any one of the methods or compositions provided herein, the amount of the viral transfer vector in the repeated dose may be less than the amount of the viral transfer vector of the earlier dose. Alternatively, in an embodiment of any one of the methods or compositions provided herein, the repeated dose may be in an amount that is at least equal to the amount of the viral transfer vector in the earlier dose. A repeat dose may be administered weeks, months or years after the prior dose. In some embodiments of any one of the methods provided herein, the repeat dose or dosing is administered at least 1 week after the dose or dosing that occurred just prior to the repeat dose or dosing. Repeat dosing is considered to be efficacious if it results in a beneficial effect for the subject. Preferably, efficacious repeat dosing results in a beneficial effect in conjunction with an attenuated anti-viral transfer vector response.

"Selecting the doses of the viral transfer vector to be less than" refers to the selection of the doses of the viral transfer vector that is less than the amount of the viral transfer vector that would be selected for administration to the subject if the subject were to develop an anti-viral transfer vector immune response to the viral transfer vector due to the repeated dosing of the viral transfer vector. This term is intended to include "causing to select". "Causing to select" means causing, urging, encouraging, aiding, inducing or directing or acting in coordination with an entity for the entity to select the aforementioned lesser dosing. In some embodiments of any one of the methods provided herein, the method may comprise or further comprise any one of the steps of selecting as described herein.

"Simultaneous" means administration at the same time or substantially at the same time where a clinician would consider any time between administrations virtually nil or negligible as to the impact on the desired therapeutic outcome. In some embodiments, simultaneous means that the administrations occur with 5, 4, 3, 2, 1 or fewer minutes.

"Subject" means animals, including warm blooded mammals such as humans and primates; avians; domestic household or farm animals such as cats, dogs, sheep, goats, cattle, horses and pigs; laboratory animals such as mice, rats and guinea pigs; fish; reptiles; zoo and wild animals; and the like. As used herein, a subject may be in one need of any one of the methods or compositions provided herein.

"Synthetic nanocarrier(s)" means a discrete object that is not found in nature, and that possesses at least one dimension that is less than or equal to 5 microns in size. Albumin nanoparticles are generally included as synthetic nanocarriers, however in certain embodiments the synthetic nanocarriers do not comprise albumin nanoparticles. In embodiments, synthetic nanocarriers do not comprise chitosan. In other embodiments, synthetic nanocarriers are not lipid-based nanoparticles. In further embodiments, synthetic nanocarriers do not comprise a phospholipid.

A synthetic nanocarrier can be, but is not limited to, one or a plurality of lipid-based nanoparticles (also referred to herein as lipid nanoparticles, i.e., nanoparticles where the majority of the material that makes up their structure are lipids), polymeric nanoparticles, metallic nanoparticles, surfactant-based emulsions, dendrimers, buckyballs, nanowires, virus-like particles (i.e., particles that are primarily made up of viral structural proteins but that are not infectious or have low infectivity), peptide or protein-based particles (also referred to herein as protein particles, i.e., particles where the majority of the material that makes up their structure are peptides or proteins) (such as albumin nanoparticles) and/or nanoparticles that are developed using a combination of nanomaterials such as lipid-polymer nanoparticles. Synthetic nanocarriers may be a variety of different shapes, including but not limited to spheroidal, cuboidal, pyramidal, oblong, cylindrical, toroidal, and the like. Synthetic nanocarriers according to the invention comprise one or more surfaces. Exemplary synthetic nanocarriers that can be adapted for use in the practice of the present invention comprise: (1) the biodegradable nanoparticles disclosed in U.S. Pat. No. 5,543,158 to Gref et al., (2) the polymeric nanoparticles of Published US Patent Application 20060002852 to Saltzman et al., (3) the lithographically constructed nanoparticles of Published US Patent Application 20090028910 to DeSimone et al., (4) the disclosure of WO 2009/051837 to von Andrian et al., (5) the nanoparticles disclosed in Published US Patent Application 2008/0145441 to Penades et al., (6) the protein nanoparticles disclosed in Published US Patent Application 20090226525 to de los Rios et al., (7) the virus-like particles disclosed in published US Patent Application 20060222652 to Sebbel et al., (8) the nucleic acid attached virus-like particles disclosed in published US Patent Application 20060251677 to Bachmann et al., (9) the virus-like particles disclosed in WO2010047839A1 or WO2009106999A2, (10) the nanoprecipitated nanoparticles disclosed in P. Paolicelli et al., "Surface-modified PLGA-based Nanoparticles that can Efficiently Associate and Deliver Virus-like Particles" Nanomedicine. 5(6):843-853 (2010), (11) apoptotic cells, apoptotic bodies or the synthetic or semisynthetic mimics disclosed in U.S. Publication 2002/0086049, or (12) those of Look et al., Nanogel-based delivery of mycophenolic acid ameliorates systemic lupus erythematosus in mice" J. Clinical Investigation 123(4):1741-1749(2013).

Synthetic nanocarriers according to the invention that have a minimum dimension of equal to or less than about 100 nm, preferably equal to or less than 100 nm, do not comprise a surface with hydroxyl groups that activate complement or alternatively comprise a surface that consists essentially of moieties that are not hydroxyl groups that activate complement. In a preferred embodiment, synthetic nanocarriers according to the invention that have a minimum dimension of equal to or less than about 100 nm, preferably equal to or less than 100 nm, do not comprise a surface that substantially activates complement or alternatively comprise a surface that consists essentially of moieties that do not substantially activate complement. In a more preferred embodiment, synthetic nanocarriers according to the invention that have a minimum dimension of equal to or less than about 100 nm, preferably equal to or less than 100 nm, do not comprise a surface that activates complement or alternatively comprise a surface that consists essentially of moieties that do not activate complement. In embodiments, synthetic nanocarriers exclude virus-like particles. In embodiments, synthetic nanocarriers may possess an aspect ratio greater than 1:1, 1:1.2, 1:1.5, 1:2, 1:3, 1:5, 1:7, or greater than 1:10.

"Therapeutic protein" means any protein that may be used for a therapeutic purpose. The therapeutic protein may be one used for protein replacement or protein supplementation. Therapeutic proteins include, but are not limited to, enzymes, enzyme cofactors, hormones, blood clotting factors, cytokines, growth factors, etc. Examples of other therapeutic proteins are provided elsewhere herein.

"Transgene of the viral transfer vector" refers to the nucleic acid material the viral transfer vector is used to transport into a cell and, once in the cell, is expressed to produce a protein or nucleic acid molecule, respectively, such as for a therapeutic application as described herein. The transgene may be a gene expression modulating transgene. "Expressed" or "expression" or the like refers to the synthesis of a functional (i.e., physiologically active for the desired purpose) gene product after the transgene is transduced into a cell and processed by the transduced cell. Such a gene product is also referred to herein as a "transgene expression product". The expressed products are, therefore, the resultant protein or nucleic acid, such as an antisense oligonucleotide or a therapeutic RNA, encoded by the transgene.

"Viral transfer vector" means a viral vector that has been adapted to deliver a transgene as provided herein. "Viral vector" refers to all of the viral components of a viral transfer vector that delivers a transgene. Accordingly, "viral antigen" refers to an antigen of the viral components of the viral transfer vector, such as a capsid or coat protein, but not to the transgene or to the product it encodes. "Viral transfer vector antigen" refers to any antigen of the viral transfer vector including its viral components as well as a protein transgene expression product. Viral vectors are engineered to transduce one or more desired nucleic acids into a cell. The transgene may be a gene expression modulating transgene. In some embodiments, the transgene is one that encodes a protein provided herein, such as a therapeutic protein, a DNA-binding protein, etc. In other embodiments, the transgene is one that encodes an antisense nucleic acid, snRNA, an RNAi molecule (e.g., dsRNAs or ssRNAs), miRNA, or triplex-forming oligonucleotides (TFOs), etc. Viral vectors can be based on, without limitation, retroviruses (e.g., murine retrovirus, avian retrovirus, Moloney murine leukemia virus (MoMuLV), Harvey murine sarcoma virus (HaMuSV), murine mammary tumor virus (MuMTV), gibbon ape leukemia virus (GaLV) and Rous Sarcoma Virus (RSV)), lentiviruses, herpes viruses, adenoviruses, adeno-associated viruses, alphaviruses, etc. Other examples are provided elsewhere herein or are known in the art. The viral vectors may be based on natural variants, strains, or serotypes of viruses, such as any one of those provided herein. The viral vectors may also be based on viruses selected through molecular evolution. The viral vectors may also be engineered vectors, recombinant vectors, mutant vectors, or hybrid vectors. In some embodiments, the viral vector is a "chimeric viral vector". In such embodiments, this means that the viral vector is made up of viral components that are derived from more than one virus or viral vector.

C. Compositions for Use in the Inventive Methods

As mentioned above, cellular and humoral immune responses against the viral transfer vector can adversely effect the efficacy of viral transfer vector therapeutics and can also interfere with their readministration, making long-term treatment impossible for many patients. As evidenced in the art, treatment with viral transfer vectors would not be expected to be successful for some patients due to prior exposure to a virus on which the viral transfer is based. In addition, even if a patient did not have a pre-existing immunity against a viral transfer vector, a single administration of the viral transfer vector is likely to result in cellular and humoral immune responses, such as neutralizing antibody titers and/or the activation of memory T cells, that would not allow for successful readministration. Further compounding these issues is the long-term persistence of viral transfer vector antigens.

Importantly, the methods and compositions provided herein have been found to overcome the aforementioned obstacles by attenuating immune responses against viral transfer vectors. The methods and compositions provided herein have also been found to allow for the readministration of viral transfer vectors and provide for long-lasting tolerance against the viral transfer vector without the need for long-term immunosuppression. Accordingly, the methods and compositions provided herein are useful for the treatment of subjects with a viral transfer vector. Viral transfer vectors can be used to deliver transgenes for a variety of purposes, including for gene expression modulation, the methods and compositions provided herein are also so applicable.

Subjects

The subject as provided herein may be one with any one of the diseases or disorders as provided herein, and the transgene is one that encodes a gene expression modulator that may be used to control expression of any one of the proteins as provided herein. The protein may be an extracellular, intracellular or membrane-bound protein. In some embodiments, the subject has a disease or disorder whereby the subject's endogenous version of the protein is defective or produced in limited amounts or not at all, and the gene expression modulator can control expression of such a protein. Thus, the gene expression modulator can, in some embodiments, control the expression of any one of the proteins as provided herein, or an endogenous version thereof (such as an endogenous version of a therapeutic protein as provided herein).

Examples of therapeutic proteins include, but are not limited to, infusible or injectable therapeutic proteins, enzymes, enzyme cofactors, hormones, blood or blood coagulation factors, cytokines and interferons, growth factors, adipokines, etc.

Examples of infusible or injectable therapeutic proteins include, for example, Tocilizumab (Roche/Actemra®), alpha-1 antitryp sin (Kamada/AAT), Hematide® (Affymax and Takeda, synthetic peptide), albinterferon alfa-2b (Novartis/Zalbin™), Rhucin® (Pharming Group, C1 inhibitor replacement therapy), tesamorelin (Theratechnologies/Egrifta, synthetic growth hormone-releasing factor), ocrelizumab (Genentech, Roche and Biogen), belimumab (GlaxoSmithKline/Benlysta®), pegloticase (Savient Pharmaceuticals/Krystexxa™), taliglucerase alfa (Protalix/Uplyso), agalsidase alfa (Shire/Replagal®), and velaglucerase alfa (Shire).

Examples of enzymes include lysozyme, oxidoreductases, transferases, hydrolases, lyases, isomerases, asparaginases, uricases, glycosidases, proteases, nucleases, collagenases, hyaluronidases, heparinases, heparanases, kinases, phosphatases, lysins and ligases. Other examples of enzymes include those that used for enzyme replacement therapy including, but not limited to, imiglucerase (e.g., CEREZYME™), a-galactosidase A (a-gal A) (e.g., agalsidase beta, FABRYZYME™), acid a-glucosidase (GAA) (e.g., alglucosidase alfa, LUMIZYME™, MYOZYME™), and arylsulfatase B (e.g., laronidase, ALDURAZYME™, idursulfase, ELAPRASE™, arylsulfatase B, NAGLAZYME™).

Examples of hormones include Melatonin (N-acetyl-5-methoxytryptamine), Serotonin, Thyroxine (or tetraiodothyronine) (a thyroid hormone), Triiodothyronine (a thyroid hormone), Epinephrine (or adrenaline), Norepinephrine (or noradrenaline), Dopamine (or prolactin inhibiting hormone), Antimullerian hormone (or mullerian inhibiting factor or hormone), Adiponectin, Adrenocorticotropic hormone (or corticotropin), Angiotensinogen and angiotensin, Antidiuretic hormone (or vasopressin, arginine vasopressin), Atrial-natriuretic peptide (or atriopeptin), Calcitonin, Cholecystokinin, Corticotropin-releasing hormone, Erythropoietin, Follicle-stimulating hormone, Gastrin, Ghrelin, Glucagon, Glucagon-like peptide (GLP-1), GIP, Gonadotropin-releasing hormone, Growth hormone-releasing hormone, Human chorionic gonadotropin, Human placental lactogen, Growth hormone, Inhibin, Insulin, Insulin-like growth factor (or somatomedin), Leptin, Luteinizing hormone, Melanocyte stimulating hormone, Orexin, Oxytocin, Parathyroid hormone, Prolactin, Relaxin, Secretin, Somatostatin, Thrombopoietin, Thyroid-stimulating hormone (or thyrotropin), Thyrotropin-releasing hormone, Cortisol, Aldosterone, Testosterone, Dehydroepiandrosterone, Androstenedione, Dihydrotestosterone, Estradiol, Estrone, Estriol, Progesterone, Calcitriol (1,25-dihydroxyvitamin D3), Calcidiol (25-hydroxyvitamin D3), Prostaglandins, Leukotrienes, Prostacyclin, Thromboxane, Prolactin releasing hormone, Lipotropin, Brain natriuretic peptide, Neuropeptide Y, Histamine, Endothelin, Pancreatic polypeptide, Renin, and Enkephalin.

Examples of blood or blood coagulation factors include Factor I (fibrinogen), Factor II (prothrombin), tissue factor, Factor V (proaccelerin, labile factor), Factor VII (stable factor, proconvertin), Factor VIII (antihemophilic globulin), Factor IX (Christmas factor or plasma thromboplastin component), Factor X (Stuart-Prower factor), Factor Xa, Factor XI, Factor XII (Hageman factor), Factor XIII (fibrin-stabilizing factor), von Willebrand factor, von Heldebrant Factor, prekallikrein (Fletcher factor), high-molecular weight kininogen (HMWK) (Fitzgerald factor), fibronectin, fibrin, thrombin, antithrombin, such as antithrombin III, heparin cofactor II, protein C, protein S, protein Z, protein Z-related protease inhibitot (ZPI), plasminogen, alpha 2-antiplasmin, tissue plasminogen activator (tPA), urokinase, plasminogen activator inhibitor-1 (PAI1), plasminogen activator inhibitor-2 (PAI2), cancer procoagulant, and epoetin alfa (Epogen, Procrit).

Examples of cytokines include lymphokines, interleukins, and chemokines, type 1 cytokines, such as IFN-γ, TGF-β, and type 2 cytokines, such as IL-4, IL-10, and IL-13.

Examples of growth factors include Adrenomedullin (AM), Angiopoietin (Ang), Autocrine motility factor, Bone morphogenetic proteins (BMPs), Brain-derived neurotrophic factor (BDNF), Epidermal growth factor (EGF), Erythropoietin (EPO), Fibroblast growth factor (FGF), Glial cell line-derived neurotrophic factor (GDNF), Granulocyte colony-stimulating factor (G-CSF), Granulocyte macrophage colony-stimulating factor (GM-CSF), Growth differentiation factor-9 (GDF9), Hepatocyte growth factor (HGF), Hepatoma-derived growth factor (HDGF), Insulin-like growth factor (IGF), Migration-stimulating factor, Myostatin (GDF-8), Nerve growth factor (NGF) and other neurotrophins, Platelet-derived growth factor (PDGF), Thrombopoietin (TPO), Transforming growth factor alpha(TGF-α), Transforming growth factor beta(TGF-β), Tumour necrosis factor-alpha(TNF-α), Vascular endothelial growth factor (VEGF), Wnt Signaling Pathway, placental growth factor (P1GF), [(Foetal Bovine Somatotrophin)] (FBS), IL-1, IL-2, IL-3, IL-4, IL-5, IL-6, and IL-7.

Examples of adipokines, include leptin and adiponectin.

Additional examples of proteins include, but are not limited to, receptors, signaling proteins, cytoskeletal proteins, scaffold proteins, transcription factors, structural proteins, membrane proteins, cytosolic proteins, binding proteins, nuclear proteins, secreted proteins, golgi proteins, endoplasmic reticulum proteins, mitochondrial proteins, and vesicular proteins, etc.

Examples of diseases or disorders include, but are not limited to, lysosomal storage diseases/disorders, such as Santavuori-Haltia disease (Infantile Neuronal Ceroid Lipofuscinosis Type 1), Jansky-Bielschowsky Disease (late infantile neuronal ceroid lipofuscinosis, Type 2), Batten disease (juvenile neuronal ceroid lipofuscinosis, Type 3), Kufs disease (neuronal ceroid lipofuscinosis, Type 4), Von Gierke disease (glycogen storage disease, Type Ia), glycogen storage disease, Type Ib, Pompe disease (glycogen storage disease, Type II), Forbes or Cori disease (glycogen storage disease, Type III), mucolipidosis II (I-Cell disease), mucolipidosis III (Pseudo-Hurler polydystrophy), mucolipidosis IV (sialolipidosis), cystinosis (adult nonnephropathic type), cystinosis (infantile nephropathic type), cystinosis (juvenile or adolescent nephropathic), Salla disease/infantile sialic acid storage disorder, and saposin deficiencies; disorders of lipid and sphingolipid degradation, such as GM1 gangliosidosis (infantile, late infantile/juvenile, and adult/chronic), Tay-Sachs disease, Sandhoff disease, GM2 gangliodisosis, Ab variant, Fabry disease, Gaucher disease, Types I, II and III, metachromatic leukidystrophy, Krabbe disease (early and late onset), Neimann-Pick disease, Types A, B, C1, and C2, Farber disease, and Wolman disease (cholesteryl esther storage disease); disorders of mucopolysaccharide degradation, such as Hurler syndrome (MPSI), Scheie syndrome (MPS IS), Hurler-Scheie syndrome (MPS III/S), Hunter syndrome (MPS II), Sanfillippo A syndrome (MPS IIIA), Sanfillippo B syndrome (MPS IIIB), Sanfillippo C syndrome (MPS IIIC), Sanfillippo D syndrome (MPS IIID), Morquio A syndrome (MPS IVA), Morquio B syndrome (MPS IVB), Maroteaux-Lamy syndrome (MPS VI), and Sly syndrome (MPS VII); disorders of glycoprotein degradation, such as alpha mannosidosis, beta mannosidosis, fucosidosis, asparylglucosaminuria, mucolipidosis I (sialidosis), galactosialidosis, Schindler disease, and Schindler disease, Type II/Kanzaki disease; and leukodystrophy diseases/disorders, such as abetalipoproteinemia, neonatal adrenoleukodystrophy, Canavan disease, cerebrotendinous xanthromatosis, Pelizaeus Merzbacher disease, Tangier disease, Refum disease, infantile, and Refum disease, classic.

Additional examples of such diseases/disorders of a subject as provided herein include, but are not limited to, acid maltase deficiency (e.g., Pompe disease, glycogenosis type 2, lysosomal storage disease); carnitine deficiency; carnitine palmityl transferase deficiency; debrancher enzyme deficiency (e.g., Cori or Forbes disease, glycogenosis type 3); lactate dehydrogenase deficiency (e.g., glycogenosis type 11); myoadenylate deaminase deficiency; phosphofructokinase deficiency (e.g., Tarui disease, glycogenosis type 7); phosphogylcerate kinase deficiency (e.g., glycogenosis type 9); phosphogylcerate mutase deficiency (e.g., glycogenosis type 10); phosphorylase deficiency (e.g., McArdle disease, myophosphorylase deficiency, glycogenosis type 5); Gaucher's Disease (e.g., chromosome 1, enzyme glucocerebrosidase affected); Achondroplasia (e.g., chromosome 4, fibroblast growth factor receptor 3 affected); Huntington's Disease (e.g., chromosome 4, huntingtin); Hemochromatosis (e.g., chromosome 6, HFE protein); Cystic Fibrosis (e.g., chromosome 7, CFTR); Friedreich's Ataxia (chromosome 9, frataxin); Best Disease (chromosome 11, VMD2); Sickle Cell Disease (chromosome 11, hemoglobin); Phenylketoniuria (chromosome 12, phenylalanine hydroxylase); Marfan's Syndrome (chromosome 15, fibrillin); Myotonic Dystophy (chromosome 19, dystophia myotonica protein kinase); Adrenoleukodystrophy (x-chromosome, lignoceroyl-CoA ligase in peroxisomes); Duchene's Muscular Dystrophy (x-chromosome, dystrophin); Rett Syndrome (x-chromosome, methylCpG-binding protein 2); Leber's Hereditary Optic Neuropathy (mitochondria, respiratory proteins); Mitochondria Encephalopathy, Lactic Acidosis and Stroke (MELAS) (mitochondria, transfer RNA); and Enzyme deficiencies of the Urea Cycle.

Still additional examples of such diseases or disorders include, but are not limited to, Sickle Cell Anemia, Myotubular Myopathy, Hemophilia B, Lipoprotein lipase deficiency, Ornithine Transcarbamylase Deficiency, Crigler-Najjar Syndrome, Mucolipidosis IV, Niemann-Pick A, Sanfilippo A, Sanfilippo B, Sanfilippo C, Sanfilippo D, b-thalassaemia and Duchenne Muscular Dystrophy. Still further examples of diseases or disorders include those that are the result of defects in lipid and sphingolipid degradation, mucopolysaccharide degradation, glycoprotein degradation, leukodystrophies, etc.

It follows that therapeutic proteins also include Myophosphorylase, glucocerebrosidase, fibroblast growth factor receptor 3, huntingtin, HFE protein, CFTR, frataxin, VMD2, hemoglobin, phenylalanine hydroxylase, fibrillin, dystophia myotonica protein kinase, lignoceroyl-CoA ligase, dystrophin, methylCpG-binding protein 2, Beta hemoglobin, Myotubularin, Cathepsin A, Factor IX, Lipoprotein lipase, Beta galactosidase, Ornithine Transcarbamylase, Iduronate-2-Sulfatase, Acid-Alpha Glucosidase, UDP-glucuronosyltransferase 1-1, GlcNAc-1-phosphotransferase, GlcNAc-1-phosphotransferase, Mucolipin-1, Microsomal triglyceride transfer protein, Sphingomyelinase, Acid ceramidase, Lysosomal acid lipase, Alpha-L-iduronidase, Heparan N-sulfatase, alpha-N-acetylglucosaminidase, acetyl-CoA alpha-glucosaminide acetyltransferase, N-acetylglucosamine 6-sulfatase, N-acetylgalactosamine-6 sulfatase, Alpha-mannosidase, Alpha-galactosidase A, Cystic fibrosis conductance transmembrane regulator, and respiratory proteins.

As further examples, the gene expression modulator may control the expression of proteins associated with disorders of lipid and sphingolipid degradation (e.g., β-Galactosidase-1, β-Hexosaminidase A, β-Hexosaminidases A and B, GM2 Activator Protein, ß-Galactosidase A, Glucocerebrosidase, Glucocerebrosidase, Glucocerebrosidase, Arylsulfatase A, Galactosylceramidase, Sphingomyelinase, Sphingomyelinase, NPC1, HE1 protein (Cholesterol Trafficking Defect), Acid Ceramidase, Lysosomal Acid Lipase); disorders of mucopolysaccharide degradation (e.g., L-Iduronidase, L-Iduronidase, L-Iduronidase, Iduronate Sulfatase, Heparan N-Sulfatase, N-Acetylglucosaminidase, Acetyl-CoA-Glucosaminidase, Acetyltransferase, Acetylglucosamine-6-Sulfatase, Galactosamine-6-Sulfatase, Arylsulfatase B, Glucuronidase); disorders of glycoprotein degradation (e.g., Mannosidase, mannosidase, 1-fucosidase, Aspartylglycosaminidase, Neuraminidase, Lysosomal protective protein, Lysosomal 8-N-acetylgalactosaminidase, Lysosomal 8-N-acetylgalactosaminidase); lysosomal storage disorders (e.g., Palmitoyl-protein thioesterase, at least 4 subtypes, Lysosomal membrane protein, Unknown, Glucose-6-phosphatase, Glucose-6-phosphate translocase, Acid maltase, Debrancher enzyme amylo-1,6 glucosidase, N-acetylglucosamine-1-phosphotransferase, N-acetylglucosamine-1-phosphotransferase, Ganglioside sialidase (neuraminidase), Lysosomal cystine transport protein, Lysosomal cystine transport protein, Lysosomal cystine transport protein, Sialic acid transport protein Saposins, A, B, C, D) and leukodystrophies (e.g., Microsomal triglyceride transfer protein/apolipoprotein B, Peroxisomal membrane transfer protein, Peroxins, Aspartoacylase, Sterol-27-hydroxlase, Proteolipid protein, ABC1 transporter, Peroxisome membrane protein 3 or Peroxisome biogenesis factor 1, Phytanic acid oxidase).

The transgene of the viral transfer vectors as provided herein is a gene expression modulating transgene. Such a transgene encodes a gene expression modulator that can enhance, inhibit or modulate the expression of one or more endogenous genes. The endogenous gene may encode any one of the proteins as provided herein provided the protein is an endogenous protein of the subject. Accordingly, the subject may be one with any one of the diseases or disorders provided herein where there would be a benefit provided by gene expression modulation.

Gene expression modulators include DNA-binding proteins (e.g., artificial transcription factors, such as those of U.S. Publication No. 20140296129, the artificial transcription factors of which are incorporated herein by reference; and transcriptional silencer protein NRF of U.S. Publication No. 20030125286, the transcriptional silencer protein NRF of which is incorporated herein by reference) as well as therapeutic RNAs. Therapeutic RNAs include, but are not limited to, inhibitors of mRNA translation (antisense), agents of RNA interference (RNAi), catalytically active RNA molecules (ribozymes), transfer RNA (tRNA) and RNAs that bind proteins and other molecular ligands (aptamers). Gene expression modulators are any agents of the foregoing and include antisense nucleic acids, RNAi molecules (e.g., double-stranded RNAs (dsRNAs), single-stranded RNAs (ssRNAs), micro RNAs (miRNAs), short interfering RNAs (siRNAs), short hairpin RNAs (shRNAs)) and triplex-forming oligonucleotides (TFOs). Gene expression modulators also may include modified versions of any of the foregoing RNA molecules and, thus, include modified mRNAs, such as synthetic chemically modified RNAs.

The gene expression modulator may be an antisense nucleic acid. Antisense nucleic acids can provide for the targeted inhibition of gene expression (e.g., the expression of mutant protein, a dominantly active gene product, a protein associated with toxicity or gene products that are introduced into a cell by an infectious agent, such as a virus). Thus, gene expression modulating viral transfer vectors can be used for treating diseases or disorders associated with dominant-negative or gain-of-function pathogenetic mechanisms, cancer, or infection. The subject of any one of the methods provided herein may be a subject that has a viral infection, inflammatory disorder, cardiovascular disease, cancer, genetic disorder or autoimmune disease. Antisense nucleic acids may also interfere with mRNA splicing machinery and disrupt normal cellular mRNA processing. Accordingly, the gene expression modulating transgene may encode elements that interact with spliceosome proteins. Examples of antisense nucleic acids (and related constructs) can be found in, for example, U.S. Publication Nos. 20050020529 and 20050271733, the antisense nucleic acids and constructs of which are incorporated herein by reference.

The gene expression modulator may also be a ribozyme (i.e., a RNA molecule that can cleave other RNAs, such as single-stranded RNA). Such molecules may be engineered to recognize specific nucleotide sequences in a RNA molecule and cleave it (Cech, J. Amer. Med. Assn., 260:3030, 1988). For example, ribozymes can be engineered so that only mRNAs with sequences complementary to a construct containing the ribozyme are inactivated. Types of ribozymes and how to prepare related constructs are known in the art (Hasselhoff, et al., Nature, 334:585, 1988; and U.S. Publication No. 20050020529, the teachings of which pertaining to such ribozymes and methods are incorporated herein by reference).

The gene expression modulator may be an interfering RNA (RNAi). RNA interference refers to the process of sequence-specific post-transcriptional gene silencing mediated by interfering RNAs. Generally, the presence of dsRNA can trigger an RNAi response. RNAi has been studied in a variety of systems. Fire et al., 1998, Nature, 391, 806, RNAi in *C. elegans*; Bahramian and Zarbl, 1999, Molecular and Cellular Biology, 19, 274-283 and Wianny and Goetz, 1999, Nature Cell Biol., 2, 70, RNAi mediated by dsRNA in mammalian systems; Hammond et al., 2000, Nature, 404, 293, RNAi in *Drosophila* cells; Elbashir et al., 2001, Nature, 411, 494, RNAi induced by introduction of duplexes of synthetic 21-nucleotide RNAs in cultured mammalian cells. Such work, along with others, has provided guidance as to the length, structure, chemical composition, and sequence that are helpful in the construction of RNAi molecules in order to mediate RNAi activity. Various publications provide examples of RNAi molecules that can be used as gene expression modulators. Such publications include, U.S. Pat. Nos. 8,993,530, 8,877,917, 8,293,719, 7,947,659, 7,919,473, 7,790,878, 7,737,265, 7,592,322; and U.S. Publication Nos. 20150197746, 20140350071, 20140315835, 20130156845 and 20100267805, the teaching related to the types of RNAi molecules as well as their production are incorporated herein by reference.

Aptamers can bind various protein targets and disrupt the interactions of those proteins with other proteins. Accordingly, the gene expression modulator may be an aptamer, and the gene expression modulating transgene can encode such an aptamer. Aptamers may be selected for their ability to prevent transcription of a gene by specifically binding the DNA-binding sites of regulatory proteins. PCT Publication Nos. WO 98/29430 and WO 00/20040 provides examples of aptamers that were used to modulate gene expression; and U.S. Publication No. 20060128649 also provide examples of such aptamers, the aptamers of each of which are incorporated herein by reference.

As a further example, the gene expression modulatory may be a triplex oligomer. Such a molecule can stall transcription. Generally, this is known as the triplex strategy as the oligomer winds around double-helical DNA, forming a three-strand helix. Such molecules can be designed to recognize a unique site on a chosen gene (Maher, et al., Antisense Res. and Dev., 1(3):227, 1991; Helene, C., Anticancer Drug Design, 6(6):569, 1991).

The sequence of a transgene may also include an expression control sequence. Expression control DNA sequences include promoters, enhancers, and operators, and are generally selected based on the expression systems in which the expression construct is to be utilized. In some embodiments, promoter and enhancer sequences are selected for the ability to increase gene expression, while operator sequences may be selected for the ability to regulate gene expression. The transgene may also include sequences that facilitate, and preferably promote, homologous recombination in a host cell. The transgene may also include sequences that are necessary for replication in a host cell.

Exemplary expression control sequences include promoter sequences, e.g., cytomegalovirus promoter; Rous sarcoma virus promoter; and simian virus 40 promoter; as well as any other types of promoters that are disclosed elsewhere herein or are otherwise known in the art. Generally, promoters are operatively linked upstream (i.e., 5') of the sequence coding for a desired expression product. The transgene also may include a suitable polyadenylation sequence (e.g., the SV40 or human growth hormone gene polyadenylation sequence) operably linked downstream (i.e., 3') of the coding sequence.

Viral Vectors

Viruses have evolved specialized mechanisms to transport their genomes inside the cells that they infect; viral vectors based on such viruses can be tailored to transduce cells to specific applications. Examples of viral vectors that may be used as provided herein are known in the art or described herein. Suitable viral vectors include, for instance, retroviral vectors, lentiviral vectors, herpes simplex virus (HSV)-based vectors, adenovirus-based vectors, adeno-associated virus (AAV)-based vectors, and AAV-adenoviral chimeric vectors.

The viral transfer vectors provided herein may be based on a retrovirus. Retrovirus is a single-stranded positive sense RNA virus capable of infecting a wide variety of host cells. Upon infection, the retroviral genome integrates into the genome of its host cell, using its own reverse transcriptase enzyme to produce DNA from its RNA genome. The viral DNA is then replicated along with host cell DNA, which translates and transcribes the viral and host genes. A retroviral vector can be manipulated to render the virus replication-incompetent. As such, retroviral vectors are thought to be particularly useful for stable gene transfer in vivo. Examples of retroviral vectors can be found, for example, in U.S. Publication Nos. 20120009161, 20090118212, and 20090017543, the viral vectors and methods of their making being incorporated by reference herein in their entirety.

Lentiviral vectors are examples of retroviral vectors that can be used for the production of a viral transfer vector as provided herein. Lentiviruses have the ability to infect non-dividing cells, a property that constitute a more efficient method of a gene delivery vector (see, e.g., Durand et al., Viruses. 2011 February; 3(2): 132-159). Examples of lentiviruses include HIV (humans), simian immunodeficiency virus (SIV), feline immunodeficiency virus (FIV), equine infectious anemia virus (EIAV) and visna virus (ovine lentivirus). Unlike other retroviruses, HIV-based vectors are known to incorporate their passenger genes into non-dividing cells. Examples of lentiviral vectors can be found, for example, in U.S. Publication Nos. 20150224209, 20150203870, 20140335607, 20140248306, 20090148936, and 20080254008, the viral vectors and methods of their making being incorporated by reference herein in their entirety.

Herpes simplex virus (HSV)-based viral vectors are also suitable for use as provided herein. Many replication-deficient HSV vectors contain a deletion to remove one or more intermediate-early genes to prevent replication. Advantages of the herpes vector are its ability to enter a latent stage that can result in long-term DNA expression, and its large viral DNA genome that can accommodate exogenous DNA up to 25 kb. For a description of HSV-based vectors, see, for example, U.S. Pat. Nos. 5,837,532, 5,846,782, 5,849,572, and 5,804,413, and International Patent Applications WO 91/02788, WO 96/04394, WO 98/15637, and WO 99/06583, the description of which viral vectors and methods of their making being incorporated by reference in its entirety.

Adenoviruses (Ads) are nonenveloped viruses that can transfer DNA in vivo to a variety of different target cell types. The virus can be made replication-deficient by deleting select genes required for viral replication. The expendable non-replication-essential E3 region is also frequently deleted to allow additional room for a larger DNA insert. Viral transfer vectors can be based on adenoviruses. Adenoviral transfer vectors can be produced in high titers and can efficiently transfer DNA to replicating and non-replicating cells. Unlike lentivirus, adenoviral DNA does not integrate into the genome and therefore is not replicated during cell division, instead they replicate in the nucleus of the host cell using the host's replication machinery.

The adenovirus on which a viral transfer vector may be based may be from any origin, any subgroup, any subtype, mixture of subtypes, or any serotype. For instance, an adenovirus can be of subgroup A (e.g., serotypes 12, 18, and 31), subgroup B (e.g., serotypes 3, 7, 11, 14, 16, 21, 34, 35, and 50), subgroup C (e.g., serotypes 1, 2, 5, and 6), subgroup D (e.g., serotypes 8, 9, 10, 13, 15, 17, 19, 20, 22-30, 32, 33, 36-39, and 42-48), subgroup E (e.g., serotype 4), subgroup F (e.g., serotypes 40 and 41), an unclassified serogroup (e.g., serotypes 49 and 51), or any other adenoviral serotype. Adenoviral serotypes 1 through 51 are available from the American Type Culture Collection (ATCC, Manassas, Va.). Non-group C adenoviruses, and even non-human adenoviruses, can be used to prepare replication-deficient adenoviral vectors. Non-group C adenoviral vectors, methods of producing non-group C adenoviral vectors, and methods of using non-group C adenoviral vectors are disclosed in, for example, U.S. Pat. Nos. 5,801,030, 5,837,511, and 5,849,561, and International Patent Applications WO 97/12986 and WO 98/53087. Any adenovirus, even a chimeric adenovirus, can be used as the source of the viral genome for an adenoviral vector. For example, a human adenovirus can be used as the source of the viral genome for a replication-deficient adenoviral vector. Further examples of adenoviral vectors can be found in U.S. Publication Nos. 20150093831, 20140248305, 20120283318, 20100008889, 20090175897 and 20090088398, the description of which viral vectors and methods of their making being incorporated by reference in its entirety.

The viral transfer vectors provided herein can also be based on adeno-associated viruses (AAVs). AAV vectors have been of particular interest for use in therapeutic applications such as those described herein. AAV is a DNA virus, which is not known to cause human disease. Generally, AAV requires co-infection with a helper virus (e.g., an adenovirus or a herpes virus), or expression of helper genes, for efficient replication. AAVs have the ability to stably infect host cell genomes at specific sites, making them more predictable than retroviruses; however, generally, the cloning capacity of the vector is 4.9 kb. AAV vectors that have been used in gene therapy applications generally have had approximately 96% of the parental genome deleted, such that only the terminal repeats (ITRs), which contain recognition signals for DNA replication and packaging, remain. For a description of AAV-based vectors, see, for example, U.S. Pat. Nos. 8,679,837, 8,637,255, 8,409,842, 7,803,622, and 7,790,449, and U.S. Publication Nos. 20150065562, 20140155469, 20140037585, 20130096182, 20120100606, and 20070036757, the viral vectors of which and methods or their making being incorporated herein by reference in their entirety. The AAV vectors may be recombinant AAV vectors. The AAV vectors may also be self-complementary (sc) AAV vectors, which are described, for example, in U.S. Patent Publications 2007/01110724 and 2004/0029106, and U.S. Pat. Nos. 7,465,583 and 7,186,699, the vectors and methods of production of which are herein incorporated by reference.

The adeno-associated virus on which a viral transfer vector may be of any serotype or a mixture of serotypes. AAV serotypes include AAV1, AAV2, AAV3, AAV4, AAV5, AAV6, AAV7, AAV8, AAV9, AAV10, and AAV11. For example, when the viral transfer vector is based on a mixture of serotypes, the viral transfer vector may contain the capsid signal sequences taken from one AAV serotype (for example selected from any one of AAV serotypes 1, 2, 3, 4, 5, 6, 7, 8, 9, 10, and 11) and packaging sequences from a different serotype (for example selected from any one of AAV serotypes 1, 2, 3, 4, 5, 6, 7, 8, 9, 10, and 11). In some embodiments of any one of the methods or compositions provided herein, therefore, the AAV vector is an AAV 2/8 vector. In other embodiments of any one of the methods or compositions provided herein, the AAV vector is an AAV 2/5 vector.

The viral transfer vectors provided herein may also be based on an alphavirus. Alphaviruses include Sindbis (and VEEV) virus, Aura virus, Babanki virus, Barmah Forest virus, Bebaru virus, Cabassou virus, Chikungunya virus, Eastern equine encephalitis virus, Everglades virus, Fort Morgan virus, Getah virus, Highlands J virus, Kyzylagach virus, Mayaro virus, Me Tri virus, Middelburg virus, Mosso das Pedras virus, Mucambo virus, Ndumu virus, O'nyong-nyong virus, Pixuna virus, Rio Negro virus, Ross River virus, Salmon pancreas disease virus, Semliki Forest virus, Southern elephant seal virus, Tonate virus, Trocara virus, Una virus, Venezuelan equine encephalitis virus, Western equine encephalitis virus, and Whataroa virus. Generally, the genome of such viruses encode nonstructural (e.g., replicon) and structural proteins (e.g., capsid and envelope) that can be translated in the cytoplasm of the host cell. Ross River virus, Sindbis virus, Semliki Forest virus (SFV), and Venezuelan equine encephalitis virus (VEEV) have all been used to develop viral transfer vectors for transgene delivery. Pseudotyped viruses may be formed by combining alphaviral envelope glycoproteins and retroviral capsids. Examples of alphaviral vectors can be found in U.S. Publication Nos. 20150050243, 20090305344, and 20060177819; the vectors and methods of their making are incorporated herein by reference in their entirety.

Antigen-Presenting Cell Targeted Immunosuppressants

Antigen-presenting cell targeted immunosuppressant can include agents that by virtue of their form or characteristics can result in APC tolerogenic effects. Antigen-presenting cell targeted immunosuppressant also include agents that comprise a carrier to which an immunosuppressant is conjugated.

Antigen-presenting cell targeted immunosuppressants include negatively-charged particles, such as polystyrene, PLGA, or diamond particles of a certain size and zeta potential, such as those described in U.S. Publication No. 20150010631, the description of such particles and methods of their production being incorporated herein by reference. Such particles may have any particle shape or conformation. However, in some embodiments it is preferred to use particles that are less likely to clump in vivo. In one embodiment, these particles have a spherical shape. Generally, it is not necessary for such particles to be uniform in size, although such particles must generally be of a size sufficient to trigger phagocytosis in an antigen-presenting cell or other MPS cell. Preferably, these particles are microscopic or nanoscopic in size, in order to enhance solubility, avoid possible complications caused by aggregation in vivo and to facilitate pinocytosis.

These particles may an average diameter of from about 0.1 μm to about 10 μm, about 0.2 μm to about 2 μm, about 0.3 μm to about 5 μm, or about 0.5 μm to about 3 μm. In some embodiments, these particles may have an average diameter of about 0.1 μm, about 0.2 μm, about 0.3 μm, about 0.4 μm, about 0.5 μm, about 1.0 μm, about 1.5 μm, about 2.0 μm, about 2.5 μm, about 3.0 μm, about 3.5 μm, about 4.0 μm, about 4.5 μm, or about 5.0 μm. These particles need not be of uniform diameter, and a pharmaceutical formulation may contain a plurality of particles with a mixture of particle sizes.

In some embodiments, these particles are non-metallic. In these embodiments, these particles may be formed from a polymer. In a preferred embodiment, these particles are biodegradable. Examples of suitable particles include polystyrene particles, PLGA particles, PLURONICS stabilized polypropylene sulfide particles, and diamond particles. Additionally, these particles can be formed from a wide range of other materials. For example, these particles may be composed of glass, silica, polyesters of hydroxy carboxylic acids, polyanhydrides of dicarboxylic acids, or copolymers of hydroxy carboxylic acids and dicarboxylic acids. More generally, these particles may be composed of other materials as described in U.S. Publication No. 20150010631.

The particles generally possess a particular zeta potential. In certain embodiments, the zeta potential is negative. The zeta potential may be less than about −100 mV or less than about −50 mV. In certain embodiments, the particles possess a zeta potential between −100 mV and 0 mV, between −75 mV and 0 mV, between −60 mV and 0 mV, between −50 mV and 0 mV, between −40 mV and 0 mV, between −30 mV and 0 mV, between −20 mV and +0 mV, between −10 mV and −0 mV, between −100 mV and −50 mV, between −75 mV and −50 mV, or between −50 mV and −40 mV.

In another embodiment, these particles also comprise one or more antigens as provided herein. In some of these embodiments, the one or more antigens are encapsulated in the particles.

Another example of an antigen-presenting cell targeted immunosuppressant is an immunosuppressants in nanocrystalline form, whereby the form of the immunosuppressant itself is a particle or particle-like. In these embodiments, such forms mimic a virus or other foreign pathogen. Many drugs have been nanosized and appropriate methods for producing such drug forms would be known to one of ordinary skill in the art. Drug nanocrystals, such as nanocrystalline rapamycin, are known to those of ordinary skill in the art (Katteboinaa, et al. 2009, International Journal of PharmTech Resesarch; Vol. 1, No. 3; pp 682-694. As used herein, a "drug nanocrystal" refers to a form of a drug (e.g., an immunosuppressant) that does not include a carrier or matrix material. In some embodiments, drug nanocrystals comprise 90%, 95%, 98%, or 99% or more drug. Methods for producing drug nanocrystals include, without limitation, milling, high pressure homogenization, precipitation, spray drying, rapid expansion of supercritical solution (RESS), Nanoedge® technology (Baxter Healthcare), and Nanocrystal Technology™ (Elan Corporation). In some embodiments, a surfactant or a stabilizer may be used for steric or electrostatic stability of the drug nanocrystal. In some embodiments, the nanocrystal or nanocrytalline form of an immunosuppressant may be used to increase the solubility, stability, and/or bioavailability of the immunosuppressant, particularly immunosuppressants that are insoluble or labile.

Antigen-presenting call targeted immunosuppressants also may be an apoptotic-body mimic and cause an associated antigen(s) to be tolerized. Such mimics are described in U.S. Publication No. 20120076831, which mimics and methods of their making are incorporated herein by reference. The apoptotic-body mimics may be particles, beads, branched polymers, dendrimers, or liposomes. Preferably the mimic is particulate, and generally spherical, ellipsoidal, rod-shaped, globular, or polyhedral in shape. Alternatively, however, the mimic may be of an irregular or branched shape. In preferred embodiments, the mimic is composed of material which is biodegradable. It is further preferred that the mimic have a net neutral or negative charge, in order to reduce non-specific binding to cell surfaces which, in general, bear a net negative charge. Preferably the mimic surface is composed of a material that minimizes non-specific or unwanted biological interactions. When a particle, the mimic surface may be coated with a material to prevent or decrease non-specific interactions. Steric stabilization by coating particles with hydrophilic layers such as poly(ethylene glycol) (PEG) and its copolymers such as PLURONICS (including copolymers of poly(ethylene glycol)-bl-poly(propylene glycol)-bl-poly(ethylene glycol)) may reduce the non-specific interactions with proteins of the interstitium.

When particles, the mimics may be particles composed of glass, silica, polyesters of hydroxy carboxylic acids, polyanhydrides of dicarboxylic acids, or copolymers of hydroxy carboxylic acids and dicarboxylic acids. These mimics may be quantum dots, or composed of quantum dots, such as quantum dot polystyrene particles. These mimics may comprise materials including polyglycolic acid polymers (PGA), polylactic acid polymers (PLA), polysebacic acid polymers (PSA), poly(lactic-co-glycolic) acid copolymers (PLGA), poly(lactic-co-sebacic) acid copolymers (PLSA), poly(glycolic-co-sebacic) acid copolymers (PGSA), etc. The mimics may also be polystyrene beads.

These mimics may comprise one or more antigens. The mimics may be capable of being conjugated, either directly or indirectly, to one or more antigens to which tolerance is desired. In some instances, the mimic will have multiple binding sites in order to have multiple copies of the antigen exposed and increase the likelihood of a tolerogenic response. The mimic may have one antigen on its surface or multiple different antigens on the surface. Alternatively, however, the mimic may have a surface to which conjugating moieties may be adsorbed without chemical bond formation.

In some embodiments, the mimics may also comprise an apoptotic signaling molecule, although this is not necessarily required, such as with polystyrene beads. Apoptotic signaling molecules include, but are not limited to, the apoptosis signaling molecules described in U.S. Publication No. 20050113297, which apoptosis signaling molecules are herein incorporated by reference. Molecules suitable for use in these particles include molecules that target phagocytes, which include macrophages, dendritic cells, monocytes and neutrophils. Such molecules may be thrombospondins or Annexin I.

Antigen-presenting cell targeted immunosuppressants may also be erythrocyte-binding therapeutics, such as those described in U.S. Publication No. 20120039989, which therapeutics and methods of their making are incorporated herein by reference. As described, peptides that specifically bind to erythrocytes (also known as red blood cells) were discovered. These peptides bind specifically to erythrocytes even in the presence of other factors present in blood and can be used to create immunotolerance. Accordingly, an erythrocyte-binding therapeutic comprises one or more antigens to which tolerance is desired and an erythrocyte affinity ligand. The one or more antigens may be viral transfer vector antigens as described herein, such as one or more viral antigens (e.g., of one or more viral capsid proteins). Also, the one or more antigens may be or include one or more antigens of an expressed transgene as provided. The antigens may form a mixture to which tolerance is desired.

Examples of peptides that specifically bind erythrocytes include ERY1, ERY19, ERY59, ERY64, ERY123, ERY141 and ERY162. In addition to peptides that bind erythrocytes, proteins, such as antibodies, for example single chain antibodies, and antigen binding fragments thereof may also be used as the affinity ligands. The affinity ligands may also include nucleotide aptamer ligands for erythrocyte surface components. Accordingly, aptamers can be made and used in place of other erythrocyte affinity ligands. DNA and RNA aptamers may be used to provide non-covalent erythrocyte binding. Aptamers can be classified as DNA aptamers, RNA aptamers, or peptide aptamers. Additionally, the affinity ligands may be a fusion of two or more affinity ligands, such as erythrocyte-binding peptides. Further, the components of the erythrocyte-binding therapeutics may be associated with a carrier such as a polymersome, a liposome or micelle or some types of nanoparticles. In some embodiments, the components are encapsulated in such a carrier. In some embodiments, the carrier comprises an affinity ligand as described herein and one or more antigens. In such an embodiment, the affinity ligand and one or more antigens do not necessarily need to be conjugated to each other.

Antigen-presenting cell targeted immunosuppressants also include any one of the immunosuppressants provided herein coupled to a carrier that targets APCs. The carrier in some embodiments may be an antibody or antigen binding fragment thereof (or some other ligand) that is specific to an APC marker. Such markers include, but are not limited to, CD1a (R4, T6, HTA-1); CD1b (R1); CD1c (M241, R7); CD1d (R3); CD1e (R2); CD11b (αM Integrin chain, CR3, Mol, C3niR, Mac-1); CD11c (αX Integrin, p150, 95, AXb2); CDw117 (Lactosylceramide, LacCer); CD19 (B4); CD33 (gp67); CD 35 (CR1, C3b/C4b receptor); CD 36 (GpIIIb, GPIV, PASIV); CD39 (ATPdehydrogenase, NTPdehydrogenase-1); CD40 (Bp50); CD45 (LCA, T200, B220, Ly5); CD45RA; CD45RB; CD45RC; CD45RO (UCHL-1); CD49d (VLA-4α, α4 Integrin); CD49e (VLA-5α, α5 Integrin); CD58 (LFA-3); CD64 (FcγRI); CD72 (Ly-19.2, Ly-32.2, Lyb-2); CD73 (Ecto-5'nucloticlase); CD74 (Ii, invariant chain); CD80 (B7, B7-1, BB1); CD81 (TAPA-1); CD83 (HB15); CD85a (ILT5, LIR3, HL9); CD85d (ILT4, LIR2, MIR10); CD85j (ILT2, LIR1, MIR7); CD85k (ILT3, LIR5, HM18); CD86 (B7-2/B70); CD88 (C5aB); CD97 (BL-KDD/F12); CD101 (IGSF2, P126, V7); CD116 (GM-CSFRα); CD120a (TMFRI, p55); CD120b (TNFRII, p75, TNFR p80); CD123 (IL-3Rα); CD139; CD148 (HPTP-η, p260, DEP-1); CD150 (SLAM, IPO-3); CD156b (TACE, ADAM17, cSVP); CD157 (Mo5, BST-1); CD167a (DDR1, trkE, cak); CD168 (RHAMM, IHABP, HMMR); CD169 (Sialoadhesin, Siglec-1); CD170 (Siglec-5); CD171 (L1CAM, NILE); CD172 (SIRP-1α, MyD-1); CD172b (SIRPβ); CD180 (RP105, Bgp95, Ly64); CD184 (CXCR4, NPY3R); CD193 (CCR3); CD196 (CCR6); CD197 (CCR7 (ws CDw197)); CDw197 (CCR7, EBI1, BLR2); CD200 (OX2); CD205 (DEC-205); CD206 (MMR); CD207 (Langerin); CD208 (DC-LAMP); CD209 (DC-SIGN); CDw218a (IL18Rα); CDw218b (IL8Rβ); CD227 (MUC1, PUM, PEM, EMA); CD230 (Prion Protein (PrP)); CD252 (OX40L, TNF (ligand) superfamily, member 4); CD258 (LIGHT, TNF (ligand) superfamily, member 14); CD265 (TRANCE-R, TNF-R superfamily, member 11a); CD271 (NGFR, p75, TNFR superfamily, member 16); CD273 (B7DC, PDL2); CD274 (B7H1, PDL1); CD275 (B7H2, ICOSL); CD276 (B7H3); CD277 (BT3.1, B7 family: Butyrophilin 3); CD283 (TLR3, TOLL-like receptor 3); CD289 (TLR9, TOLL-like receptor 9); CD295 (LEPR); CD298 (ATP1B3, Na K ATPase β3 submit); CD300a (CMRF-35H); CD300c (CMRF-35A); CD301 (MGL1, CLECSF14); CD302 (DCL1); CD303 (BDCA2); CD304 (BDCA4); CD312 (EMR2); CD317 (BST2); CD319 (CRACC, SLAMF7); CD320 (8D6); and CD68 (gp110, Macrosialin); class II MHC; BDCA-1; and Siglec-H. Methods for preparing antibody-drug conjugates can be found in U.S. Publication No. 20150231241, which methods are herein incorporated by reference. Other methods are known to those in the art.

The antigen-presenting cell targeted immunosuppressant may also be synthetic nanocarriers that comprise any one of the immunosuppressants as described herein. Such synthetic nanocarriers include those of U.S. Publication No. 20100151000, the synthetic nanocarriers of which, and methods of their making, are incorporated herein by reference. As described, it was found that tolerogenic responses can be generated in vivo by administering particles (e.g., liposomes or polymeric particles) comprising both a NF-κB inhibitor and an antigen. Accordingly, particles that comprise an inhibitor of the NF-κB pathway and one or more viral transfer vector antigens can be used as antigen-presenting cell targeted immunosuppressants as provided herein. In some embodiments, the particle is liposomal. In other embodiments, the particle comprises a carrier particle, such as a metal particle (e.g., a tungsten, gold, platinum or iridium particle). In still other embodiments, the particle comprises a polymeric matrix or carrier, illustrative examples of which include biocompatible polymeric particles (e.g., particles fabricated with poly(lactide-co-glycolide)). In still other embodiments, the particle comprises a ceramic or inorganic matrix or carrier.

The inhibitor of the NF-κB pathway can decrease the level or functional activity of a member of the NF-κB pathway, and can be selected from BTK, LYN, BCR Ig.alpha., BCR Ig.beta., Syk, Blnk, PLC.gamma.2, PKC.beta., DAG, CARMA1, BCL10, MALT1, PI3K, PIPS, AKT, p38 MAPK, ERK, COT, IKK.alpha., IKK.beta., IKK.gamma., NIK, RelA/p65, P105/p50, c-Rel, ReIB, p52, NIK, Leu13, CD81, CD19, CD21 and its ligands in the complement and coagulation cascade, TRAF6, ubiquitin ligase, Tab2, TAK1, NEMO, NOD2, RIP2, Lck, fyn, Zap70, LAT, GRB2, SOS, CD3 zeta, Slp-76, GADS, ITK, PLC.gamma.1, PKC.theta., ICOS, CD28, SHP2, SAP, SLAM and 2B4. In some embodiments, the NF-κB pathway inhibitor decreases the level or functional activity of any one or more of RelA/p65, P105/p50, c-Rel, RelB or p52.

A wide variety of other synthetic nanocarriers can be used according to the invention, and in some embodiments, coupled to an immunosuppressant to provide still other antigen-presenting cell targeted immunosuppressants. In some embodiments, synthetic nanocarriers are spheres or spheroids. In some embodiments, synthetic nanocarriers are flat or plate-shaped. In some embodiments, synthetic nanocarriers are cubes or cubic. In some embodiments, synthetic nanocarriers are ovals or ellipses. In some embodiments, synthetic nanocarriers are cylinders, cones, or pyramids.

In some embodiments, it is desirable to use a population of synthetic nanocarriers that is relatively uniform in terms of size or shape so that each synthetic nanocarrier has similar properties. For example, at least 80%, at least 90%, or at least 95% of the synthetic nanocarriers of any one of the compositions or methods provided, based on the total number of synthetic nanocarriers, may have a minimum dimension or maximum dimension that falls within 5%, 10%, or 20% of the average diameter or average dimension of the synthetic nanocarriers.

Synthetic nanocarriers can be solid or hollow and can comprise one or more layers. In some embodiments, each layer has a unique composition and unique properties relative to the other layer(s). To give but one example, synthetic nanocarriers may have a core/shell structure, wherein the core is one layer (e.g. a polymeric core) and the shell is a second layer (e.g. a lipid bilayer or monolayer). Synthetic nanocarriers may comprise a plurality of different layers.

In some embodiments, synthetic nanocarriers may optionally comprise one or more lipids. In some embodiments, a synthetic nanocarrier may comprise a liposome. In some embodiments, a synthetic nanocarrier may comprise a lipid bilayer. In some embodiments, a synthetic nanocarrier may comprise a lipid monolayer. In some embodiments, a synthetic nanocarrier may comprise a micelle. In some embodiments, a synthetic nanocarrier may comprise a core comprising a polymeric matrix surrounded by a lipid layer (e.g., lipid bilayer, lipid monolayer, etc.). In some embodiments, a synthetic nanocarrier may comprise a non-polymeric core (e.g., metal particle, quantum dot, ceramic particle, bone particle, viral particle, proteins, nucleic acids, carbohydrates, etc.) surrounded by a lipid layer (e.g., lipid bilayer, lipid monolayer, etc.).

In other embodiments, synthetic nanocarriers may comprise metal particles, quantum dots, ceramic particles, etc. In some embodiments, a non-polymeric synthetic nanocarrier is an aggregate of non-polymeric components, such as an aggregate of metal atoms (e.g., gold atoms).

In some embodiments, synthetic nanocarriers may optionally comprise one or more amphiphilic entities. In some embodiments, an amphiphilic entity can promote the production of synthetic nanocarriers with increased stability, improved uniformity, or increased viscosity. In some embodiments, amphiphilic entities can be associated with the interior surface of a lipid membrane (e.g., lipid bilayer, lipid monolayer, etc.). Many amphiphilic entities known in the art are suitable for use in making synthetic nanocarriers in accordance with the present invention. Such amphiphilic entities include, but are not limited to, phosphoglycerides; phosphatidylcholines; dipalmitoyl phosphatidylcholine (DPPC); dioleylphosphatidyl ethanolamine (DOPE); dioleyloxypropyltriethylammonium (DOTMA); dioleoylphosphatidylcholine; cholesterol; cholesterol ester; diacylglycerol; diacylglycerolsuccinate; diphosphatidyl glycerol (DPPG); hexanedecanol; fatty alcohols such as polyethylene glycol (PEG); polyoxyethylene-9-lauryl ether; a surface active fatty acid, such as palmitic acid or oleic acid; fatty acids; fatty acid monoglycerides; fatty acid diglycerides; fatty acid amides; sorbitan trioleate (Span®85) glycocholate; sorbitan monolaurate (Span®20); polysorbate 20 (Tween®20); polysorbate 60 (Tween®60); polysorbate 65 (Tween®65); polysorbate 80 (Tween®80); polysorbate 85 (Tween®85); polyoxyethylene monostearate; surfactin; a poloxomer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebrosides; dicetylphosphate; dipalmitoylphosphatidylglycerol; stearylamine; dodecylamine; hexadecyl-amine; acetyl palmitate; glycerol ricinoleate; hexadecyl sterate; isopropyl myristate; tyloxapol; poly(ethylene glycol)5000-phosphatidylethanolamine; poly(ethylene glycol)400-monostearate; phospholipids; synthetic and/or natural detergents having high surfactant properties; deoxycholates; cyclodextrins; chaotropic salts; ion pairing agents; and combinations thereof. An amphiphilic entity component may be a mixture of different amphiphilic entities. Those skilled in the art will recognize that this is an exemplary, not comprehensive, list of substances with surfactant activity. Any amphiphilic entity may be used in the production of synthetic nanocarriers to be used in accordance with the present invention.

In some embodiments, synthetic nanocarriers may optionally comprise one or more carbohydrates. Carbohydrates may be natural or synthetic. A carbohydrate may be a derivatized natural carbohydrate. In certain embodiments, a carbohydrate comprises monosaccharide or disaccharide, including but not limited to glucose, fructose, galactose, ribose, lactose, sucrose, maltose, trehalose, cellbiose, mannose, xylose, arabinose, glucoronic acid, galactoronic acid, mannuronic acid, glucosamine, galatosamine, and neuramic acid. In certain embodiments, a carbohydrate is a polysaccharide, including but not limited to pullulan, cellulose, microcrystalline cellulose, hydroxypropyl methylcellulose (HPMC), hydroxycellulose (HC), methylcellulose (MC), dextran, cyclodextran, glycogen, hydroxyethylstarch, carageenan, glycon, amylose, chitosan, N,O-carboxylmethylchitosan, algin and alginic acid, starch, chitin, inulin, konjac, glucommannan, pustulan, heparin, hyaluronic acid, curdlan, and xanthan. In embodiments, the synthetic nanocarriers do not comprise (or specifically exclude) carbohydrates, such as a polysaccharide. In certain embodiments, the carbohydrate may comprise a carbohydrate derivative such as a sugar alcohol, including but not limited to mannitol, sorbitol, xylitol, erythritol, maltitol, and lactitol.

In some embodiments, synthetic nanocarriers can comprise one or more polymers. In some embodiments, the synthetic nanocarriers comprise one or more polymers that is a non-methoxy-terminated, pluronic polymer. In some embodiments, at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 97%, or 99% (weight/weight) of the polymers that make up the synthetic nanocarriers are non-methoxy-terminated, pluronic polymers. In some embodiments, all of the polymers that make up the synthetic nanocarriers are non-methoxy-terminated, pluronic polymers. In some embodiments, the synthetic nanocarriers comprise one or more polymers that is a non-methoxy-terminated polymer. In some embodiments, at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 97%, or 99% (weight/weight) of the polymers that make up the synthetic nanocarriers are non-methoxy-terminated polymers. In some embodiments, all of the polymers that make up the synthetic nanocarriers are non-methoxy-terminated polymers. In some embodiments, the synthetic nanocarriers comprise one or more polymers that do not comprise pluronic polymer. In some embodiments, at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 97%, or 99% (weight/weight) of the polymers that make up the synthetic nanocarriers do not comprise pluronic polymer. In some embodiments, all of the polymers that make up the synthetic nanocarriers do not comprise pluronic polymer. In some embodiments, such a polymer can be surrounded by a coating layer (e.g., liposome, lipid monolayer, micelle, etc.). In some embodiments, elements of the synthetic nanocarriers can be attached to the polymer.

Immunosuppressants can be coupled to the synthetic nanocarriers by any of a number of methods. Generally, the attaching can be a result of bonding between the immunosuppressants and the synthetic nanocarriers. This bonding can result in the immunosuppressants being attached to the surface of the synthetic nanocarriers and/or contained (encapsulated) within the synthetic nanocarriers. In some embodiments, however, the immunosuppressants are encapsulated by the synthetic nanocarriers as a result of the structure of the synthetic nanocarriers rather than bonding to the synthetic nanocarriers. In preferable embodiments, the synthetic nanocarrier comprises a polymer as provided herein, and the immunosuppressants are attached to the polymer.

When attaching occurs as a result of bonding between the immunosuppressants and synthetic nanocarriers, the attaching may occur via a coupling moiety. A coupling moiety can be any moiety through which an immunosuppressant is bonded to a synthetic nanocarrier. Such moieties include covalent bonds, such as an amide bond or ester bond, as well as separate molecules that bond (covalently or non-covalently) the immunosuppressant to the synthetic nanocarrier. Such molecules include linkers or polymers or a unit thereof. For example, the coupling moiety can comprise a charged polymer to which an immunosuppressant electrostatically binds. As another example, the coupling moiety can comprise a polymer or unit thereof to which it is covalently bonded.

In preferred embodiments, the synthetic nanocarriers comprise a polymer as provided herein. These synthetic nanocarriers can be completely polymeric or they can be a mix of polymers and other materials.

In some embodiments, the polymers of a synthetic nanocarrier associate to form a polymeric matrix. In some of these embodiments, a component, such as an immunosuppressant, can be covalently associated with one or more polymers of the polymeric matrix. In some embodiments, covalent association is mediated by a linker. In some embodiments, a component can be noncovalently associated with one or more polymers of the polymeric matrix. For example, in some embodiments, a component can be encapsulated within, surrounded by, and/or dispersed throughout a polymeric matrix. Alternatively or additionally, a component can be associated with one or more polymers of a polymeric matrix by hydrophobic interactions, charge interactions, van der Waals forces, etc. A wide variety of polymers and methods for forming polymeric matrices therefrom are known conventionally.

Polymers may be natural or unnatural (synthetic) polymers. Polymers may be homopolymers or copolymers comprising two or more monomers. In terms of sequence, copolymers may be random, block, or comprise a combination of random and block sequences. Typically, polymers in accordance with the present invention are organic polymers.

In some embodiments, the polymer comprises a polyester, polycarbonate, polyamide, or polyether, or unit thereof. In other embodiments, the polymer comprises poly(ethylene glycol) (PEG), polypropylene glycol, poly(lactic acid), poly (glycolic acid), poly(lactic-co-glycolic acid), or a polycaprolactone, or unit thereof. In some embodiments, it is preferred that the polymer is biodegradable. Therefore, in these embodiments, it is preferred that if the polymer comprises a polyether, such as poly(ethylene glycol) or polypropylene glycol or unit thereof, the polymer comprises a block-copolymer of a polyether and a biodegradable polymer such that the polymer is biodegradable. In other embodiments, the polymer does not solely comprise a polyether or unit thereof, such as poly(ethylene glycol) or polypropylene glycol or unit thereof.

Other examples of polymers suitable for use in the present invention include, but are not limited to polyethylenes, polycarbonates (e.g. poly(1,3-dioxan-2one)), polyanhydrides (e.g. poly(sebacic anhydride)), polypropylfumerates, polyamides (e.g. polycaprolactam), polyacetals, polyethers, polyesters (e.g., polylactide, polyglycolide, polylactide-co-glycolide, polycaprolactone, polyhydroxyacid (e.g. poly(β-hydroxyalkanoate))), poly(orthoesters), polycyanoacrylates, polyvinyl alcohols, polyurethanes, polyphosphazenes, polyacrylates, polymethacrylates, polyureas, polystyrenes, and polyamines, polylysine, polylysine-PEG copolymers, and poly(ethyleneimine), poly(ethylene imine)-PEG copolymers.

In some embodiments, polymers in accordance with the present invention include polymers which have been approved for use in humans by the U.S. Food and Drug Administration (FDA) under 21 C.F.R. § 177.2600, including but not limited to polyesters (e.g., polylactic acid, poly(lactic-co-glycolic acid), polycaprolactone, polyvalerolactone, poly(1,3-dioxan-2one)); polyanhydrides (e.g., poly (sebacic anhydride)); polyethers (e.g., polyethylene glycol); polyurethanes; polymethacrylates; polyacrylates; and polycyanoacrylates.

In some embodiments, polymers can be hydrophilic. For example, polymers may comprise anionic groups (e.g., phosphate group, sulphate group, carboxylate group); cationic groups (e.g., quaternary amine group); or polar groups (e.g., hydroxyl group, thiol group, amine group). In some embodiments, a synthetic nanocarrier comprising a hydrophilic polymeric matrix generates a hydrophilic environment within the synthetic nanocarrier. In some embodiments, polymers can be hydrophobic. In some embodiments, a synthetic nanocarrier comprising a hydrophobic polymeric matrix generates a hydrophobic environment within the synthetic nanocarrier. Selection of the hydrophilicity or hydrophobicity of the polymer may have an impact on the nature of materials that are incorporated within the synthetic nanocarrier.

In some embodiments, polymers may be modified with one or more moieties and/or functional groups. A variety of moieties or functional groups can be used in accordance with the present invention. In some embodiments, polymers may be modified with polyethylene glycol (PEG), with a carbohydrate, and/or with acyclic polyacetals derived from polysaccharides (Papisov, 2001, ACS Symposium Series, 786:301). Certain embodiments may be made using the general teachings of U.S. Pat. No. 5,543,158 to Gref et al., or WO publication WO2009/051837 by Von Andrian et al.

In some embodiments, polymers may be modified with a lipid or fatty acid group. In some embodiments, a fatty acid group may be one or more of butyric, caproic, caprylic, capric, lauric, myristic, palmitic, stearic, arachidic, behenic, or lignoceric acid. In some embodiments, a fatty acid group may be one or more of palmitoleic, oleic, vaccenic, linoleic, alpha-linoleic, gamma-linoleic, arachidonic, gadoleic, arachidonic, eicosapentaenoic, docosahexaenoic, or erucic acid.

In some embodiments, polymers may be polyesters, including copolymers comprising lactic acid and glycolic acid units, such as poly(lactic acid-co-glycolic acid) and poly(lactide-co-glycolide), collectively referred to herein as "PLGA"; and homopolymers comprising glycolic acid units, referred to herein as "PGA," and lactic acid units, such as poly-L-lactic acid, poly-D-lactic acid, poly-D,L-lactic acid, poly-L-lactide, poly-D-lactide, and poly-D,L-lactide, collectively referred to herein as "PLA." In some embodiments, exemplary polyesters include, for example, polyhydroxyacids; PEG copolymers and copolymers of lactide and glycolide (e.g., PLA-PEG copolymers, PGA-PEG copolymers, PLGA-PEG copolymers, and derivatives thereof. In some embodiments, polyesters include, for example, poly(caprolactone), poly(caprolactone)-PEG copolymers, poly(L-lactide-co-L-lysine), poly(serine ester), poly(4-hydroxy-L-proline ester), poly[α-(4-aminobutyl)-L-glycolic acid], and derivatives thereof.

In some embodiments, a polymer may be PLGA. PLGA is a biocompatible and biodegradable co-polymer of lactic acid and glycolic acid, and various forms of PLGA are characterized by the ratio of lactic acid:glycolic acid. Lactic acid can be L-lactic acid, D-lactic acid, or D,L-lactic acid. The degradation rate of PLGA can be adjusted by altering the lactic acid:glycolic acid ratio. In some embodiments, PLGA to be used in accordance with the present invention is characterized by a lactic acid:glycolic acid ratio of approximately 85:15, approximately 75:25, approximately 60:40, approximately 50:50, approximately 40:60, approximately 25:75, or approximately 15:85.

In some embodiments, polymers may be one or more acrylic polymers. In certain embodiments, acrylic polymers include, for example, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid anhydride), methyl methacrylate, polymethacrylate, poly(methyl methacrylate) copolymer, polyacrylamide, aminoalkyl methacrylate copolymer, glycidyl methacrylate copolymers, polycyanoacrylates, and combinations comprising one or more of the foregoing polymers. The acrylic polymer may comprise fully-polymerized copolymers of acrylic and methacrylic acid esters with a low content of quaternary ammonium groups.

In some embodiments, polymers can be cationic polymers. In general, cationic polymers are able to condense and/or protect negatively charged strands of nucleic acids. Amine-containing polymers such as poly(lysine) (Zauner et al., 1998, Adv. Drug Del. Rev., 30:97; and Kabanov et al., 1995, Bioconjugate Chem., 6:7), poly(ethylene imine) (PEI; Boussif et al., 1995, Proc. Natl. Acad. Sci., USA, 1995, 92:7297), and poly(amidoamine) dendrimers (Kukowska-Latallo et al., 1996, Proc. Natl. Acad. Sci., USA, 93:4897; Tang et al., 1996, Bioconjugate Chem., 7:703; and Haensler et al., 1993, Bioconjugate Chem., 4:372) are positively-charged at physiological pH, form ion pairs with nucleic acids. In embodiments, the synthetic nanocarriers may not comprise (or may exclude) cationic polymers.

In some embodiments, polymers can be degradable polyesters bearing cationic side chains (Putnam et al., 1999, Macromolecules, 32:3658; Barrera et al., 1993, J. Am. Chem. Soc., 115:11010; Kwon et al., 1989, Macromolecules, 22:3250; Lim et al., 1999, J. Am. Chem. Soc., 121:5633; and Zhou et al., 1990, Macromolecules, 23:3399). Examples of these polyesters include poly(L-lactide-co-L-lysine) (Barrera et al., 1993, J. Am. Chem. Soc., 115:11010), poly(serine ester) (Zhou et al., 1990, Macromolecules, 23:3399), poly(4-hydroxy-L-proline ester) (Putnam et al., 1999, Macromolecules, 32:3658; and Lim et al., 1999, J. Am. Chem. Soc., 121:5633), and poly(4-hydroxy-L-proline ester) (Putnam et al., 1999, Macromolecules, 32:3658; and Lim et al., 1999, J. Am. Chem. Soc., 121:5633).

The properties of these and other polymers and methods for preparing them are well known in the art (see, for example, U.S. Pat. Nos. 6,123,727; 5,804,178; 5,770,417; 5,736,372; 5,716,404; 6,095,148; 5,837,752; 5,902,599; 5,696,175; 5,514,378; 5,512,600; 5,399,665; 5,019,379; 5,010,167; 4,806,621; 4,638,045; and 4,946,929; Wang et al., 2001, J. Am. Chem. Soc., 123:9480; Lim et al., 2001, J. Am. Chem. Soc., 123:2460; Langer, 2000, Acc. Chem. Res., 33:94; Langer, 1999, J. Control. Release, 62:7; and Uhrich et al., 1999, Chem. Rev., 99:3181). More generally, a variety of methods for synthesizing certain suitable polymers are described in Concise Encyclopedia of Polymer Science and Polymeric Amines and Ammonium Salts, Ed. by Goethals, Pergamon Press, 1980; Principles of Polymerization by Odian, John Wiley & Sons, Fourth Edition, 2004; Contemporary Polymer Chemistry by Allcock et al., Prentice-Hall, 1981; Deming et al., 1997, Nature, 390:386; and in U.S. Pat. Nos. 6,506,577, 6,632,922, 6,686,446, and 6,818,732.

In some embodiments, polymers can be linear or branched polymers. In some embodiments, polymers can be dendrimers. In some embodiments, polymers can be substantially cross-linked to one another. In some embodiments, polymers can be substantially free of cross-links. In some embodiments, polymers can be used in accordance with the present invention without undergoing a cross-linking step. It is further to be understood that the synthetic nanocarriers may comprise block copolymers, graft copolymers, blends, mixtures, and/or adducts of any of the foregoing and other polymers. Those skilled in the art will recognize that the polymers listed herein represent an exemplary, not comprehensive, list of polymers that can be of use in accordance with the present invention.

In some embodiments, synthetic nanocarriers do not comprise a polymeric component. In some embodiments, synthetic nanocarriers may comprise metal particles, quantum dots, ceramic particles, etc. In some embodiments, a non-polymeric synthetic nanocarrier is an aggregate of non-polymeric components, such as an aggregate of metal atoms (e.g., gold atoms).

Any immunosuppressant as provided herein can be, in some embodiments, coupled to synthetic nanocarriers, antibodies or antigen-binding fragments thereof (or other ligand that targets an APC), erythrocyte-binding peptides, etc. Immunosuppressants include, but are not limited to, statins; mTOR inhibitors, such as rapamycin or a rapamycin analog; TGF-β signaling agents; TGF-β receptor agonists; histone deacetylase (HDAC) inhibitors; corticosteroids; inhibitors of mitochondrial function, such as rotenone; P38 inhibitors; NF-κβ inhibitors; adenosine receptor agonists; prostaglandin E2 agonists; phosphodiesterase inhibitors, such as phosphodiesterase 4 inhibitor; proteasome inhibitors; kinase inhibitors; G-protein coupled receptor agonists; G-protein coupled receptor antagonists; glucocorticoids; retinoids; cytokine inhibitors; cytokine receptor inhibitors; cytokine receptor activators; peroxisome proliferator-activated receptor antagonists; peroxisome proliferator-activated receptor agonists; histone deacetylase inhibitors; calcineurin inhibitors; phosphatase inhibitors and oxidized ATPs. Immunosuppressants also include IDO, vitamin D3, cyclosporine A, aryl hydrocarbon receptor inhibitors, resveratrol, azathiopurine, 6-mercaptopurine, aspirin, niflumic acid, estriol, triptolide, interleukins (e.g., IL-1, IL-10), cyclosporine A, siRNAs targeting cytokines or cytokine receptors and the like.

Examples of statins include atorvastatin (LIPITOR®, TORVAST®), cerivastatin, fluvastatin (LESCOL®, LESCOL® XL), lovastatin (MEVACOR®, ALTOCOR®, ALTOPREV®), mevastatin (COMPACTIN®), pitavastatin (LIVALO®, PIAVA®), rosuvastatin (PRAVACHOL®, SELEKTINE®, LIPOSTAT®), rosuvastatin (CRESTOR®), and simvastatin (ZOCOR®, LIPEX®).

Examples of mTOR inhibitors include rapamycin and analogs thereof (e.g., CCL-779, RAD001, AP23573, C20-methallylrapamycin (C20-Marap), C16-(S)-butylsulfonamidorapamycin (C16-BSrap), C16-(S)-3-methylindolerapamycin (C16-iRap) (Bayle et al. Chemistry & Biology 2006, 13:99-107)), AZD8055, BEZ235 (NVP-BEZ235), chrysophanic acid (chrysophanol), deforolimus (MK-8669), everolimus (RAD0001), KU-0063794, PI-103, PP242, temsirolimus, and WYE-354 (available from Selleck, Houston, Tex., USA).

Examples of TGF-β signaling agents include TGF-β ligands (e.g., activin A, GDF1, GDF11, bone morphogenic proteins, nodal, TGF-βs) and their receptors (e.g., ACVR1B, ACVR1C, ACVR2A, ACVR2B, BMPR2, BMPR1A, BMPR1B, TGFβRI, TGFβRII), R-SMADS/co-SMADS (e.g., SMAD1, SMAD2, SMAD3, SMAD4, SMAD5, SMAD8), and ligand inhibitors (e.g, follistatin, noggin, chordin, DAN, lefty, LTBP1, THBS1, Decorin).

Examples of inhibitors of mitochondrial function include atractyloside (dipotassium salt), bongkrekic acid (triammonium salt), carbonyl cyanide m-chlorophenylhydrazone, carboxyatractyloside (e.g., from *Atractylis gummifera*), CGP-37157, (-)-Deguelin (e.g., from *Mundulea sericea*), F16, hexokinase II VDAC binding domain peptide, oligomycin, rotenone, Ru360, SFK1, and valinomycin (e.g., from *Streptomyces fulvissimus*) (EMD4Biosciences, USA).

Examples of P38 inhibitors include SB-203580 (4-(4-Fluorophenyl)-2-(4-methylsulfinylphenyl)-5-(4-pyridyl) 1H-imidazole), SB-239063 (trans-1-(4hydroxycyclohexyl)-4-(fluorophenyl)-5-(2-methoxy-pyrimidin-4-yl) imidazole), SB-220025 (5-(2amino-4-pyrimidinyl)-4-(4-fluorophenyl)-1-(4-piperidinyl)imidazole)), and ARRY-797.

Examples of NF (e.g., NK-κβ) inhibitors include IFRD1, 2-(1,8-naphthyridin-2-yl)-Phenol, 5-aminosalicylic acid, BAY 11-7082, BAY 11-7085, CAPE (Caffeic Acid Phenethylester), diethylmaleate, IKK-2 Inhibitor IV, IMD 0354, lactacystin, MG-132 [Z-Leu-Leu-Leu-CHO], NFκB Activation Inhibitor III, NF-κB Activation Inhibitor II, JSH-23, parthenolide, Phenylarsine Oxide (PAO), PPM-18, pyrrolidinedithiocarbamic acid ammonium salt, QNZ, RO 106-9920, rocaglamide, rocaglamide AL, rocaglamide C, rocaglamide I, rocaglamide J, rocaglaol, (R)-MG-132, sodium salicylate, triptolide (PG490), and wedelolactone.

Examples of adenosine receptor agonists include CGS-21680 and ATL-146e.

Examples of prostaglandin E2 agonists include E-Prostanoid 2 and E-Prostanoid 4.

Examples of phosphodiesterase inhibitors (non-selective and selective inhibitors) include caffeine, aminophylline, IBMX (3-isobutyl-1-methylxanthine), paraxanthine, pentoxifylline, theobromine, theophylline, methylated xanthines, vinpocetine, EHNA (erythro-9-(2-hydroxy-3-nonyl) adenine), anagrelide, enoximone (PERFAN™), milrinone, levosimendon, mesembrine, ibudilast, piclamilast, luteolin, drotaverine, roflumilast (DAXAS™, DALIRESP™), sildenafil (REVATION®, VIAGRA®), tadalafil (ADCIRCA®, CIALIS®), vardenafil (LEVITRA®, STAXYN®), udenafil, avanafil, icariin, 4-methylpiperazine, and pyrazolo pyrimidin-7-1.

Examples of proteasome inhibitors include bortezomib, disulfiram, epigallocatechin-3-gallate, and salinosporamide A.

Examples of kinase inhibitors include bevacizumab, BIBW 2992, cetuximab (ERBITUX®), imatinib (GLEEVEC®), trastuzumab (HERCEPTIN®), gefitinib (IRESSA®), ranibizumab (LUCENTIS®), pegaptanib, sorafenib, dasatinib, sunitinib, erlotinib, nilotinib, lapatinib, panitumumab, vandetanib, E7080, pazopanib, and mubritinib.

Examples of glucocorticoids include hydrocortisone (cortisol), cortisone acetate, prednisone, prednisolone, methylprednisolone, dexamethasone, betamethasone, triamcinolone, beclometasone, fludrocortisone acetate, deoxycorticosterone acetate (DOCA), and aldosterone.

Examples of retinoids include retinol, retinal, tretinoin (retinoic acid, RETIN-A®), isotretinoin (ACCUTANE®, AMNESTEEM®, CLARAVIS, SOTRET®), alitretinoin (PANRETIN®), etretinate (TEGISON™) and its metabolite acitretin (SORIATANE®), tazarotene (TAZORAC®, AVAGE®, ZORAC®), bexarotene (TARGRETIN®), and adapalene (DIFFERIN®).

Examples of cytokine inhibitors include IL1ra, IL1 receptor antagonist, IGFBP, TNF-βF, uromodulin, Alpha-2-Macroglobulin, Cyclosporin A, Pentamidine, and Pentoxifylline (PENTOPAK®, PENTOXIL®, TRENTAL®).

Examples of peroxisome proliferator-activated receptor antagonists include GW9662, PPARγ antagonist III, G335, and T0070907 (EMD4Biosciences, USA).

Examples of peroxisome proliferator-activated receptor agonists include pioglitazone, ciglitazone, clofibrate, GW1929, GW7647, L-165,041, LY 171883, PPARγ activator, Fmoc-Leu, troglitazone, and WY-14643 (EMD4Biosciences, USA).

Examples of histone deacetylase inhibitors include hydroxamic acids (or hydroxamates) such as trichostatin A, cyclic tetrapeptides (such as trapoxin B) and depsipeptides, benzamides, electrophilic ketones, aliphatic acid compounds such as phenylbutyrate and valproic acid, hydroxamic acids such as vorinostat (SAHA), belinostat (PXD101), LAQ824, and panobinostat (LBH589), benzamides such as entinostat (MS-275), CI994, and mocetinostat (MGCD0103), nicotinamide, derivatives of NAD, dihydrocoumarin, naphthopyranone, and 2-hydroxynaphaldehydes.

Examples of calcineurin inhibitors include cyclosporine, pimecrolimus, voclosporin, and tacrolimus.

Examples of phosphatase inhibitors include BN82002 hydrochloride, CP-91149, calyculin A, cantharidic acid, cantharidin, cypermethrin, ethyl-3,4-dephostatin, fostriecin sodium salt, MAZ51, methyl-3,4-dephostatin, NSC 95397, norcantharidin, okadaic acid ammonium salt from prorocentrum concavum, okadaic acid, okadaic acid potassium salt, okadaic acid sodium salt, phenylarsine oxide, various phosphatase inhibitor cocktails, protein phosphatase 1C, protein phosphatase 2A inhibitor protein, protein phosphatase 2A1, protein phosphatase 2A2, and sodium orthovanadate.

Compositions according to the invention can comprise pharmaceutically acceptable excipients, such as preservatives, buffers, saline, or phosphate buffered saline. The compositions may be made using conventional pharmaceutical manufacturing and compounding techniques to arrive at useful dosage forms. In an embodiment, compositions are suspended in sterile saline solution for injection together with a preservative.

D. Methods of Using and Making the Compositions

Viral transfer vectors can be made with methods known to those of ordinary skill in the art or as otherwise described herein. For example, viral transfer vectors can be constructed and/or purified using the methods set forth, for example, in U.S. Pat. No. 4,797,368 and Laughlin et al., Gene, 23, 65-73 (1983).

As an example, replication-deficient adenoviral vectors can be produced in complementing cell lines that provide gene functions not present in the replication-deficient adenoviral vectors, but required for viral propagation, at appropriate levels in order to generate high titers of viral transfer vector stock. The complementing cell line can complement for a deficiency in at least one replication-essential gene function encoded by the early regions, late regions, viral packaging regions, virus-associated RNA regions, or combinations thereof, including all adenoviral functions (e.g., to enable propagation of adenoviral amplicons). Construction of complementing cell lines involve standard molecular biology and cell culture techniques, such as those described by Sambrook et al., Molecular Cloning, a Laboratory Manual, 2d edition, Cold Spring Harbor Press, Cold Spring Harbor, N.Y. (1989), and Ausubel et al., Current Protocols in Molecular Biology, Greene Publishing Associates and John Wiley & Sons, New York, N.Y. (1994).

Complementing cell lines for producing adenoviral vectors include, but are not limited to, 293 cells (described in, e.g., Graham et al., J. Gen. Virol., 36, 59-72 (1977)), PER.C6 cells (described in, e.g., International Patent Application WO 97/00326, and U.S. Pat. Nos. 5,994,128 and 6,033,908), and 293-ORF6 cells (described in, e.g., International Patent Application WO 95/34671 and Brough et al., J. Virol., 71, 9206-9213 (1997)). In some instances, the complementing cell will not complement for all required adenoviral gene functions. Helper viruses can be employed to provide the gene functions in trans that are not encoded by the cellular or adenoviral genomes to enable replication of the adenoviral vector. Adenoviral vectors can be constructed, propagated, and/or purified using the materials and methods set forth, for example, in U.S. Pat. Nos. 5,965,358, 5,994,128, 6,033,908, 6,168,941, 6,329,200, 6,383,795, 6,440,728, 6,447,995, and 6,475,757, U.S. Patent Application Publication No. 2002/0034735 A1, and International Patent Applications WO 98/53087, WO 98/56937, WO 99/15686, WO 99/54441, WO 00/12765, WO 01/77304, and WO 02/29388, as well as the other references identified herein. Non-group C adenoviral vectors, including adenoviral serotype 35 vectors, can be produced using the methods set forth in, for example, U.S. Pat. Nos. 5,837,511 and 5,849,561, and International Patent Applications WO 97/12986 and WO 98/53087.

AAV vectors may be produced using recombinant methods. Typically, the methods involve culturing a host cell which contains a nucleic acid sequence encoding an AAV capsid protein or fragment thereof; a functional rep gene; a recombinant AAV vector composed of AAV inverted terminal repeats (ITRs) and a transgene; and sufficient helper functions to permit packaging of the recombinant AAV vector into the AAV capsid proteins. In some embodiments, the viral transfer vector may comprise inverted terminal repeats (ITR) of AAV serotypes selected from the group consisting of: AAV1, AAV2, AAV5, AAV6, AAV6.2, AAV7, AAV8, AAV9, AAV10, AAV11 and variants thereof.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell can contain the required component(s) under the control of an inducible promoter. However, the required component(s) may be under the control of a constitutive promoter. The recombinant AAV vector, rep sequences, cap sequences, and helper functions required for producing the rAAV of the invention may be delivered to the packaging host cell using any appropriate genetic element. The selected genetic element may be delivered by any suitable method, including those described herein. The methods used to construct any embodiment of this invention are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the present invention. See, e.g., K. Fisher et al, J. Virol., 70:520-532 (1993) and U.S. Pat. No. 5,478,745.

In some embodiments, recombinant AAV vectors may be produced using the triple transfection method (e.g., as described in detail in U.S. Pat. No. 6,001,650, the contents of which relating to the triple transfection method are incorporated herein by reference). Typically, the recombinant AAVs are produced by transfecting a host cell with a recombinant AAV vector (comprising a transgene) to be packaged into AAV particles, an AAV helper function vector, and an accessory function vector. Generally, an AAV helper function vector encodes AAV helper function sequences (rep and cap), which function in trans for productive AAV replication and encapsidation. Preferably, the AAV helper function vector supports efficient AAV vector production without generating any detectable wild-type AAV virions (i.e., AAV virions containing functional rep and cap genes). The accessory function vector can encode nucleotide sequences for non-AAV derived viral and/or cellular functions upon which AAV is dependent for replication. The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus.

Lentiviral vectors may be produced using any of a number of methods known in the art. Examples of lentiviral vectors and/or methods of their production can be found, for example, in U.S. Publication Nos. 20150224209, 20150203870, 20140335607, 20140248306, 20090148936, and 20080254008, such lentiviral vectors and methods of production are incorporated herein by reference. As an example, when the lentiviral vector is integration-incompetent, the lentiviral genome further comprises an origin of replication (ori), whose sequence is dependent on the nature of cells where the lentiviral genome has to be expressed. Said origin of replication may be from eukaryotic origin, preferably of mammalian origin, most preferably of human origin. Since the lentiviral genome does not integrate into the cell host genome (because of the defective integrase), the lentiviral genome can be lost in cells undergoing frequent cell divisions; this is particularly the case in immune cells, such as B or T cells. The presence of an origin of replication can be beneficial in some instances. Vector particles may be produced after transfection of appropriate cells, such as 293 T cells, by said plasmids, or by other processes. In the cells used for the expression of the lentiviral particles, all or some of the plasmids may be used to stably express their coding polynucleotides, or to transiently or semi-stably express their coding polynucleotides.

Methods for producing other viral vectors as provided herein are known in the art and may be similar to the exemplified methods above. Moreover, viral vectors are available commercially.

In embodiments, when preparing certain antigen-presenting cell targeted immunosuppressants, methods for attaching components to, for example, erythrocyte-binding peptides, antibodies or antigen-binding fragments thereof (or other ligand that targets an APC), or synthetic nanocarriers may be useful.

In certain embodiments, the attaching can be a covalent linker. In embodiments, immunosuppressants according to the invention can be covalently attached to the external surface via a 1,2,3-triazole linker formed by the 1,3-dipolar cycloaddition reaction of azido groups with immunosuppressant containing an alkyne group or by the 1,3-dipolar cycloaddition reaction of alkynes with immunosuppressants containing an azido group. Such cycloaddition reactions are preferably performed in the presence of a Cu(I) catalyst along with a suitable Cu(I)-ligand and a reducing agent to reduce Cu(II) compound to catalytic active Cu(I) compound. This Cu(I)-catalyzed azide-alkyne cycloaddition (CuAAC) can also be referred as the click reaction.

Additionally, covalent coupling may comprise a covalent linker that comprises an amide linker, a disulfide linker, a thioether linker, a hydrazone linker, a hydrazide linker, an imine or oxime linker, an urea or thiourea linker, an amidine linker, an amine linker, and a sulfonamide linker.

An amide linker is formed via an amide bond between an amine on one component such as an immunosuppressant with the carboxylic acid group of a second component such as the nanocarrier. The amide bond in the linker can be made using any of the conventional amide bond forming reactions with suitably protected amino acids and activated carboxylic acid such N-hydroxysuccinimide-activated ester.

A disulfide linker is made via the formation of a disulfide (S—S) bond between two sulfur atoms of the form, for instance, of R1-S—S—R2. A disulfide bond can be formed by thiol exchange of a component containing thiol/mercaptan group (—SH) with another activated thiol group or a component containing thiol/mercaptan groups with a component containing activated thiol group.

A triazole linker, specifically a 1,2,3-triazole of the form

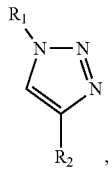

wherein R1 and R2 may be any chemical entities, is made by the 1,3-dipolar cycloaddition reaction of an azide attached to a first component with a terminal alkyne attached to a second component such as the immunosuppressant. The 1,3-dipolar cycloaddition reaction is performed with or without a catalyst, preferably with Cu(I)-catalyst, which links the two components through a 1,2,3-triazole function. This chemistry is described in detail by Sharpless et al., Angew. Chem. Int. Ed. 41(14), 2596, (2002) and Meldal, et al, Chem. Rev., 2008, 108(8), 2952-3015 and is often referred to as a "click" reaction or CuAAC.

A thioether linker is made by the formation of a sulfur-carbon (thioether) bond in the form, for instance, of R1-S—R2. Thioether can be made by either alkylation of a thiol/ mercaptan (—SH) group on one component with an alkylating group such as halide or epoxide on a second component. Thioether linkers can also be formed by Michael addition of a thiol/mercaptan group on one component to an electron-deficient alkene group on a second component containing a maleimide group or vinyl sulfone group as the Michael acceptor. In another way, thioether linkers can be prepared by the radical thiol-ene reaction of a thiol/mercaptan group on one component with an alkene group on a second component.

A hydrazone linker is made by the reaction of a hydrazide group on one component with an aldehyde/ketone group on the second component.

A hydrazide linker is formed by the reaction of a hydrazine group on one component with a carboxylic acid group on the second component. Such reaction is generally performed using chemistry similar to the formation of amide bond where the carboxylic acid is activated with an activating reagent.

An imine or oxime linker is formed by the reaction of an amine or N-alkoxyamine (or aminooxy) group on one component with an aldehyde or ketone group on the second component.

An urea or thiourea linker is prepared by the reaction of an amine group on one component with an isocyanate or thioisocyanate group on the second component.

An amidine linker is prepared by the reaction of an amine group on one component with an imidoester group on the second component.

An amine linker is made by the alkylation reaction of an amine group on one component with an alkylating group such as halide, epoxide, or sulfonate ester group on the second component. Alternatively, an amine linker can also be made by reductive amination of an amine group on one component with an aldehyde or ketone group on the second component with a suitable reducing reagent such as sodium cyanoborohydride or sodium triacetoxyborohydride.

A sulfonamide linker is made by the reaction of an amine group on one component with a sulfonyl halide (such as sulfonyl chloride) group on the second component.

A sulfone linker is made by Michael addition of a nucleophile to a vinyl sulfone. Either the vinyl sulfone or the nucleophile may be on the surface of the nanocarrier or attached to a component.

The component can also be conjugated via non-covalent conjugation methods. For example, a negative charged immunosuppressant can be conjugated to a positive charged component through electrostatic adsorption. A component containing a metal ligand can also be conjugated to a metal complex via a metal-ligand complex.

In embodiments, the component can be attached to a polymer, for example polylactic acid-block-polyethylene glycol, prior to the assembly of a synthetic nanocarrier or the synthetic nanocarrier can be formed with reactive or activatible groups on its surface. In the latter case, the component may be prepared with a group which is compatible with the attachment chemistry that is presented by the synthetic nanocarriers' surface. In other embodiments, a peptide component can be attached to VLPs or liposomes using a suitable linker. A linker is a compound or reagent that capable of coupling two molecules together. In an embodiment, the linker can be a homobifuntional or heterobifunctional reagent as described in Hermanson 2008. For example, an VLP or liposome synthetic nanocarrier containing a carboxylic group on the surface can be treated with a homobifunctional linker, adipic dihydrazide (ADH), in the presence of EDC to form the corresponding synthetic nanocarrier with the ADH linker. The resulting ADH linked synthetic nanocarrier is then conjugated with a peptide component containing an acid group via the other end of the ADH linker on nanocarrier to produce the corresponding VLP or liposome peptide conjugate.

In embodiments, a polymer containing an azide or alkyne group, terminal to the polymer chain is prepared. This polymer is then used to prepare a synthetic nanocarrier in such a manner that a plurality of the alkyne or azide groups are positioned on the surface of that nanocarrier. Alternatively, the synthetic nanocarrier can be prepared by another route, and subsequently functionalized with alkyne or azide groups. The component is prepared with the presence of either an alkyne (if the polymer contains an azide) or an azide (if the polymer contains an alkyne) group. The component is then allowed to react with the nanocarrier via the 1,3-dipolar cycloaddition reaction with or without a catalyst which covalently attaches the component to the particle through the 1,4-disubstituted 1,2,3-triazole linker.

If the component is a small molecule it may be of advantage to attach the component to a polymer prior to the assembly of synthetic nanocarriers. In embodiments, it may also be an advantage to prepare the synthetic nanocarriers with surface groups that are used to attach the component to the synthetic nanocarrier through the use of these surface groups rather than attaching the component to a polymer and then using this polymer conjugate in the construction of synthetic nanocarriers.

For detailed descriptions of available conjugation methods, see Hermanson G T "Bioconjugate Techniques", 2nd Edition Published by Academic Press, Inc., 2008. In addition to covalent attachment the component can be attached by adsorption to a pre-formed synthetic nanocarrier or it can be attached by encapsulation during the formation of the synthetic nanocarrier.

Synthetic nanocarriers may be prepared using a wide variety of methods known in the art. For example, synthetic nanocarriers can be formed by methods such as nanoprecipitation, flow focusing using fluidic channels, spray drying, single and double emulsion solvent evaporation, solvent extraction, phase separation, milling, microemulsion procedures, microfabrication, nanofabrication, sacrificial layers, simple and complex coacervation, and other methods well known to those of ordinary skill in the art. Alternatively or additionally, aqueous and organic solvent syntheses for monodisperse semiconductor, conductive, magnetic, organic, and other nanomaterials have been described (Pellegrino et al., 2005, Small, 1:48; Murray et al., 2000, Ann. Rev. Mat. Sci., 30:545; and Trindade et al., 2001, Chem. Mat., 13:3843). Additional methods have been described in the literature (see, e.g., Doubrow, Ed., "Microcapsules and Nanoparticles in Medicine and Pharmacy," CRC Press, Boca Raton, 1992; Mathiowitz et al., 1987, J. Control. Release, 5:13; Mathiowitz et al., 1987, Reactive Polymers, 6:275; and Mathiowitz et al., 1988, J. Appl. Polymer Sci., 35:755; U.S. Pat. Nos. 5,578,325 and 6,007,845; P. Paolicelli et al., "Surface-modified PLGA-based Nanoparticles that can Efficiently Associate and Deliver Virus-like Particles" Nanomedicine. 5(6):843-853 (2010)).

Materials may be encapsulated into synthetic nanocarriers as desirable using a variety of methods including but not limited to C. Astete et al., "Synthesis and characterization of PLGA nanoparticles" J. Biomater. Sci. Polymer Edn, Vol. 17, No. 3, pp. 247-289 (2006); K. Avgoustakis "Pegylated Poly(Lactide) and Poly(Lactide-Co-Glycolide) Nanoparticles: Preparation, Properties and Possible Applications in Drug Delivery" Current Drug Delivery 1:321-333 (2004); C. Reis et al., "Nanoencapsulation I. Methods for preparation of drug-loaded polymeric nanoparticles" Nanomedicine 2:8-21 (2006); P. Paolicelli et al., "Surface-modified PLGA-based Nanoparticles that can Efficiently Associate and Deliver Virus-like Particles" Nanomedicine. 5(6):843-853 (2010). Other methods suitable for encapsulating materials into synthetic nanocarriers may be used, including without limitation methods disclosed in U.S. Pat. No. 6,632,671 to Unger issued Oct. 14, 2003.

In certain embodiments, synthetic nanocarriers are prepared by a nanoprecipitation process or spray drying. Conditions used in preparing synthetic nanocarriers may be altered to yield particles of a desired size or property (e.g., hydrophobicity, hydrophilicity, external morphology, "stickiness," shape, etc.). The method of preparing the synthetic nanocarriers and the conditions (e.g., solvent, temperature, concentration, air flow rate, etc.) used may depend on the materials to be attached to the synthetic nanocarriers and/or the composition of the polymer matrix.

If synthetic nanocarriers prepared by any of the above methods have a size range outside of the desired range, synthetic nanocarriers can be sized, for example, using a sieve.

Elements of the synthetic nanocarriers may be attached to the overall synthetic nanocarrier, e.g., by one or more covalent bonds, or may be attached by means of one or more linkers. Additional methods of functionalizing synthetic nanocarriers may be adapted from Published US Patent Application 2006/0002852 to Saltzman et al., Published US Patent Application 2009/0028910 to DeSimone et al., or Published International Patent Application WO/2008/127532 A1 to Murthy et al.

Alternatively or additionally, synthetic nanocarriers can be attached to components directly or indirectly via non-covalent interactions. In non-covalent embodiments, the non-covalent attaching is mediated by non-covalent interactions including but not limited to charge interactions, affinity interactions, metal coordination, physical adsorption, host-guest interactions, hydrophobic interactions, TT stacking interactions, hydrogen bonding interactions, van der Waals interactions, magnetic interactions, electrostatic interactions, dipole-dipole interactions, and/or combinations thereof. Such attachments may be arranged to be on an external surface or an internal surface of a synthetic nanocarrier. In embodiments, encapsulation and/or absorption is a form of attaching.

Compositions provided herein may comprise inorganic or organic buffers (e.g., sodium or potassium salts of phosphate, carbonate, acetate, or citrate) and pH adjustment agents (e.g., hydrochloric acid, sodium or potassium hydroxide, salts of citrate or acetate, amino acids and their salts) antioxidants (e.g., ascorbic acid, alpha-tocopherol), surfactants (e.g., polysorbate 20, polysorbate 80, polyoxyethylene 9-10 nonyl phenol, sodium desoxycholate), solution and/or cryo/lyo stabilizers (e.g., sucrose, lactose, mannitol, trehalose), osmotic adjustment agents (e.g., salts or sugars), antibacterial agents (e.g., benzoic acid, phenol, gentamicin), antifoaming agents (e.g., polydimethylsilozone), preservatives (e.g., thimerosal, 2-phenoxyethanol, EDTA), polymeric stabilizers and viscosity-adjustment agents (e.g., polyvinylpyrrolidone, poloxamer 488, carboxymethylcellulose) and co-solvents (e.g., glycerol, polyethylene glycol, ethanol).

Compositions according to the invention may comprise pharmaceutically acceptable excipients. The compositions may be made using conventional pharmaceutical manufacturing and compounding techniques to arrive at useful dosage forms. Techniques suitable for use in practicing the present invention may be found in Handbook of Industrial Mixing: Science and Practice, Edited by Edward L. Paul, Victor A. Atiemo-Obeng, and Suzanne M. Kresta, 2004 John Wiley & Sons, Inc.; and Pharmaceutics: The Science of Dosage Form Design, 2nd Ed. Edited by M. E. Auten, 2001, Churchill Livingstone. In an embodiment, compositions are suspended in sterile saline solution for injection with a preservative.

It is to be understood that the compositions of the invention can be made in any suitable manner, and the invention is in no way limited to compositions that can be produced using the methods described herein. Selection of an appropriate method of manufacture may require attention to the properties of the particular moieties being associated.

In some embodiments, compositions are manufactured under sterile conditions or are terminally sterilized. This can ensure that resulting compositions are sterile and non-infectious, thus improving safety when compared to non-sterile compositions. This provides a valuable safety measure, especially when subjects receiving the compositions have immune defects, are suffering from infection, and/or are susceptible to infection.

Administration according to the present invention may be by a variety of routes, including but not limited to subcutaneous, intravenous, intramuscular and intraperitoneal routes. The compositions referred to herein may be manufactured and prepared for administration, in some embodiments concomitant administration, using conventional methods.

The compositions of the invention can be administered in effective amounts, such as the effective amounts described elsewhere herein. In some embodiments, the antigen-presenting cell targeted immunosuppressants and/or viral transfer vectors are present in dosage forms in an amount effective to attenuate an anti-viral transfer vector immune response or allow for readministration of a viral transfer vector to a subject. In some embodiments, the antigen-presenting cell targeted immunosuppressants and/or viral transfer vectors are present in dosage forms in an amount effective to escalate transgene expression in a subject. In preferable embodiments, the antigen-presenting cell targeted immunosuppressants and/or viral transfer vectors are present in dosage forms in an amount effective to reduce immune responses to the viral transfer vector, such as when concomitantly administered to a subject. Dosage forms may be administered at a variety of frequencies. In some embodiments, repeated administration of antigen-presenting cell targeted immunosuppressant with a viral transfer vector is undertaken.

Aspects of the invention relate to determining a protocol for the methods of administration as provided herein. A protocol can be determined by varying at least the frequency, dosage amount of the viral transfer vector and antigen-presenting cell targeted immunosuppressant and subsequently assessing a desired or undesired immune response. A preferred protocol for practice of the invention reduces an immune response against the viral transfer vector, attenuates an anti-viral transfer vector response and/or escalates transgene expression. The protocol comprises at least the frequency of the administration and doses of the viral transfer vector and antigen-presenting cell targeted immunosuppressant.

EXAMPLES

Example 1

Polymeric Nanocarrier Containing Polymer-Rapamycin Conjugate (Prophetic)

Preparation of PLGA-rapamycin conjugate:
PLGA polymer with acid end group (7525 DLG1A, acid number 0.46 mmol/g, Lakeshore Biomaterials; 5 g, 2.3 mmol, 1.0 eq) is dissolved in 30 mL of dichloromethane (DCM). N,N-Dicyclohexylcarbodimide (1.2 eq, 2.8 mmol, 0.57 g) is added followed by rapamycin (1.0 eq, 2.3 mmol, 2.1 g) and 4-dimethylaminopyridine (DMAP) (2.0 eq, 4.6 mmol, 0.56 g). The mixture is stirred at rt for 2 days. The mixture is then filtered to remove insoluble dicyclohexylurea. The filtrate is concentrated to ca. 10 mL in volume and added to 100 mL of isopropyl alcohol (IPA) to precipitate out the PLGA-rapamycin conjugate. The IPA layer is removed and the polymer is then washed with 50 mL of IPA and 50 mL of methyl t-butyl ether (MTBE). The polymer is then dried under vacuum at 35 C for 2 days to give PLGA-rapamycin as a white solid (ca. 6.5 g).

Nanocarrier containing PLGA-rapamycin is prepared as follows:

Solutions for nanocarrier formation are prepared as follows:

Solution 1: PLGA-rapamycin @ 100 mg/mL in methylene chloride. The solution is prepared by dissolving PLGA-rapamycin in pure methylene chloride. Solution 2: PLA-PEG @ 100 mg/mL in methylene chloride. The solution is prepared by dissolving PLA-PEG in pure methylene chloride. Solution 3: Polyvinyl alcohol @ 50 mg/mL in 100 mM pH 8 phosphate buffer.

A primary water-in-oil emulsion is prepared first. W1/O1 is prepared by combining solution 1 (0.75 mL), and solution 2 (0.25 mL) in a small pressure tube and sonicating at 50% amplitude for 40 seconds using a Branson Digital Sonifier 250. A secondary emulsion (W1/O1/W2) is then prepared by combining solution 3 (3.0 mL) with the primary W1/O1 emulsion, vortexing for 10 s, and sonicating at 30% amplitude for 60 seconds using the Branson Digital Sonifier 250. The W1/O1/W2 emulsion is added to a beaker containing 70 mM pH 8 phosphate buffer solution (30 mL) and stirred at room temperature for 2 hours to allow the methylene chloride to evaporate and for the nanocarriers to form. A portion of the nanocarriers is washed by transferring the nanocarrier suspension to a centrifuge tube and centrifuging at 75,600×g and 4° C. for 35 min, removing the supernatant, and re-suspending the pellet in phosphate buffered saline. The washing procedure is repeated, and the pellet is re-suspended in phosphate buffered saline for a final nanocarrier dispersion of about 10 mg/mL.

Example 2

Preparation of Gold Nanocarriers (AuNCs) Containing Rapamycin (Prophetic)

Preparation of HS-PEG-rapamycin:
A solution of PEG acid disulfide (1.0 eq), rapamycin (2.0-2.5 eq), DCC (2.5 eq) and DMAP (3.0 eq) in dry DMF is stirred at rt overnight. The insoluble dicyclohexylurea is removed by filtration and the filtrate is added to isopropyl alcohol (IPA) to precipitate out the PEG-disulfide-di-rapamycin ester and washed with IPA and dried. The polymer is then treated with tris(2-carboxyethyl)phosphine hydrochloride in DMF to reduce the PEG disulfide to thiol PEG rapamycin ester (HS-PEG-rapamycin). The resulting polymer is recovered by precipitation from IPA and dried as previously described and analyzed by H NMR and GPC.

Formation of Gold NCs (AuNCs):

An aq. solution of 500 mL of 1 mM HAuCl4 is heated to reflux for 10 min with vigorous stirring in a 1 L round-bottom flask equipped with a condenser. A solution of 50 mL of 40 mM of trisodium citrate is then rapidly added to the stirring solution. The resulting deep wine red solution is kept at reflux for 25-30 min and the heat is withdrawn and the solution is cooled to room temperature. The solution is then filtered through a 0.8 µm membrane filter to give the AuNCs solution. The AuNCs are characterized using visible spectroscopy and transmission electron microscopy. The AuNCs are ca. 20 nm diameter capped by citrate with peak absorption at 520 nm.

AuNCs conjugate with HS-PEG-rapamycin:

A solution of 150 µl of HS-PEG-rapamycin (10 µM in 10 mM pH 9.0 carbonate buffer) is added to 1 mL of 20 nm diameter citrate-capped gold nanocarriers (1.16 nM) to produce a molar ratio of thiol to gold of 2500:1. The mixture is stirred at room temperature under argon for 1 hour to allow complete exchange of thiol with citrate on the gold nanocarriers. The AuNCs with PEG-rapamycin on the surface is then purified by centrifuge at 12,000 g for 30 minutes. The supernatant is decanted and the pellet containing AuNC—S-PEG-rapamycin is then pellet washed with 1×PBS buffer. The purified Gold-PEG-rapamycin nanocarriers are then resuspend in suitable buffer for further analysis and bioassays.

Example 3

Mesoporous Silica Nanoparticles with Attached Ibuprofen (Prophetic)

Mesoporous SiO2 nanoparticle cores are created through a sol-gel process. Hexadecyltrimethyl-ammonium bromide (CTAB) (0.5 g) is dissolved in deionized water (500 mL), and then 2 M aqueous NaOH solution (3.5 mL) is added to the CTAB solution. The solution is stirred for 30 min, and then Tetraethoxysilane (TEOS) (2.5 mL) is added to the solution. The resulting gel is stirred for 3 h at a temperature of 80° C. The white precipitate which forms is captured by filtration, followed by washing with deionized water and drying at room temperature. The remaining surfactant is then extracted from the particles by suspension in an ethanolic solution of HCl overnight. The particles are washed with ethanol, centrifuged, and redispersed under ultrasonication. This wash procedure is repeated two additional times.

The SiO2 nanoparticles are then functionalized with amino groups using (3-aminopropyl)-triethoxysilane (APTMS). To do this, the particles are suspended in ethanol (30 mL), and APTMS (50 µL) is added to the suspension. The suspension is allowed to stand at room temperature for 2 h and then is boiled for 4 h, keeping the volume constant by periodically adding ethanol. Remaining reactants are removed by five cycles of washing by centrifugation and redispersing in pure ethanol.

In a separate reaction, 1-4 nm diameter gold seeds are created. All water used in this reaction is first deionized and then distilled from glass. Water (45.5 mL) is added to a 100 mL round-bottom flask. While stirring, 0.2 M aqueous NaOH (1.5 mL) is added, followed by a 1% aqueous solution of tetrakis(hydroxymethyl)phosphonium chloride (THPC) (1.0 mL). Two minutes after the addition of THPC solution, a 10 mg/mL aqueous solution of chloroauric acid (2 mL), which has been aged at least 15 min, is added. The gold seeds are purified through dialysis against water.

To form the core-shell nanocarriers, the amino-functionalized SiO2 nanoparticles formed above are first mixed with the gold seeds for 2 h at room temperature. The gold-decorated SiO2 particles are collected through centrifugation and mixed with an aqueous solution of chloroauric acid and potassium bicarbonate to form the gold shell. The particles are then washed by centrifugation and redispersed in water. Ibuprofen is loaded by suspending the particles in a solution of sodium ibuprofen (1 mg/L) for 72 h. Free ibuprofen is then washed from the particles by centrifugation and redispersing in water.

Example 4

Liposomes Containing Cyclosporine A (Prophetic)

The liposomes are formed using thin film hydration. 1,2-Dipalmitoyl-sn-glycero-3-phosphocholine (DPPC) (32 µmol), cholesterol (32 µmol), and cyclosporin A (6.4 µmol) are dissolved in pure chloroform (3 mL). This lipid solution is added to a 50 mL round-bottom flask, and the solvent is evaporated on a rotary evaporator at a temperature of 60° C. The flask is then flushed with nitrogen gas to remove remaining solvent. Phosphate buffered saline (2 mL) and five glass beads are added to the flask, and the lipid film is hydrated by shaking at 60° C. for 1 h to form a suspension. The suspension is transferred to a small pressure tube and sonicated at 60° C. for four cycles of 30 s pulses with a 30 s delay between each pulse. The suspension is then left undisturbed at room temperature for 2 h to allow for complete hydration. The liposomes are washed by centrifugation followed by resuspension in fresh phosphate buffered saline.

Example 5

Synthetic Nanocarriers Comprising Rapamycin

Materials

Rapamycin was purchased from TSZ CHEM (185 Wilson Street, Framingham, Mass. 01702; Product Catalogue # R1017). PLGA with 76% lactide and 24% glycolide content and an inherent viscosity of 0.69 dL/g was purchased from SurModics Pharmaceuticals (756 Tom Martin Drive, Birmingham, Ala. 35211. Product Code 7525 DLG 7A.) PLA-PEG block co-polymer with a PEG block of approximately 5,000 Da and PLA block of approximately 40,000 Da was purchased from SurModics Pharmaceuticals (756 Tom Martin Drive, Birmingham, Ala. 35211; Product Code 100 DL mPEG 5000 5CE). Polyvinyl alcohol (85-89% hydrolyzed) was purchased from EMD Chemicals (Product Number 1.41350.1001).

Method

Solutions were prepared as follows:

Solution 1: PLGA at 75 mg/mL and PLA-PEG at 25 mg/mL in methylene chloride. The solution was prepared by dissolving PLGA and PLA-PEG in pure methylene chloride.

Solution 2: Rapamycin at 100 mg/mL in methylene chloride. The solution was prepared by dissolving rapamycin in pure methylene chloride.

Solution 3: Polyvinyl alcohol at 50 mg/mL in 100 mM pH 8 phosphate buffer.

An oil-in-water emulsion was used to prepare the nanocarriers. The O/W emulsion was prepared by combining solution 1 (1 mL), solution 2 (0.1 mL), and solution 3 (3 mL) in a small pressure tube and sonicating at 30% amplitude for 60 seconds using a Branson Digital Sonifier 250. The O/W emulsion was added to a beaker containing 70 mM pH 8 phosphate buffer solution (30 mL) and stirred at room temperature for 2 hours to allow the methylene chloride to evaporate and for the nanocarriers to form. A portion of the nanocarriers was washed by transferring the nanocarrier suspension to a centrifuge tube and centrifuging at 75,000×g and 4° C. for 35 min, removing the supernatant, and re-suspending the pellet in phosphate buffered saline. The washing procedure was repeated, and the pellet was re-suspended in phosphate buffered saline for a final nanocarrier dispersion of about 10 mg/mL.

Nanocarrier size was determined by dynamic light scattering. The amount rapamycin in the nanocarrier was determined by HPLC analysis. The total dry-nanocarrier mass per mL of suspension was determined by a gravimetric method.

| Effective Diameter (nm) | Rapamycin Content (% w/w) |
|---|---|
| 227 | 6.4 |

Example 6

Synthetic Nanocarriers Comprising GSK1059615

Materials

GSK1059615 was purchased from MedChem Express (11 Deer Park Drive, Suite 102D Monmouth Junction, N.J. 08852), product code HY-12036. PLGA with a lactide:glycolide ratio of 1:1 and an inherent viscosity of 0.24 dL/g was purchased from Lakeshore Biomaterials (756 Tom Martin Drive, Birmingham, Ala. 35211), product code 5050 DLG 2.5 A. PLA-PEG-OMe block co-polymer with a methyl ether terminated PEG block of approximately 5,000 Da and an overall inherent viscosity of 0.26 DL/g was purchased from Lakeshore Biomaterials (756 Tom Martin Drive, Birmingham, Ala. 35211; Product Code 100 DL mPEG 5000 5K-E). Cellgro phosphate buffered saline 1×pH 7.4 (PBS 1×) was purchased from Corning (9345 Discovery Blvd. Manassas, Va. 20109), product code 21-040-CV.

Method

Solutions were prepared as follows:

Solution 1: PLGA (125 mg), and PLA-PEG-OMe (125 mg), were dissolved in 10 mL of acetone. Solution 2: GSK1059615 was prepared at 10 mg in 1 mL of N-methyl-2-pyrrolidinone (NMP).

Nanocarriers were prepared by combining Solution 1 (4 mL) and Solution 2 (0.25 mL) in a small glass pressure tube and adding the mixture drop wise to a 250 mL round bottom flask containing 20 mL of ultra-pure water under stirring. The flask was mounted onto a rotary evaporation device, and the acetone was removed under reduced pressure. A portion of the nanocarriers was washed by transferring the nanocarrier suspension to centrifuge tubes and centrifuging at 75,600 rcf and 4° C. for 50 minutes, removing the supernatant, and re-suspending the pellet in PBS 1×. The washing procedure was repeated, and the pellet was re-suspended in PBS 1× to achieve a nanocarrier suspension having a nominal concentration of 10 mg/mL on a polymer basis. The washed nanocarrier solution was then filtered using 1.2 µm PES membrane syringe filters from Pall, part number 4656. An identical nanocarrier solution was prepared as above, and pooled with the first after the filtration step. The homogenous suspension was stored frozen at −20° C.

Nanocarrier size was determined by dynamic light scattering. The amount of GSK1059615 in the nanocarrier was determined by UV absorption at 351 nm. The total dry-nanocarrier mass per mL of suspension was determined by a gravimetric method.

| Effective Diameter (nm) | GSK1059615 Content (% w/w) |
|---|---|
| 143 | 1.02 |

Example 7

Erythrocyte-Binding Therapeutic with a Viral Transfer Vector Antigen (Prophetic)

An erythrocyte-binding therapeutic is prepared based on the teachings of U.S. Publication No. 20120039989 and used as an antigen-presenting cell targeted immunosuppressant. The erythrocyte-binding therapeutic may comprise any one of ERY1, ERY19, ERY59, ERY64, ERY123, ERY141 and ERY162 and any one of the viral transfer vector antigens described herein, such as a viral vector antigen, e.g., a capsid protein (or peptide antigen derived therefrom), or a protein (or peptide antigen derived therefom), such as a therapeutic protein (or peptide antigen derived therefrom) that is encoded by a transgene as described herein.

Example 8

Particles Containing an Inhibitor of the NF-kB Pathway (Prophetic)

An antigen-presenting cell targeted immunosuppressant is prepared according to the teachings of U.S. Publication No. 20100151000. The particle may be a liposome or polymeric particle and comprises any one of the immunosuppressants provided herein or any one of the inibitors of the NF-kB pathway provided in U.S. Publication No. 20100151000, which inhibitors are incorporated herein by reference in their entirety. In addition, the liposome or polymeric particle may further comprise any one of the viral transfer vector antigens described herein, such as a viral vector antigen, e.g., a capsid protein (or peptide antigen derived therefrom), or a protein (or peptide antigen derived therefom), such as a therapeutic protein (or peptide antigen derived therefrom), that is encoded by a transgene as described herein.

Example 9

Adenoviral Transfer Vector with a Gene Therapy Transgene (Prophetic)

An adenoviral transfer vector is generated according to the methods provided in U.S. Patent Publication 2004/0005293. Such a vector may comprise any one of the transgenes as provided herein. For example, an Ad-AAT-hFVIII vector that expresses the human B-domain deleted FVIII cDNA from the human alfa1-antitrypsin promoter (AAT) is prepared. An HPRT stuffer fragment is employed to optimize vector size and to avoid vector rearrangements (Parks R J, Graham F L. A helper-dependent system for adenovirus vector production helps define a lower limit for efficient DNA packaging. J Virol. 1997, 71:3293-3298). The Cre66 packaging cell line is used.

Example 10

Concomitant Administration of a Viral Transfer Vector with Synthetic Nanocarriers Coupled to Immunosuppressant (Prophetic)

The viral transfer vector of any one of the Examples, such as Example 9, is administered concomitantly, such as on the same day, as any one of the antigen-presenting cell targeted immunosuppressants provided herein, such as in Examples 1-8 or 12, to subjects recruited for a clinical trial. One or more immune responses against the viral transfer vector is evaluated. The level(s) of the one or more immune responses against the viral transfer vector can be evaluated by comparison with the level(s) of the one or more immune responses in the subjects, or another group of subjects, administered the viral transfer vector in the absence of the antigen-presenting cell targeted immunosuppressant, such as when administered the viral transfer vector alone. In embodiments, repeated concomitant administration is evaluated in a similar manner.

In an application of the information established during such trials, the viral transfer vector and antigen-presenting cell targeted immunosuppressant can be administered concomitantly to subjects in need of viral transfer vectors when such subjects are expected to have an undesired immune response against the viral transfer vector when not administered concomitantly with the antigen-presenting cell targeted immunosuppressant. In a further embodiment, a protocol using the information established during the trials can be prepared to guide the concomitant dosing of the viral transfer vector and synthetic nanocarriers of subjects in need of treatment with a viral transfer vector and have or are expected to have an undesired immune response against the viral transfer vector without the benefit of the antigen-presenting cell targeted immunosuppressant. The protocol so prepared can then be used to treat subjects, particularly human subjects.

Example 11

Administration of a Viral Transfer Vector with a Gene Therapy Transgene with Synthetic Nanocarriers Coupled to Immunosuppressant Two successive intravenous (i.v.) inoculations of adeno-associated virus expressing recombinant green fluorescent protein (AAV-GFP) led to higher GFP expression in liver cells in vivo if nanocarrier-encapsulated immunosuppressant (NCs) was co-injected at boost stage.
Experimental Methods Male C57BL/6 mice were used (5 mice/group). Animals were injected with 200 µL of AAV-GFP or AAV-GFP+ synthetic nanocarriers comprising rapamycin (NCs) mixture once or twice over a 21d interval at different iterations (see Table 1 below). At d33 after the first injection (=d12 after the second injection for those groups that were injected twice) animals were sacrificed, their livers treated with collagenase 4 (Worthington, Lakewood, N.J.), meshed and total cell suspensions analyzed by FACS for GFP expression. Briefly, tissue was initially perfused with collagenase (100 U), incubated at 37° C. (30 min), collagenase supernatant removed, and quenched with 2% FBS. Tissue samples were then cut into ~2 mm squares, digested (collagenase, 400 U) with repeated agitation, filtered (nylon mesh), spun down (1,500 rpm), and pellets re-suspended in ice-cold 2% FBS.

At day 14 after the first injections all animals were bled and their serum analyzed for antibodies against AAV with ELISA as follows. 96-well plates were coated with 50 µL of AAV at $2 \times 10^9$ vg/mL in carbonate buffer for 92 hours, and then blocked for 2 hours with 300 µL of casein. Samples were added at a 1:40 dilution in 50 µL of casein, and incubated for 2 hours at RT. Rabbit Anti-mouse IgG (Jackson ImmunoResearch, West Grove, Pa., 315-035-008) was used as a secondary antibody (0.5 µg/mL, 1 hour) and then TMB substrate was added (10 min) followed by the stop solution. Plates were then read at wavelength of 450 nm with a subtraction of background at 570 nm. Mouse monoclonal anti-AAV8 antibody (Fitzgerald, Acton, Mass., 10R-2136) served as a positive control.

Amounts of AAV-GFP: $1 \times 10^{10}$ viral genomes (VG) at d0 prime, $5 \times 10^{10}$ VG at d21 boost.

Amounts of Nanocarrier-Encapsulated Immunosuppressant (Rapamycin or Rapa) Used: 50 µg of nanocarrier-entrapped Rapa at either prime (gr. 2, 3 and 5) or boost (gr. 3 and 4).

TABLE 1

Experimental Groups

| Gr. # | Immunization, i.v. | NCs (i.v., day 0) | Boost, d. 21 |
|---|---|---|---|
| 1 | AAV-GFP ($1 \times 10^{10}$ VG) | None | AAV-GFP; $5 \times 10^{10}$ VG |
| 2 | Same | 50 µg of Rapa | Same |
| 3 | Same | Same | AAV-GFP, $5 \times 10^{10}$ VG + NCs |
| 4 | Same | None | AAV-GFP, $5 \times 10^{10}$ VG + NCs |
| 5 | Same | 50 µg of Rapa | None |
| 6 | Same | None | None |

Results

Figure 2:
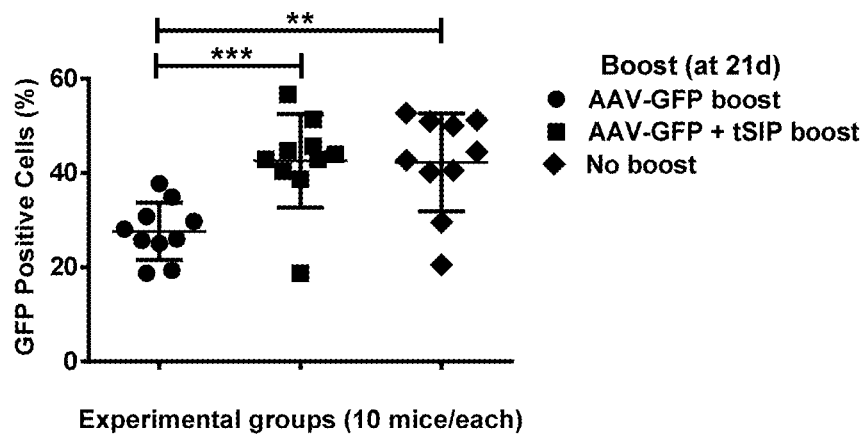
FIG. 2. shows GFP expression in livers of AAV-injected mice as a function of boost with or without synthetic nanocarriers comprising rapamycin. Data presented are the same as in FIG. 1, but are grouped according to whether AAV boost employed co-administration with the synthetic nanocarriers comprising rapamycin or not (unboosted samples from gr. 5 and 6 are also shown as a separate 'supergroup').
Figure 3:
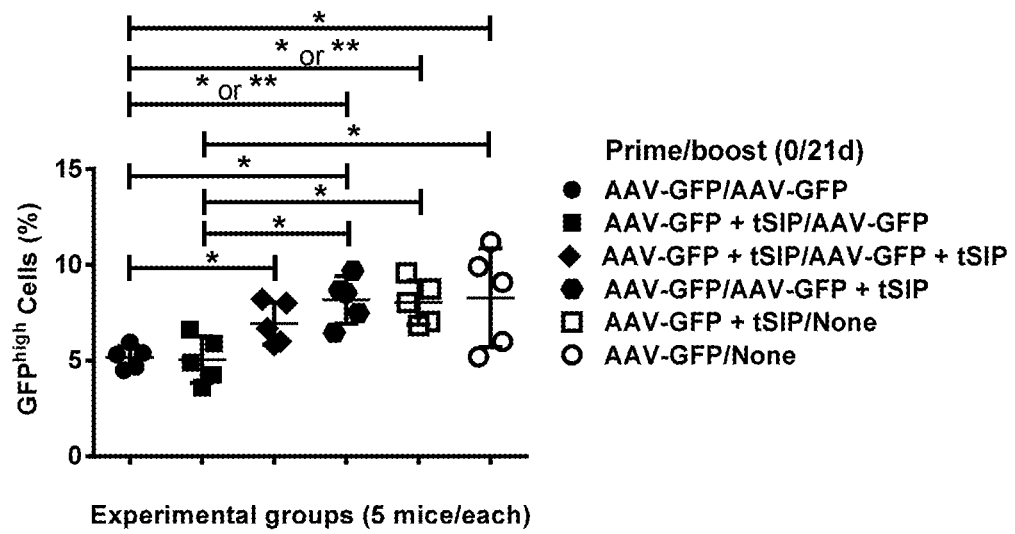
FIG. 3. demonstrates the GFP$^{high}$ cell share in livers of animals injected with AAV with or without synthetic nanocarriers comprising rapamycin. GFP-positive cells (as presented in FIG. 1) were gated and then a population with an average GFP fluorescence intensity of 10 times higher than average in the parent population was gated again. Numbers presented are percentage from the parent GFP-positive population as seen in FIG. 1.

Statistically higher levels of GFP expression in the liver of AAV-injected mice were seen if NCs was utilized at the boost stage after prime with AAV-GFP only compared to both prime and boost with AAV-GFP only (FIG. 1). There was also a trend towards higher GFP expression if AAV-GFP was co-injected with NCs at both prime and boost, but due to a single outlier it did not manifest a clear statistical superiority to prime-boost with AAV-GFP only. Utilization of NCs only at prime injection did not result in any elevation of GFP expression (FIG. 1, gr. 1 vs. gr. 2 and gr. 5 vs. gr. 6). Collectively, it appeared that co-administration of AAV-GFP and NCs at boost drives the higher GFP expression in animals, which received two injections of recombinant AAV according to the current regimen. This was pronounced if all the animals boosted with AAV-GFP only (whether or not treated with NCs at prime) are plotted against all the animals boosted with AAV-GFP+NCs (FIG. 2) with 9/10 animals boosted in presence of NCs exhibiting higher GFP expression than all (10/10) animals boosted without NCs (average expression increase in the former being >50%). Similarly, if only highly-GFP positive liver cells were considered, utilization of NCs during boost resulted in statistically higher numbers than boost with AAV-GFP without NCs, whether or not NCs was utilized at the prime stage (FIG. 3). It was also apparent that AAV-GFP boost without NCs led to decreased GFP expression even compared to a single prime immunization.

Figure 4:
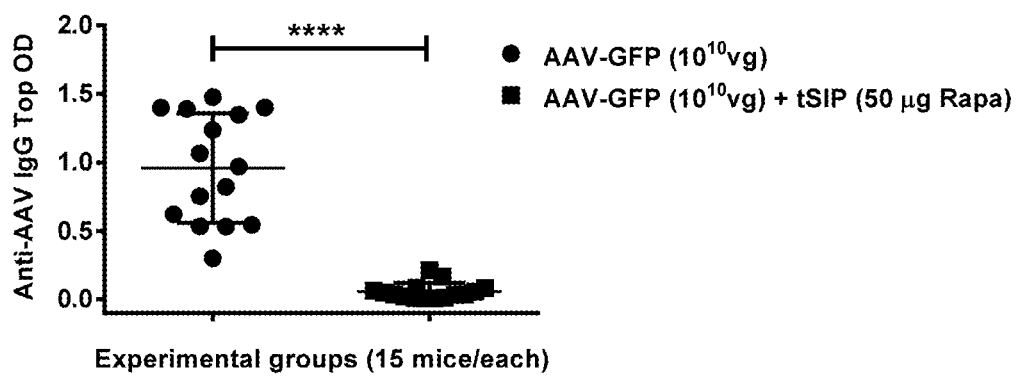
FIG. 4. shows results from an experiment where mice were bled at d14 after receiving a single AAV-GFP inoculation with or without co-administration of synthetic nanocarriers comprising rapamycin and their sera assayed for antibodies against AAV. Top ODs for 1:40 serum dilutions are shown for all mice. Background normal mouse serum had an OD of 0.227.
Figure 5:
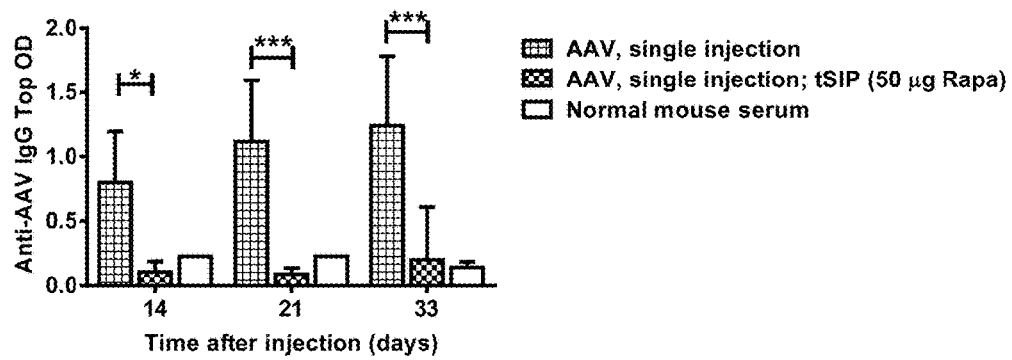
FIG. 5. shows results from an experiment where mice were bled at days 14, 21 and 33 after receiving a single AAV-GFP inoculation with or without co-administration of synthetic nanocarriers comprising rapamycin (i.v.) and their sera assayed for antibodies against AAV. Top ODs for 1:40 serum dilutions are shown for all mice. Background normal mouse serum activity is shown. Statistical significance is calculated using two-way ANOVA.

Separately, mice were bled at d14 and their serum tested for the presence of antibodies to AAV. At this point, all mice had been injected with AAV-GFP once with or without co-administration of NCs (resulting in two groups of 15 mice each). As seen in FIG. 4, all 15/15 mice which received a single AAV-GFP injection without NCs had exhibited antibody reactivity against AAV, resulting in top ODs higher than normal serum control (OD=0.227), while no mouse which received AAV co-administered with NCs exhibited a detectable level of antibodies to AAV. If only a single AAV immunization was employed, levels of anti-AAV antibodies stayed below the baseline at d21 in mice to which NCs was co-administered with AAV, while being elevated in mice that received AAV without NCs (FIG. 5). At 33 days after a single injection, levels of these in untreated mice were still moderately growing, while in NCs-treated group 4 out of 5 mice had no detectable antibodies to AAV (FIG. 5).

Figure 6:
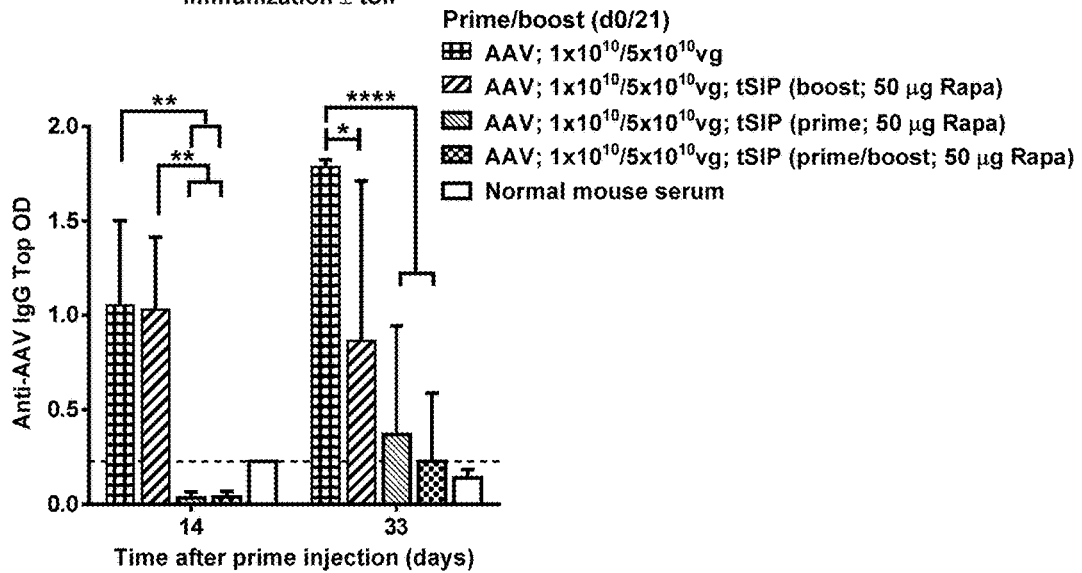
FIG. 6. shows results from an experiment where mice were injected with AAV-GFP at days 0 and 21 with or without co-administration of synthetic nanocarriers comprising rapamycin (i.v.) at either or both injections, then bled at days 14 and 33 and their sera assayed for antibodies against AAV. Top ODs for 1:40 serum dilutions are shown for all mice. Background normal mouse serum activity is shown. Statistical significance is calculated using two-way ANOVA.
Figure 7:
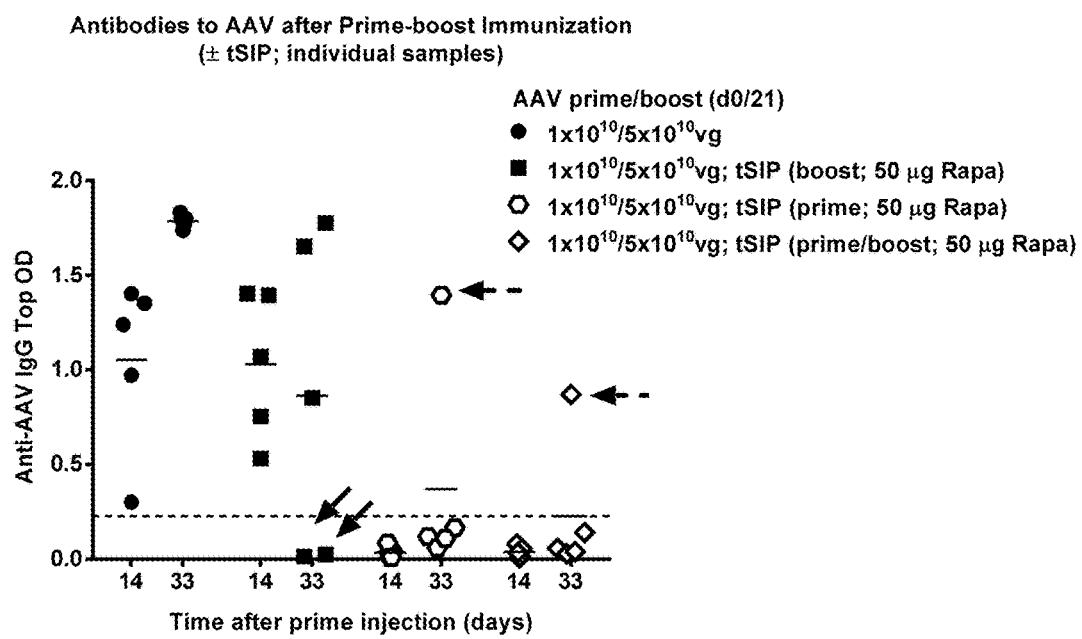
FIG. 7. provides data that are the same as in FIG. 6 with the readings for individual mice shown. Two mice in the group treated with synthetic nanocarriers comprising rapamycin only at boost immunization (d21) did not show detectable antibodies at day 33 despite being positive at d14 (solid arrows). One of five mice in both groups treated with synthetic nanocarriers comprising rapamycin at the prime had a detectable antibody level at d33 (dashed arrows) with the mouse from the group treated with synthetic nanocarriers comprising rapamycin at both prime and boost having a lower antibody level (open diamonds).

If mice were boosted with AAV-GFP at day 21, then antibody levels in untreated mice continued to grow significantly while being blunted in those mice that received NCs only at boost (FIGS. 6 and 7). Interestingly, two mice in this latter group while being positive at d14 (no treatment at prime) had their levels of antibodies to AAV fall below background by d33 (FIG. 7). At the same time, 8/10 mice treated with NCs at prime had no detectable antibodies at d33 even after d21 boost (FIGS. 6 and 7). Application of NCs at AAV boost may have had a minor effect in blocking generation of antibodies to AAV although at this point it was not statistically significant from no NCs treatment at boost (FIGS. 6 and 7). Thus, NCs treatment at prime appears to be important for blocking the development of antibodies to AAV with its administration at later time-points also being beneficial.

The results demonstrate the benefit of administering synthetic nanocarriers coupled to an immunosuppressant in conjunction with a viral transfer vector for reducing antibody responses against the viral transfer vector. Such benefits were seen with concomitant administration of synthetic nanocarriers coupled to an immunosuppressant in conjunction with a viral transfer vector encoding a protein for expression. Accordingly, protocols for reducing anti-viral transfer vector antibody responses are hereinabove exemplified.

Example 12

Synthetic Nanocarriers Comprising Rapamycin

Materials

PLA with an inherent viscosity of 0.41 dL/g was purchased from Lakeshore Biomaterials (756 Tom Martin Drive, Birmingham, Ala. 35211), product code 100 DL 4 A.

PLA-PEG-OMe block co-polymer with a methyl ether terminated PEG block of approximately 5,000 Da and an overall inherent viscosity of 0.50 DL/g was purchased from Lakeshore Biomaterials (756 Tom Martin Drive, Birmingham, Ala. 35211), product code 100 DL mPEG 5000 5CE.

Rapamycin was purchased from Concord Biotech Limited (1482-1486 Trasad Road, Dholka 382225, Ahmedabad India), product code SIROLIMUS.

Sorbitan monopalmitate was purchased from Sigma-Aldrich (3050 Spruce St., St. Louis, Mo. 63103), product code 388920.

EMPROVE® Polyvinyl Alcohol (PVA) 4-88, USP (85-89% hydrolyzed, viscosity of 3.4-4.6 mPa·s) was purchased from EMD Chemicals Inc. (480 South Democrat Road Gibbstown, N.J. 08027), product code 1.41350.

Dulbecco's phosphate buffered saline 1× (DPBS) was purchased from Lonza (Muenchensteinerstrasse 38, CH-4002 Basel, Switzerland), product code 17-512Q.

Method

Solutions were prepared as follows:

Solution 1: A polymer, rapamycin, and sorbitan monopalmitate mixture was prepared by dissolving PLA at 37.5 mg/mL, PLA-PEG-Ome at 12.5 mg/mL, rapamycin at 8 mg/mL, and sorbitan monopalmitate at 2.5 in dichloromethane.

Solution 2: Polyvinyl alcohol was prepared at 50 mg/mL in 100 mM pH 8 phosphate buffer.

An O/W emulsion was prepared by combining Solution 1 (1.0 mL) and Solution 2 (3 mL) in a small glass pressure tube, vortex mixed for 10 seconds. The formulation was then homogenized by sonication at 30% amplitude for 1 minute. The emulsion was then added to an open beaker containing DPBS (30 mL). A second O/W emulsion was prepared using the same materials and method as above and then added to the same beaker containing the first emulsion and DPBS. The combined emulsion was then stirred at room temperature for 2 hours to allow the dichloromethane to evaporate and for the nanocarriers to form. A portion of the nanocarriers was washed by transferring the nanocarrier suspension to a centrifuge tube and centrifuging at 75,600×g and 4° C. for 50 minutes, removing the supernatant, and re-suspending the pellet in DPBS containing 0.25% w/v PVA. The wash procedure was repeated and then the pellet was re-suspended in DPBS containing 0.25% w/v PVA to achieve a nanocarrier suspension having a nominal concentration of 10 mg/mL on a polymer basis. The nanocarrier suspension was then filtered using a 0.22 μm PES membrane syringe filter (Millipore part number SLGP033RB). The filtered nanocarrier suspension was then stored at −20° C.

Nanocarrier size was determined by dynamic light scattering. The amount of rapamycin in the nanocarrier was determined by HPLC analysis. The total dry-nanocarrier mass per mL of suspension was determined by a gravimetric method.

| Effective Diameter (nm) | Rapamycin Content (% w/w) | Nanocarrier Conc (mg/mL) |
|---|---|---|
| 150 | 11.5 | 11.1 |

Example 13

Single Administration of a Viral Transfer Vector with a Gene Therapy Transgene Induces Anti-Vector Antibody Responses that can be Inhibited by Concomitant Administration with Synthetic Nanocarriers Coupled to Immunosuppressant A single intravenous (i.v.) administration of adeno-associated virus encoding a recombinant green fluorescent protein (AAV-GFP) (Virovek, Hayward, Calif.) under a CMV promoter led to an anti-AAV antibody response that was inhibited by concomitant treatment with nanocarrier-encapsulated immunosuppressant (produced according to Example 12).

Experimental Methods

Male C57BL/6 mice were used (5-15 mice/group). Animals were injected i.v. with 200 μL of AAV8-GFP or an admixture of AAV8-GFP+NCs, a PLGA nanocarrier containing rapamycin (see Table 2 below). On day 14 after treatment, all animals were bled and their sera analyzed for antibodies against AAV8 by ELISA. Briefly, 96-well plates were coated with 50 μL of AAV8 at 2×10$^9$ vector genomes (vg)/mL in carbonate buffer for 92 hours, and then blocked for 2 hours with 300 μL of casein. Samples were added at a 1:40 dilution in 50 μL of casein, and incubated for 2 hours at room temperature (RT). Horse radish peroxidase-conjugated rabbit anti-mouse IgG (Jackson ImmunoResearch, West Grove, Pa., 315-035-008) was used as a secondary antibody (0.5 μg/mL, 1 hour) and then TMB substrate was added (10 min) followed by the stop solution. Plates were then read at a wavelength of 450 nm with a subtraction of background at 570 nm. Mouse monoclonal anti-AAV8 antibody (Fitzgerald, Acton, Mass., 10R-2136) served as a positive control.

Amounts of AAV-GFP:1×10$^{10}$ viral genomes (vg) at day 0 (prime) and 5×10$^{10}$ vg at day 21 (boost).

Amounts of Nanocarrier-Encapsulated Rapamycin (Rapa) Used:50 μg of nanocarrier-entrapped rapamycin.

TABLE 2

| | Experimental Groups | |
| --- | --- | --- |
| Gr. # | Immunization, i.v. day 0 | NCs (i.v. day 0) |
| 1 | AAV-GFP (1 × 10$^{10}$ VG) | None |
| 2 | AAV-GFP (1 × 10$^{10}$ VG) | 50 μg of Rapa |

Figure 8:
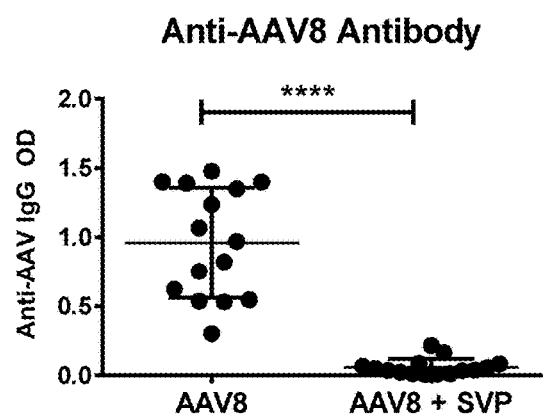
FIG. 8. shows results from an experiment where mice were bled at d14 after receiving a single AAV-GFP inoculation with or without co-administration of synthetic nanocarriers comprising rapamycin and their sera assayed for antibodies against AAV. Top ODs for 1:40 serum dilutions are shown for all mice. Background normal mouse serum had an OD of 0.227. N=15 mice per group.
Figure 9:
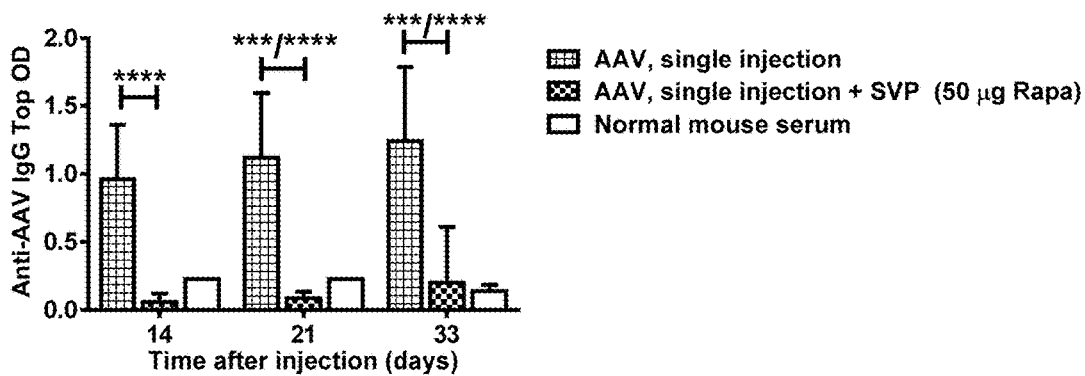
FIG. 9. shows results from an experiment where mice were bled at days 14, 21 and 33 after receiving a single AAV-GFP inoculation with or without co-administration of synthetic nanocarriers comprising rapamycin (i.v.) and their sera assayed for antibodies against AAV. Top ODs for 1:40 serum dilutions are shown for all mice. Background normal mouse serum levels are shown. Statistical significance is calculated using two-way ANOVA. N=15 mice/group at day 14 and 5 mice/group at days 21 and 33.

Mice were bled at d14 and their sera tested for the presence of antibodies to AAV8. At this point, all mice had been injected with AAV8-GFP once with or without co-administration of the nanocarriers (15 mice each). As seen in FIG. 8, all mice which received a single AAV-GFP injection without nanocarriers had exhibited antibody reactivity against AAV8, resulting in antibody levels higher than the normal serum control (OD=0.227), while mice which received AAV8 co-administered with NCs exhibited little or no detectable levels of antibodies to AAV8. Levels of anti-AAV8 antibodies stayed at or below the baseline at d21 in the NCs treated group (n=5), while being elevated in mice that received AAV8-GFP without NCs (FIG. 9). At 33 days after a single injection of AAV8-GFP, anti-AAV8 antibody levels in untreated mice continued to increase moderately, while in the NCs-treated group 4 out of 5 mice had no detectable antibodies to AAV (FIG. 9).

The results demonstrate the benefit of administering synthetic nanocarriers coupled to an immunosuppressant in conjunction with a viral transfer vector for reducing antibody responses against the viral transfer vector. Such benefits were seen with concomitant administration of synthetic nanocarriers coupled to an immunosuppressant in conjunction with an viral transfer vector comprising a transgene encoding a protein for expression. Accordingly, protocols for reducing anti-viral transfer vector antibody responses are herein exemplified.

Example 14

Concomitant Administration of a Viral Transfer Vector with a Gene Therapy Transgene with Synthetic Nanocarriers Coupled to Immunosuppressant Inhibits the Anti-AAV Antibody Response Experimental Methods Male C57BL/6 mice were used (5 mice/group). Animals were injected with 200 μL of AAV8-GFP (Virovek, Hayward, Calif.) or an admixture of AAV8-GFP+NCs (as produced in Example 12) on day 0 and/or day 21 as indicated in Table 3. Sera were collected on day 0 and 33 and analyzed for anti-AAV8 antibody levels by ELISA as described above.

Amounts of AAV-GFP:1×10$^{10}$ viral genomes (vg) at d0 prime, 5×10$^{10}$ vg at d21 boost.

Amounts of Nanocarrier-Encapsulated Immunosuppressant (Rapamycin or Rapa) Used:50 μg of nanocarrier-entrapped Rapa at either prime (gr. 2 and 4) or boost (gr. 3 and 4).

TABLE 3

| | Experimental Groups | | | |
| --- | --- | --- | --- | --- |
| | Day 0 | | Day 21 | |
| Gr. # | Viral transfer vector (i.v.) | NCs (i.v.) | Viral transfer vector (i.v.) | NCs (i.v.) |
| 1 | AAV-GFP (1 × 10$^{10}$ vg) | None | AAV-GFP (5 × 10$^{10}$ vg) | None |
| 2 | AAV-GFP (1 × 10$^{10}$ vg) | None | AAV-GFP (5 × 10$^{10}$ vg) | 50 μg of Rapa |
| 3 | AAV-GFP (1 × 10$^{10}$ vg) | 50 μg of Rapa | AAV-GFP (5 × 10$^{10}$ vg) | None |
| 4 | AAV-GFP (1 × 10$^{10}$ vg) | 50 μg of Rapa | AAV-GFP (5 × 10$^{10}$ vg) | 50 μg of Rapa |

Results

Figure 10:
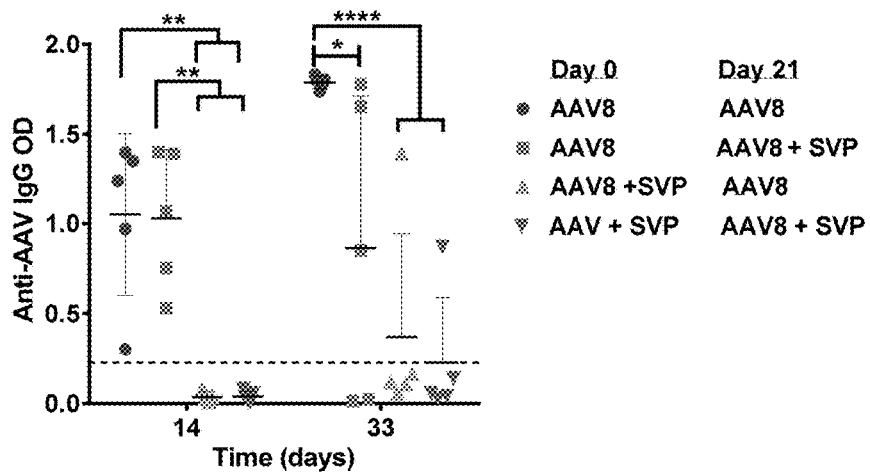
FIG. 10 shows results from an experiment where mice were injected with AAV8-GFP at days 0 and 21 with or without co-administration of synthetic nanocarriers comprising rapamycin (i.v.) at one or both injections, as indicated, and then bled at days 14 and 33. Sera were assayed for antibodies against AAV8 by ELISA. ODs for 1:40 serum dilutions are shown for all mice. Background level of normal mouse serum is indicated by the dotted line. Statistical significance is calculated using two-way ANOVA.

Mice injected with AAV8-GFP on day 0 in the absence of NCs showed a robust anti-AAV8 antibody response that increased significantly after the second injection of AAV8-GFP on day 21 (FIG. 10). However if NCs was concomitantly administered with the AAV8-GFP on day 21, the antibody response on average was significantly blunted. Interestingly, two mice in this latter group which were antibody positive on d14 had no detectable levels of antibodies to AAV8 on d33 (FIG. 10). However anti-AAV8 antibody titers increased in 2 other mice. In contrast, NCs concomitantly administered at the time of the first AAV8-GFP injection (day 0) completely inhibited the anti-AAV8 antibody response at day 14. The anti-AAV8 antibody was also inhibited in 4 of 5 mice at day 33 after a second administration of AAV8-GFP alone on day 21. Concomitant administration of NCs at both day 0 and 21 showed a similar trend. Thus, NCs treatment at the time of the first administration of AAV is important for blocking the development of antibodies to AAV. Additional administration of NCs upon repeat dosing of AAV may be potentially beneficial.

The results demonstrate the benefit of administering synthetic nanocarriers coupled to an immunosuppressant in conjunction with a viral transfer vector for reducing antibody responses against the viral transfer vector. Such benefits were seen with concomitant administration of synthetic nanocarriers coupled to an immunosuppressant in conjunction with a viral transfer vector encoding a protein for expression. Accordingly, protocols for reducing anti-viral transfer vector antibody responses are herein exemplified.

Example 15

Therapeutic Administration of Synthetic Nanocarriers Coupled to Immunosuppressant Enhances the Maintenance of Transgene Expression upon Repeat Dosing of a Viral Transfer Vector Two successive intravenous (i.v.) inoculations of adeno-associated virus encoding recombinant green fluorescent protein (AAV8-GFP) (Virovek, Hayward, Calif.) led to higher GFP expression in liver cells in vivo if nanocarrier-encapsulated immunosuppressant (NCs) (as produced in Example 12) was co-injected at the time of a repeat administration of a viral transfer vector encoding a protein for expression.

Experimental Methods

Male C57BL/6 mice were used (5 mice/group). Animals were injected with 200 µL of AAV8-GFP in the absence of NCs on day 0. One group of animals received no further treatment, while other groups received a second dose of AAV8-GFP on day 21 with or without concomitant administration of NCs carrying 50 µg rapamycin (see Table 4 below). At d33 after the first injection (12 days after the second injection for those groups that were injected twice) animals were sacrificed, their livers treated with collagenase 4 (Worthington, Lakewood, N.J.), meshed and total cell suspensions were analyzed by flow cytometry for GFP expression. Briefly, tissue was initially perfused with collagenase (100 U) and incubated at 37° C. for 30 min. The collagenase supernatant was removed, and quenched with 2% FBS. Tissue samples were then cut into ~2 mm squares, digested (collagenase, 400 U) with repeated agitation, filtered (nylon mesh), spun down (1,500 rpm), and pellets re-suspended in ice-cold 2% FBS.

Amounts of AAV-GFP:

$1 \times 10^{10}$ viral genomes (vg) at d0 and $5 \times 10^{10}$ vg at d21 (groups 2 and 3 only).

Amounts of Nanocarrier-Encapsulated Immunosuppressant (Rapamycin or Rapa) Used:

50 µg of nanocarrier-entrapped *Rapa* at day 21 (gr. 3).

TABLE 4

Experimental Groups

| Gr. # | Day 0<br>Viral transfer vector (i.v.) | Day 21<br>Viral transfer vector (i.v.) | NCs (i.v.) |
|---|---|---|---|
| 1 | AAV-GFP<br>($1 \times 10^{10}$ vg) | None | None |
| 2 | AAV-GFP<br>($1 \times 10^{10}$ vg) | AAV-GFP<br>($5 \times 10^{10}$ vg) | None |
| 3 | AAV-GFP<br>($1 \times 10^{10}$ vg) | AAV-GFP<br>($5 \times 10^{10}$ vg) | 50 µg of Rapa |

Results

Figure 11:
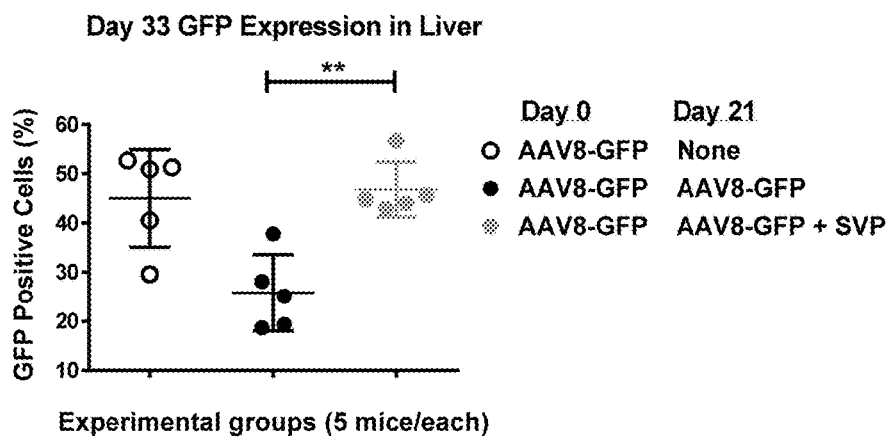
FIG. 11 shows GFP expression in livers of mice injected with AAV with or without synthetic nanocarriers comprising rapamycin at prime or boost. All cells in suspension have been analyzed for GFP expression with the exception of high side-scatter debris (2-3% of total, a by-product of collagenase treatment) excluded by the first 'clean' gate. All the remaining cells were gated for relative GFP strength (FL-1 channel). Numbers shown represent the percentage of GFP-positive cells of the total parent population.

Statistically higher levels of GFP expression in the liver of AAV8-GFP treated mice were seen if NCs was concomitantly administered with the second injection of AAV8-GFP on d21 compared to animals that received a second injection of AAV8-GFP in the absence of NCs (FIG. 11). The level of GFP expression observed in mice that received a second injection of AAV8-GFP plus NCs was similar to that observed in mice that received only a single dose of AAV8-GFP on day 0. These results indicate that the co-administration of NCs at the time of the second dose of AAV8-GFP was important to maintain expression of GFP, perhaps by inhibiting cytolytic T cells which could eliminate transduced liver cells expressing GFP.

The results demonstrate the benefit of administering synthetic nanocarriers coupled to an immunosuppressant in conjunction with a viral transfer vector for maintaining expression of the vector transgene. Such benefits were seen with concomitant administration of synthetic nanocarriers coupled to an immunosuppressant in conjunction with a viral transfer vector comprising a transgene encoding a protein for expression.

Example 16

Concomitant Administration of a Synthetic Nanocarriers Coupled to Immunosuppressant Enhances Transgene Expression Experimental Methods Male C57BL/6 mice were used (5 mice/group). Animals were injected with 200 µL of AAV-red fluorescence protein (RFP) (Virovek, Hayward, Calif.) on day 0 (groups 1-5) and/or day 21 (groups 1-4, 6) (see Table 5 below). NCs carrying 50 µg rapamycin was concomitantly administered on day 0 (groups 2, 4) and/or day 21 (groups 3, 4). At d33 after the first injection (12 days after the second injection for those groups that were injected twice) animals were sacrificed, their livers treated with collagenase 4 (Worthington, Lakewood, N.J.), meshed and total cell suspensions were analyzed by flow cytometry for RFP expression. Briefly, tissue was initially perfused with collagenase (100 U) and incubated at 37° C. for 30 min. The collagenase supernatant was removed and quenched with 2% FBS. Tissue samples were then cut into ~2 mm squares, digested (collagenase, 400 U) with repeated agitation, filtered (nylon mesh), spun down (1,500 rpm), and pellets re-suspended in ice-cold 2% FBS.

TABLE 5

Experimental Groups

| Gr. # | Day 0 | | Day 21 | |
|---|---|---|---|---|
| | Viral transfer vector (i.v.) | NCs (i.v.) | Viral transfer vector (i.v.) | NCs (i.v.) |
| 1 | AAV-RFP | None | AAV-RFP | None |
| 2 | AAV-RFP | 50 µg of Rapa | AAV-RFP | None |
| 3 | AAV-RFP | None | AAV-RFP | 50 µg of Rapa |
| 4 | AAV-RFP | 50 µg of Rapa | AAV-RFP | 50 µg of Rapa |
| 5 | AAV-RFP | None | None | None |
| 6 | None | None | AAV-RFP | None |

Results

Figure 12:
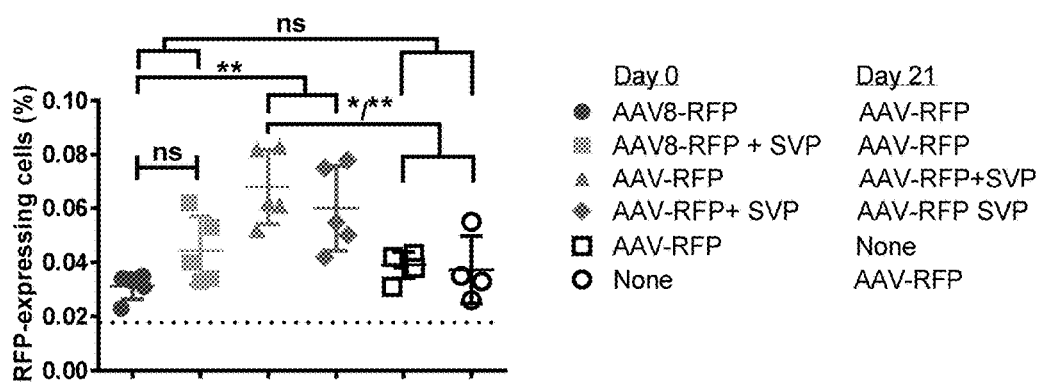
FIG. 12 shows RFP expression in livers of mice injected with AAV with or without synthetic nanocarriers comprising rapamycin at prime and/or boost. All cells in suspension have been analyzed for RFP expression with the exception of high side-scatter debris. Numbers shown represent the percentage of RFP-positive cells of the total parent population of liver cells.

Animals administered one or two injections of AAV8-RFP in the absence of NCs showed similar low levels of RFP expression at day 33 (FIG. 12). Mice treated with NCs concomitantly at the time of the first injection of AAV8-RFP showed a trend towards increased expression of RFP that was not statistically significant. In contrast, mice that were treated concomitantly with NCs at the time of the second injection of AAV8-RFP (day 21) showed a statistically significant increase in RFP expression. Mice that were treated with NCs at both day 0 and day 21 also showed a significant increase in RFP expression compared to control animals that received AAV8-RFP on days 0 and 21 in the absence of NCs.

The results demonstrate the benefit of administering synthetic nanocarriers coupled to an immunosuppressant in conjunction with a viral transfer vector for enhancing expression of the vector transgene. Such benefits were seen with concomitant administration of synthetic nanocarriers coupled to an immunosuppressant in conjunction with a viral transfer vector comprising a transgene encoding a protein for expression.

Example 17

Administration of a Viral Transfer Vector with a Gene Therapy Transgene with Synthetic Nanocarriers Coupled to Immunosuppressant Inhibits CD8+ T cell Activation Two successive intravenous (i.v.) inoculations of adeno-associated virus expressing recombinant green fluorescent protein (AAV-GFP) (Virovek, Hayward, Calif.) led to lower cytolytic T cell (CTL) activity against AAV capsid protein and GFP in vivo if nanocarrier-encapsulated immunosuppressant (NCs) was co-injected with both AAV8-GFP injections.

Experimental Methods

Male C57BL/6 mice were used (3 or 6 mice/group). Animals were injected with 200 µL of AAV-GFP or an admixture of AAV-GFP +NCs on day 0 and day 17 or 21 (see Table 6 below). Groups injected at days 0 and 21 (n=3 mice per group) were assayed for antigen-specific CTL activity at 28 days after the first injection (7 days after the second injection). Briefly, splenocytes from syngeneic naïve mice were labeled with either 0.5 µM, or 5 µM CFSE, resulting in $CFSE^{low}$ and $CFSE^{high}$ cell populations, respectively. $CFSE^{high}$ cells were incubated with 1 µg/mL dominant MHC class I-binding peptide from AAV capsid (sequence NSLANPGIA (SEQ ID NO: 1), amino acids 517-525) and dominant MHC class I peptide from GFP (HYLSTQSAL (SEQ ID NO: 2), aa 200-208) at 37° C. for 1 h, while CFSElow cells were incubated in medium alone. The control CFSElow cells and peptide-pulsed CFSEhigh target cells were mixed in a 1:1 ratio (2.0×107 cells total) and injected i.v. Eighteen hours after the injection of labeled cells, spleens were harvested, processed and analyzed by flow cytometry. Specific cytotoxicity was calculated based on a control ratio of recovery (RR) in naïve mice: (percentage of CFSElow cells)/(percentage of CFSEhigh cells). Percent specific lysis (%) =100×[1−(RR of cells from naive mice/RR of cells from immunized mice) or 100×[1−(RRnaive/RRimm)].

Groups injected at days 0 and 17 (n=6 mice per group) were assayed for antigen-specific IFN-γ production on d25 after the first injection (7 days after the second injection). Briefly, splenocytes were isolated, plated in wells with pre-absorbed anti-IFN-γ antibody and re-stimulated with AAV capsid or GFP peptides (1 µg/mL) for 7 days in vitro. ELISpots were developed by biotinylated anti-IFN-γ antibody and streptavidin-HRP, and spots were counted. Non-specific background was subtracted.

Amounts of AAV-GFP:$1 \times 10^{10}$ viral genomes (vg) at d0 prime, $5 \times 10^{10}$ vg at d21 boost.

Amounts of Nanocarrier-Encapsulated Immunosuppressant (Rapamycin or Rapa) Used:50 µg of nanocarrier-entrapped *Rapa* at both prime and boost (gr. 2).

TABLE 6

Experimental Groups

| | First Injection i.v. (Day 0) | | Second Injection i.v. (day 17 or 21) | |
|---|---|---|---|---|
| Gr. # | AAV8-GFP | NCs | Challenge | NCs |
| 1 | $1 \times 10^{10}$ vg | None | $5 \times 10^{10}$ vg | None |
| 2 | $1 \times 10^{10}$ vg | 50 µg rapamycin | $5 \times 10^{10}$ vg | 50 µg rapamycin |

Results

Figure 13:
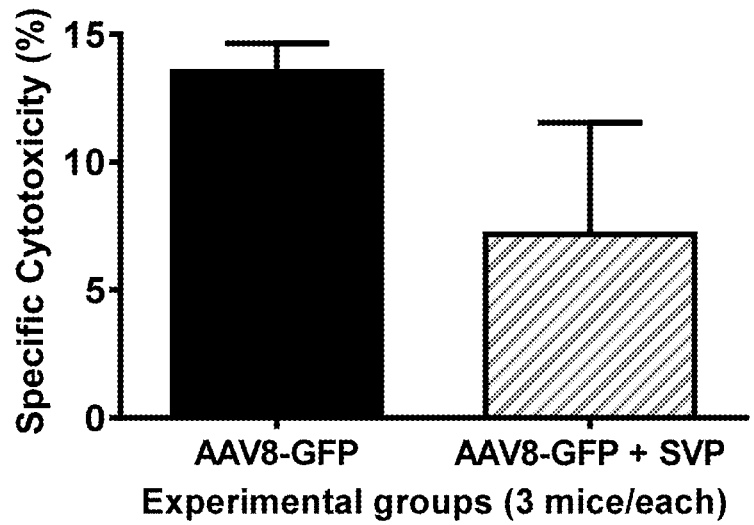
FIG. 13 shows cytotoxic activity in mice immunized with AAV-GFP alone or in combination with synthetic nanocarriers comprising rapamycin. Animals were injected with AAV8-GFP (i.v.) on days 0 and 21 with or without synthetic nanocarriers comprising rapamycin. Target cells pulsed with a combination of dominant cytotoxic peptides from AAV capsid protein and the GFP transgene were administered at 7 days after the last injection (day 28) and their viability measured 18 hours later and compared to that of non-peptide pulsed control cells.
Figure 14:
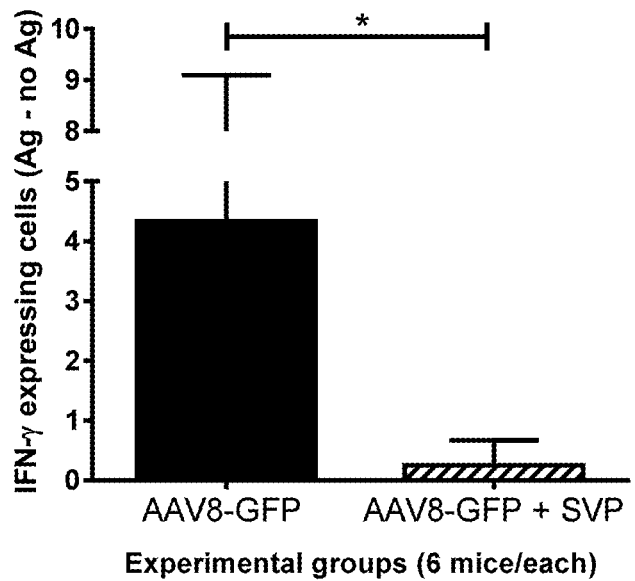
FIG. 14 shows AAV-specific IFN-γ production in mice immunized with AAV-GFP alone or in combination with synthetic nanocarriers comprising rapamycin. Animals were injected with AAV-GFP (i.v.) on days 0 and 17 with or without NCS. Splenocytes were isolated on day 25 and incubated in vitro with dominant MHC class I-binding peptide from AAV capsid protein for 7 days and then assayed by ELISpot with the same peptide. Each sample was run in duplicate and presented with background subtracted.
Figure 15:
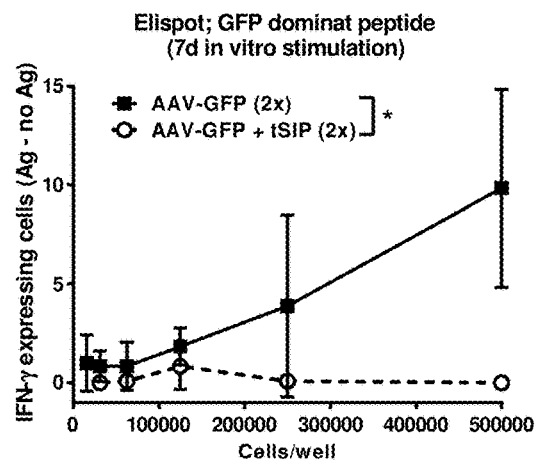
FIG. 15 shows GFP-specific IFN-γ production in mice immunized with AAV-GFP alone or in combination with synthetic nanocarriers comprising rapamycin. Animals were injected (i.v.) with AAV8-GFP on days 0 and 17 with or without synthetic nanocarriers comprising rapamycin. Splenocytes were isolated and incubated in vitro with MHC class I-binding peptide from GFP for 7 days and then assayed by ELISpot with the same peptide. Each sample was run in duplicate and presented with background subtracted.

Animals concomitantly treated with NCs showed lower levels of in vivo CTL activity against targets cells pulsed with a combination of AAV capsid and GFP dominant MHC class I peptides (FIG. 13). Similarly, mice concomitantly treated with NCs showed a significant reduction in antigen-specific IFN-γ-producing cells compared to the non-NCs-treated group (FIGS. 14 and 15). In particular, 4/6 mice demonstrated a recall response to the AAV capsid protein at 250,000 cells per well density, while no (0/6) mice responded to this peptide in the NCs-treated group (FIG. 14, p<0.05). Moreover, 3/6 mice in the AAV8-GFP-immunized group showed a response to an immunodominant GFP peptide, while no mice (0/6) responded to this peptide in the NCs-treated group (FIG. 15, p=0.01).

Collectively, it appeared that co-administration of AAV-GFP and NCs at prime and boost results in suppression of cytotoxic T cell responses against viral capsid and transgenic proteins.

Example 18

Administration of Viral Transfer Vector with a Gene Therapy Transgene with Synthetic Nanocarriers Comprising Immunosuppressant Experimental Methods Male C57BL/6 mice were used (5 mice/group). Animals were injected i.v. with $10^{10}$ vg of rAAV2/8-luciferase (rAAV2/8-Luc)) (produced in a manner similar to the methods provided herein such as in Example 21 or 22) or rAAV2/8-Luc+synthetic nanocarriers containing 100 µg rapamycin (NCs) on Day 0 (see Table 7 below). On day 14, all animals received an i.v. injection of $10^{10}$ vg of rAAV2/8 encoding human factor IX (hFIX) (rAAV2/8-hFIX)) (produced in a manner similar to the methods provided herein such as in Example 21 or 22). Sera were collected at various time points and assayed for anti-AAV antibody levels and hFIX protein levels by ELISA.

Figure 16:
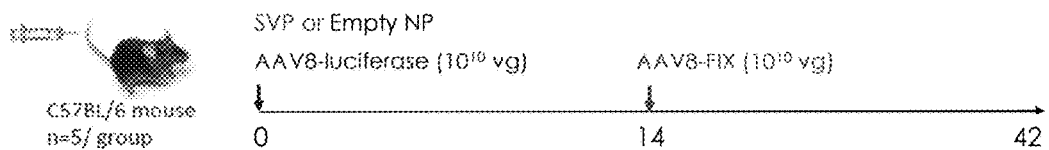
FIG. 16 shows the design for an experiment.
Figure 17:
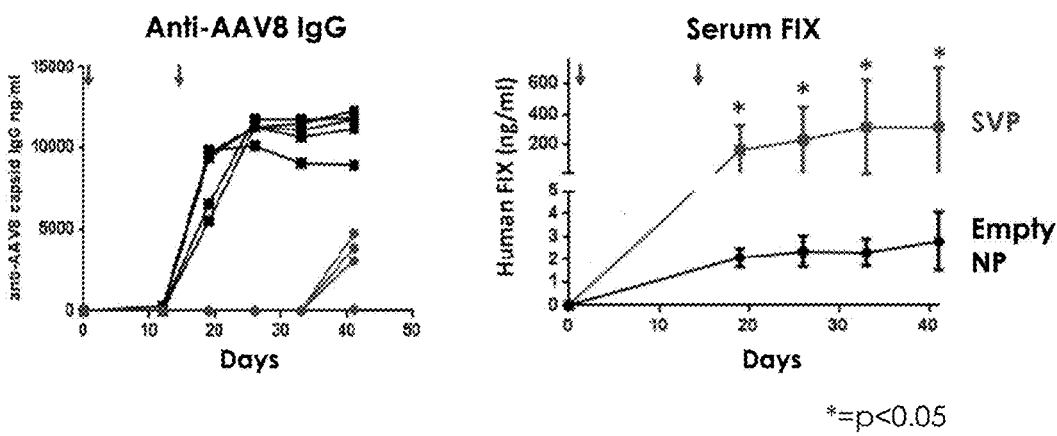
FIG. 17 shows results from an experiment where mice were injected with rAAV2/8-luciferase on day 0 with or without co-administration of synthetic nanocarriers carrying 100 μg of rapamycin (i.v.) and then challenged with an i.v. injection of AAV-hFIX on day 14. Sera was collected at various time points, as indicated, and assayed for antibodies against AAV8 (left) and for the levels of human factor IX protein (right).

FIG. 16 illustrates the protocol and timing of administration of synthetic nanocarriers comprising an immunosuppressant. Synthetic PLGA nanocarriers containing 100 µg rapamycin (NCs) or control empty nanoparticles (Empty NP) were administered i.v. concomitantly with rAAV2/8-Luc vector ($10^{10}$ vg) on Day 0 (N=5/group). All groups received an injection (i.v.) of rAAV2/8 vector encoding human coagulation factor IX (hFIX) on Day 14. The data show that a single administration of synthetic nanocarriers comprising immunosuppressant concomitantly administered with AAV8-Luc can prevent or delay the onset of anti-AAV8 antibodies (FIG. 17). Importantly, the concomitant administration of NCs with rAAV2/8-luciferase inhibited anti-AAV8 antibody formation sufficiently to enable efficient expression of hFIX from the rAAV2/8-hFIX administered on day 14. In contrast, animals treated with empty NP developed anti-AAV8 antibodies which prevented efficient expression of hFIX from the rAAV2/8-hFIX vector administered on day 14. These data indicate that concomitant administration of synthetic nanocarriers comprising immunosuppressant at the time of the first application of AAV enables efficacious repeat dosing of the same serotype of AAV.

TABLE 7

Treatment Groups

| Groups | Nanocarriers | rAAV2/8-Luc | rAAV2/8-FIX | N |
|---|---|---|---|---|
| 1 | NCs, D0 | D0 | D14 | 5 |
| 2 | Empty NP, D0 | D0 | D14 | 5 |

Example 19

Figure 18:
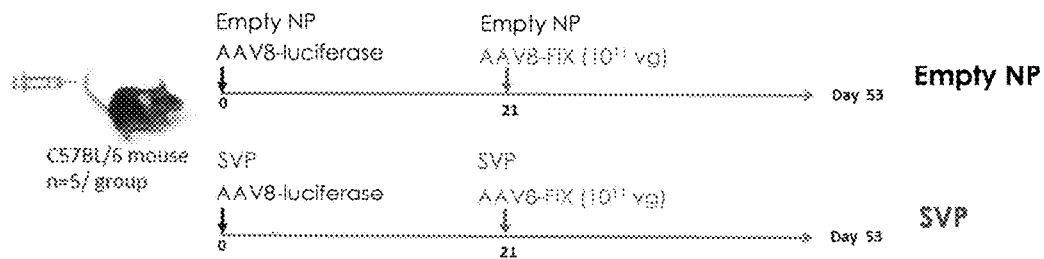
FIG. 18 shows the experimental design for an experiment.

Multiple Administrations of Viral Transfer Vector with a Gene Therapy Transgene with Synthetic Nanocarriers Comprising Immunosuppressant The experimental design is shown in FIG. 18. Male C57BL/6 mice were used (5 mice/group). Synthetic nanocarriers containing rapamycin (NCs) (100 µg rapamycin) were administered i.v. concomitantly with rAAV2/8-Luc vector) (produced in a manner similar to the methods provided herein such as in Example 21 or 22) ($1 \times 10^{11}$ vg) on day 0 (N=5/group) (Table 8). Mice were then challenged with rAAV2/8-hFIX (produced in a manner similar to the methods provided herein such as in Example 21 or 22) concomitantly administered with synthetic nanocarriers containing rapamycin (100 µg rapamycin) on day 21. The control group received empty NP instead of NCs on days 0 and 21.

TABLE 8

Treatment Groups

| Groups | Nanoparticles | rAAV2/8-Luc ($10^{11}$ vg) | rAAV2/8-FIX ($10^{11}$ vg) | N |
|---|---|---|---|---|
| 1 | NCs, d 0, 21 | d0 | d21 | 5 |
| 2 | Empty NP, d0, 21 | d0 | d21 | 5 |

Figure 19:
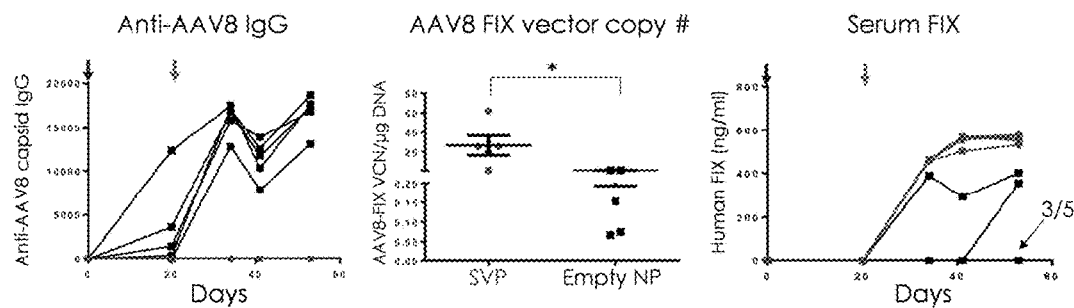
FIG. 19 shows results from an experiment where male C57BL/6 mice were injected (i.v.) with rAAV2/8-luciferase concomitantly with synthetic nanocarriers carrying 100 μg of rapamycin on day 0 and then injected with rAAV2/8-hFIX concomitantly with synthetic nanocarriers carrying 100 μg of rapamycin on day 21. Control animals were treated similarly but with empty nanocarriers instead of synthetic nanocarriers comprising rapamycin. Sera were collected at various time points, as indicated, and assayed by ELISA for antibodies against AAV (left) and for levels of human FIX protein (right). AAV2/8-FIX vector copy number in the liver (middle) was determined by PCR.

The results showed that concomitant administration of synthetic nanocarrier injections with both the first (rAAV2/8-Luc) and second (rAAV2/8-hFIX) injections of viral transfer vector inhibited the anti-AAV8 antibody response (FIG. 19, left panel) and reduced the titer of neutralizing antibodies to AAV8 (Table 9). The inhibition of the anti-AAV8 antibodies enabled higher levels of AAV2/8-hFIX vector copy numbers (FIG. 19, middle panel), which in turn provided for robust expression of the hFIX transgene (FIG. 19, right panel). Note that in the control group treated with empty nanoparticles, several animals had low levels of antibodies at day 20. Two of these animals had an intermediate level of vector copy numbers and some expression of hFIX in response to administration of rAAV2/8-hFIX on day 21. However three of the control animals showed very low vector copy numbers and no detectable levels of FIX expression.

Accordingly, it was demonstrated that multiple administrations of synthetic nanocarriers comprising immunosuppressant can completely prevent the induction of antigen-specific anti-AAV8 antibodies, allowing for high levels of transgene expression upon a second injection of AAV.

TABLE 9

Neutralizing anti-AAV antibody titers
AAV8 Neutralizing Antibody Titer

| Animal # | NCs Day 20 | Day 41 | Empty NP Day 20 | Day 41 |
|---|---|---|---|---|
| 1 | 1:3.16 | 1:31.6 | 1:31.6 | 1:1000 |
| 2 | <1:1 | 1:31.6 | 1:31.6 | 1:316 |
| 3 | <1:1 | 1:31.6 | 1:31.6 | 1:316 |
| 4 | <1:1 | 1:31.6 | 1:31.6 | 1:1000 |
| 5 | <1:1 | 1:31.6 | 1:31.6 | 1:1000 |

Example 20

Antigen Specificity

Figure 20:
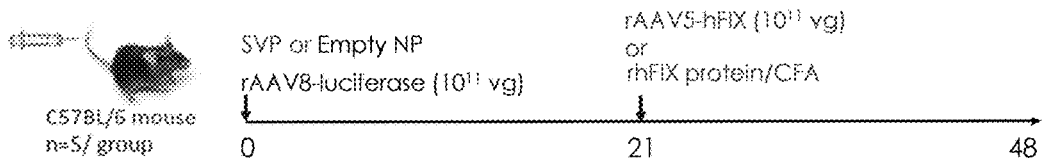
FIG. 20 shows the experimental design for an experiment.

The experimental design is shown in FIG. 20. Synthetic nanocarriers comprising immunosuppressant (100 µg rapamycin) or control empty nanoparticles were administered i.v. concurrently with rAAV2/8-Luc vector) (produced in a manner similar to the methods provided herein such as in Example 21 or 22) ($1 \times 10^{11}$ vg/mouse) on Day 0. On day 21 mice received either an i.v. injection of rAAV5-hFIX) (produced in a manner similar to the methods provided herein such as in Example 21 or 22) ($1 \times 10^{11}$ vg/mouse) or an i.m. injection of human Factor IX (hFIX) protein emulsified in complete Freund's adjuvant (CFA) (Table 10).

TABLE 10

Treatment Groups

| Groups | Nanoparticles | rAAV2/8-Luc ($10^{11}$ vg) | rAAV5-hFIX ($10^{11}$ vg) | FIX protein CFA | N |
|---|---|---|---|---|---|
| 1 | NCs, d0 | d0 | d21 | — | 5 |
| 2 | Empty NP, d0 | d0 | d21 | — | 5 |
| 3 | NCs, d0 | d0 | — | d21 | 5 |
| 4 | Empty NP, d0 | d0 | — | d21 | 5 |

Figure 21:
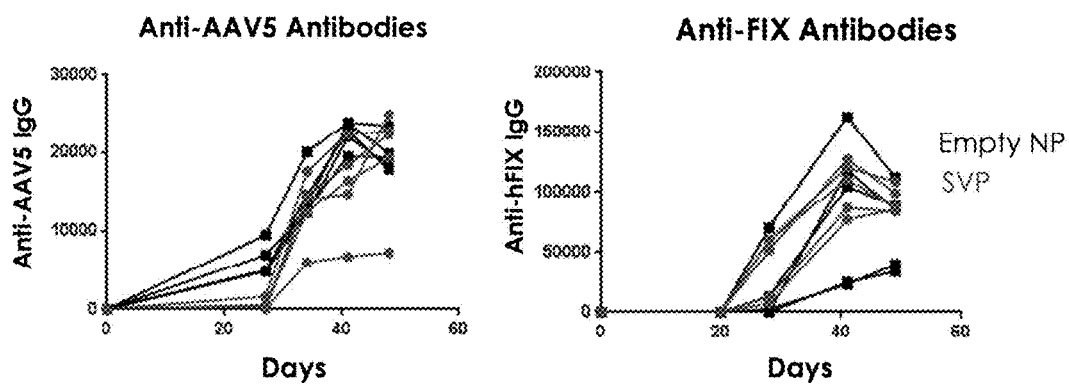
FIG. 21 provides results that showed that concomitant i.v. administration of synthetic nanocarriers carrying rapamycin with an rAAV2/8 vector (AAV2/8-Luc) on day 0 did not have a profound impact on the antibody response to an AAV5 vector (AAV5-hFIX) administered on day 21. In contrast, the results also showed that mice concomitantly treated with synthetic nanocarriers comprising rapamycin and rAAV2/8-Luc on day 0 showed a robust response to immunization with recombinant hFIX protein in complete Freund's adjuvant (CFA) on day 21.

The results showed that concomitant i.v. administration of synthetic nanocarrier carrying rapamycin with an rAAV2/8 vector (AAV2/8-Luc) on day 0 did not have a profound impact on the antibody response to an AAV5 vector (AAV5-hFIX) administered on day 21 (FIG. 21, left panel). The animals treated with the NCs containing rapamycin had a short delay in the anti-AAV5 antibody response compared to mice treated with empty NP, perhaps because of the presence of B cells in the empty NP-treated mice that were primed against AAV8 and crossreactive to AAV5. However the anti-AAV5 antibody response of the NCs-treated mice rapidly parallels the anti-AAV5 antibody response of the empty NP-treated group.

In contrast, animals that received AAV2/8-FIX on day 21 showed little or no anti-AAV8 antibodies. These data indicate that the effect of the NCs treatment on inhibiting anti-AAV antibody responses were specific to AAV serotype with which it was co-administered (i.e., AAV8) and does not render the mice chronically immunosuppressed. Similarly, mice concomitantly treated with NCs and rAAV2/8-Luc on day 0 showed a robust response to immunization with recombinant hFIX protein in complete Freund's adjuvant (CFA) on day 21 (FIG. 21, right panel). The anti-hFIX antibody response was indistinguishable from that of mice that were treated with empty NP instead of NCs on day 0. Accordingly, it was demonstrated that concomitant administration of synthetic nanocarriers comprising immunosuppressant with AAV does not result in chronic immunosuppression.

Example 21

AAV5 Transfer Vector with a Gene Therapy Transgene (Prophetic)

ART-I02 is produced as described previously (Matsushita T, et al. Gene Ther. 1998; 5: 938-945). The plasmid encodes any one of the transgenes provided herein under the control of the NF-κB promoter and a human growth hormone polyadenylation signal. The gene of interest may also be under the control of the cytomegalovirus (CMV) promoter. The transgene cassette is flanked by AAV-2 inverted terminal repeats and is packaged in capsid from AAV5 as described in Gao GP, et al. Proc Natl Acad Sci USA. 2002; 99: 11854-11859. The vector is purified by combined chromatography and cesium chloride density gradient centrifugation, resulting in empty capsid-free fractions. Vector titers can be determined by qPCR using specific primers and probe. Similarly, as an example, a rAAV5 vector can be produced coding for Firefly Luciferase.

Example 22

AAV2/8 and AAV2/5 Transfer Vector with a Gene Therapy Transgene (Prophetic)

An scAAV backbone plasmid is constructed by ligating MscIBsaI and BsaITsp45I fragments from AAV2-HCR-hAAT-FIX to the simian virus 40 late polyA (SV40 LpA). The resulting plasmid contains the modified AAV2 backbone with an intact 5' terminal resolution site (trs) and a deleted 3' trs. The LP1 enhancer/promoter can be constructed using standard polymerase chain reaction (PCR) methods with amplification of consecutive segments of the human apolipoprotein hepatic control region (HCR), the human alpha1antitrypsin (hAAT) gene promoter including the 5' untranslated region and cloned upstream of a modified SV40 small t antigen intron (SV40 intron) modified at positions 4582 (g to c), 4580 (g to c), 4578 (a to c), and 4561 (a to t) into the modified AAV2 backbone. The wild-type hFIX cDNA, or other cDNA of interest, without the 3' untranslated region (UTR) regions is PCR amplified from AAV-HCR-hAAT-hFIX and inserted downstream of the modified SV40 intron to make scAAV-LP1-hFIX. A codon-optimized hFIX is generated using codons most frequently found in highly expressed eukaryotic genes, synthesized as oligonucleotides, and subsequently assembled by ligation, PCR amplified, and sequenced prior to cloning into the AAVLP1 backbone to create sc-AAV-LP1-hFIXco. ss and scAAV vectors are made by the adenovirus-free transient transfection method.

AAV5-pseudotyped vector particles are generated using a chimeric AAV2 Rep-SCap packaging plasmid called pLT-RCO3, which is based on XX2 and pAAVS-2. Additionally, AAV8-pseudotyped vectors are made using the packaging plasmid pAAV8-2. AAV2/5 and 2/8 vectors are purified by the ion exchange chromatography method. Vector genome (vg) titers can be determined by quantitative slotblot using supercoiled plasmid DNA as standards. Such a viral vector can comprise any one of the transgenes as provided herein.

Example 23

AAV8 Transfer Vector with a Gene Therapy Transgene (Prophetic)

A mouse genomic Alb segment (90474003-90476720 in NCBI reference sequence:NC_000071.6) can be PCR-amplified and inserted between AAV2 inverted terminal repeats into BsrGI and SpeI restriction sites in a modified pTRUF backbone. An optimized P2A coding sequence preceded by a linker coding sequence (glycine-serine-glycine) and followed by anNheI restriction site can be into the Bpu10I restriction site. A codon-optimized F9 coding sequence can be inserted into the NheI site to get pAB269 that can serve in the construction of the rAAV8 vector. To construct the inverse control, an internal segment from the BsiWI restriction site to the NheI restriction site can be amplified using appropriate PCR primers. Final rAAV production plasmids can be generated using an EndoFree Plasmid Megaprep Kit (Qiagen).

rAAV8 vectors can be produced as described in Grimm, et al., J. Virol. 80, 426-439 (2006) using a $Ca_3(PO_4)_2$ transfection protocol followed by CsCl gradient purification. Vectors can be titred by quantitative dot blot.

As described in Barzel, et al., 364, Nature, Vol. 517, 2015, amelioration of the bleeding diathesis in haemophilia B mice was demonstrated using such vectors as described above. In particular, the vectors achieved integration into the albumin alleles in hepatocytes. F9 was produced from on-target integration, and ribosomal skipping was highly efficient. Stable F9 plasma levels were obtained, and treated F9-deficient mice had normal coagulation times.

Example 24

AAV9 Transfer Vector with a Gene Therapy Transgene (Prophetic)

Adenoviral constructs using a "first-generation" E1/E3-deleted replication-deficient adenovirus can be produced as described in Kypson, et al. J Thorac Cardiovasc Surg. 1998 and Akhter, et al. Proc Natl Acad Sci USA. 1997; 94:12100-12105. The $b_2AR$ construct (Adeno-$b_2AR$) and a transgene can be driven by an appropriate promoter. Large-scale preparations of adenoviruses can be purified from infected Epstein-Barr nuclear antigen-transfected 293 cells.

As described in Shah et al., Circulation. 2000; 101:408-414, rabbits that underwent percutaneous subselective catheterization of either the left or right coronary artery and infusion of adenoviral vectors such as those produced as above containing a marker transgene expressed the transgene in a chamber-specific manner. In addition, it was concluded that percutaneous adenovirus-mediated intracoronary delivery of a therapeutic transgene is feasible, and that acute global left ventricular function can be enhanced.

Example 25

Lentiviral Transfer Vector with a Gene Therapy Transgene (Prophetic)

The following can be prepared: a lentiviral expression plasmid containing a packaging sequence and a transgene inserted between the lentiviral LTRs to allow target cell integration; a packaging plasmid, encoding the pol, gag, rev and tat viral genes and containing the rev-response element; and a pseudotyping plasmid, encoding a protein, of a virus envelope gene. HEK 293T cells can be transfected by the foregoing. After transfection of HEK 293T cells, the lentiviral vectors can be obtained from the cell supernatant which contains recombinant lentiviral vectors.

Example 26

HIV Lentiviral Transfer Vector with a Gene Therapy Transgene (Prophetic)

An HIV lentiviral transfer vector is prepared according the methods of U.S. Publication No. 20150056696. An hPEDF CDS fragment is PCR amplified from cDNA of the human Retinal pigment epithelium cell strain ARPE-19 (American Type Culture Collection, ATCC) as a template and using appropriate primers. An alternative fragment can be similarly obtained for any one of the proteins described herein. The hPEDF fragment is obtained by gel recovery and ligated into the pLenti6.3/V5-TOPO® vector (Invitrogen) by TA cloning procedure following the manufacturer's instruction. The sequence of the ligated hPEDF fragment can be verified by sequencing.

Example 27

SIV Lentiviral Transfer Vector with a Gene Therapy Transgene (Prophetic)

An SIV lentiviral transfer vector is prepared according the methods of U.S. Publication No. 20150056696. A SIV gene transfer vector, a packaging vector, a rev expression vector, and a VSV-G expression vector are obtained, and an hPEDF fragment is introduced into the gene transfer vector. An alternative fragment can be similarly obtained for any one of the proteins described herein for introduction into the gene transfer vector.

The cell line 293T cells derived from human fetal kidney cells are seeded at a cell density of approximate $1 \times 10^7$ cells per plastic Petri dish having the diameter of 15 cm (cell density of 70-80% next day) and cultured in 20 ml of D-MEM culture medium (Gibco BRL) supplemented with 10% fetal bovine serum for 24 hrs. After 24 h of cultivation, the culture medium is replaced with 10 ml of OPTI-MEM culture medium (Gibco BRL).

For one petri dish, 10 μg of the gene transfer vector, 5 μg of the packaging vector, 2 μg of the rev expression vector and 2 μg of VSV-G expression vector are dissolved in 1.5 ml of OPTI-MEM medium, and 40 μl of PLUS Reagent reagent (Invitro Co.) is added. The resulting mixture is stirred and left at room temperature for 15 min. A dilute solution is obtained by diluting 60 μl of LIPOFECT AMINE Reagent with 1.5 ml of OPTI-MEM medium; the resulting mixture is stirred and left at room temperature for 15 min. The resulting DNA-complex is dropped onto the cells in the above-described Petri dish. The Petri dish is shaken carefully to achieve uniform mixing, and then incubated. 13 ml of D-MEM medium comprising 20% of fetal bovine serum is added. Supernatant is recovered.

Example 28

HSV Transfer Vector with a Gene Therapy Transgene (Prophetic)

An HSV transfer vector is prepared according the methods of U.S. Publication No. 20090186003. HSV-1 (F) strain is a low passage clinical isolate used as the prototype HSV-1 strain. M002, which expresses murine interleukin 12 (mIL-12) under the transcriptional control of the murine early-growth response-1 promoter (Egr-1), is constructed. Alternatively, similar constructs may be prepared encoding any one of the proteins described herein under the control of an appropriate promoter. The plasmids containing the p40 and p35 subunits of mIL-12 in pBluescript-SK+ (Stratagene) are obtained. The p40 subunit is removed by digestion with HindIII (5' end) and BamHI (3' end) and the p35 subunit is removed by digestion with NcoI (5' end) and EcoRI (3' end). The internal ribosome entry site, or IRES, sequence is amplified from vector pCITE-4a+ (Novagen, Madison, Wis.) using polymerase chain reaction (PCR) and appropriate primers. Plasmid pBS-IL12 is constructed by three-way ligation of the murine p40, murine p35 and IRES sequences into HindIII and EcoRI sites of pBS-SK+ such that the IRES sequence separates the p40 and p35 coding sequences.

A HSV shuttle plasmid pRB4878 can be prepared as previously described (Andreansky et al. (1998) Gene Ther. 5, 121-130). Plasmid 4878-IL12 is constructed as follows: pBS-mIL-12 is digested with XhoI and SpeI to remove a 2.2 kb fragment containing the entire IL-12 subunit coding regions, including the IRES, ends filled in using the Klenow fragment, and ligated into a blunted KpnI site located between the Egr-1 promoter and hepatitis B virus polyA sequences within pRB4878. M001 (tk–) and M002 (tk repaired at native locus) are constructed via homologous recombination as described previously (Andreansky et al. (1998) Gene Ther. 5, 121-130). Two tk-repaired viruses M002.29 and M002.211, are confirmed by Southern blot hybridization of restriction enzyme-digested viral DNAs which are electrophoretically separated on a 1% agarose, 1×TPE gel and transferred to a Zeta-Probe membrane (Bio-Rad). The blot is hybridized with the appropriate DNA probe labeled with alkaline phosphatase using the Gene Images AlkPhos Direct DNA labeling system (Amersham-Pharmacia Biotech, Piscataway, N.J.). IL-12 production is demonstrated by enzyme-linked immunosorbent assay (ELISA).

Example 29

Viral Transfer Vector with a CRISPR/Cas-9 Transgene (Prophetic)

Any one of the viral vectors described herein, such as in the above Examples, may be used to produce a viral transfer vector with a gene editing transgene. Alternatively, and as an example, the following provides a method for producing a viral transfer vector with a gene editing transgene that encodes Cas9, such as Cas9 wild-type (Type II).

HEK293T cells can be cultured in DMEM medium (Life Technologies, Darmstadt, Germany) containing 10% fetal bovine serum (Sigma, Steinheim, Germany), 100 U/mL penicillin and 100 μg/mL streptomycin (Life Technologies). Huh? and Hep56D cell media can additionally contain 1% non-essential amino acids (Life Technologies). Jurkat cells can be grown in RPMI 1640 medium (GE Healthcare, Pasching, Austria) containing 10% fetal bovine serum (Sigma), 100 U/mL penicillin, 100 μg/mL streptomycin, and 2 mM L-glutamine (all Life Technologies). All cell lines can be cultured at 37° C. and 5% CO2. For large-scale AAV vector production, HEK293T cells can be seeded in ten 15 cm2 dishes ($4 \times 10^6$ cells per dish). Two days later, they can be triple-transfected with (i) the AAV vector plasmid (encoding gRNA and/or Cas9), (ii) an AAV helper plasmid carrying AAV rep and cap genes, and (iii) an adenoviral plasmid providing helper functions for AAV production.

The AAV cap gene can be either derived from the synthetic isolate AAV-DJ (Grimm, et al., J. Virol. 2008, 82, 5887-5911) or from a new variant AAVrh10A2. Briefly, AAVrh10A2 can be created through insertion of a seven amino acid long peptide into an exposed region of the capsid of AAV serotype rh10. Further details on AAV production plasmids and protocols can be performed as reported in Börner, et al., Nucleic Acids Res. 2013, 41, e199 and Grimm, Methods 2002, 28, 146-157. To generate small-scale AAV stocks, $2 \times 10^5$ HEK293T cells per well can be seeded in 6-well plates and the next day triple-transfected with the aforementioned plasmids. Three days later, the cells can be scraped off into the media, collected via 10 min centrifugation at 1500 rpm, resuspended in 300 μL 1×PBS (Life Technologies) and subjected to three freeze-thaw cycles in liquid nitrogen and at 37° C. A 10 min centrifugation can be performed at 13,200 rpm to remove cell debris, and supernatants containing viral transfer vector particles can be used directly in transduction experiments or frozen at −20° C.

For small-scale transfections and subsequent T7 assays, 2.8×10⁴ HEK293T or 1.2×10⁴ Huh7 cells can be seeded per well in a 96-well plate and the next day transfected using lipofectamine 2000 (Life Technologies) following the manufacturer's recommendations for this format (200 ng DNA and 0.5 µL lipofectamine 2000, each in 25 µL serum-free medium). The 200 ng DNA can consist of an all-in-one Cas9/gRNA vector, or, in the case of separate Cas9 and gRNA constructs, of 100 ng of each. To obtain lysates for Western blotting, HEK293T cells can be transfected in 24-well plates (one well per lysate), using lipofectamine 2000 according to the manufacturer's recommendations for this format. In transduction experiments, cells can be grown in 96-well plates and transduced with either 10 µL non-purified AAV or with purified vector 1 day after seeding. Following a three (transfections) to five (transductions) day incubation, the cells can be lysed with DirectPCR Lysis Reagent Cell (PeqLab, Erlangen, Germany) supplemented with 0.2 µg/mL proteinase K (Roche, Mannheim, Germany) following the manufacturer's protocol.

As described in Senís, et al. Biotechnol. J. 2014, 9, 1402-1412, plasmids and vectors such as those above can achieve delivery of the CRISPR components—Cas9 and chimeric g(uide) RNA. In addition, it was demonstrated that Cas9 expression could be directed to or away from hepatocytes, using a liver-specific promoter or a hepatic miRNA binding site, respectively. Further evidence was provided that such vectors can be used for gene engineering in vivo. This was accomplished in the exemplified liver of adult mice.

Example 30

Viral Transfer Vector with a Cas9 Variant Transgene (Prophetic)

The methodology in Example 30 can also be used to produce a viral transfer vector with a gene editing transgene, such as a transgene encoding a Cas9 variant, such as any one of the Cas9 variants described herein. Alternatively, any one of the other viral vectors described herein, may be used instead to produce such a viral transfer vector. Any one of the Cas9 variants provided can be encoded by any one of the gene editing transgenes provided herein.

To make Cas9 variants, the human codon-optimized *streptococcus pyogenes* Cas9 nuclease with NLS and 3×FLAG tag (Addgene plasmid 43861) can be used as the wild-type Cas9 expression plasmid. PCR products of wild-type Cas9 expression plasmid as template with Cas9_Exp primers can be assembled with Gibson Assembly Cloning Kit (New England Biolabs) to construct Cas9 and FokI-dCas9 variants. Expression plasmids encoding a single gRNA construct (gRNA G1 through G13) can also be cloned.

Example 31

Viral Transfer Vector with a Zinc Finger Nuclease Transgene (Prophetic)

Any one of the viral vectors described herein, such as in the above Examples, may be used to produce a viral transfer vector with a gene editing transgene that encodes a zinc finger nuclease. Alternatively, and as an example, the following provides a method for producing such a viral transfer vector with a gene editing transgene.

TRBC- and TRAC-ZFNs can be designed and assembled as described in Urnov, et al. Nature 435, 646-651 (2005). The recognition helices used can be as provided Provasi, et al., Nature Medicine, Vol. 18, No. 5, May 2012. Lentiviral vectors encoding TRBC- and TRAC-ZFNs can be generated from the HIV-derived self-inactivating transfer construct pCCLsin.cPPT.SFFV.eGFP.Wpre, which can be packaged by an integrase-defective third generation packaging construct carrying the D64V mutation in the HIV integrase and pseudotyped by the VSV envelope. The Ad5/F35 adenoviral vectors can be generated on an E1-E3-deleted backbone. The ZFNs targeting either the TRBC or TRAC gene can be linked using a 2A peptide sequence and cloned into the pAdEasy-1/F35 vector under the control of an appropriate promoter, and the Ad5/F35 virus for each construct can be generated using TREx 293T cells. Lentiviral vectors encoding both WT1-specific TCR chains and single α21 or β21 WT1-specific TCR chains from the bidirectional self-inactivating transfer vector pCCLsin.cPPT.Δ LNGFR.minCMV.hPGK.eGFP.Wpre and from pCCLsin.cPPT.hPGK.eGFP.Wpre can be generated and packaged by an integrase-competent third-generation construct and pseudotyped by the VSV envelope.

Using vectors such as those above, and as described in Provasi, et al., Nature Medicine, Vol. 18, No. 5, May 2012, it has been shown that ZFNs promoted the disruption of endogenous TCR β- and α-chain genes. Lymphocytes treated with ZFNs lacked surface expression of CD3-TCR and expanded with the addition of interleukin-7 (IL-7) and IL-15. Further, after lentiviral transfer of a TCR specific for the Wilms tumor 1 (WT1) antigen, the TCR-edited cells expressed new TCR at high levels (also as described in Provasi, et al., Nature Medicine, Vol. 18, No. 5, May 2012).

Example 32

Viral Transfer Vector with a Zinc Finger Nuclease Transgene (Prophetic)

Zinc finger nucleases (ZFNs) targeting the hF9mut locus and F9-targeting vectors can be prepared as described in Li, et al. Nature. 2011; 475(7355):217-221. Such vectors have been shown to be successfully used for in vivo gene targeting in a neonatal mouse model of hemophilia B (HB). Systemic codelivery of the AAV vectors, encoding the ZFN pair targeting the human F9 gene and a gene-targeting vector with arms of homology flanking a corrective cDNA cassette resulted in the correction of a defective hF9 gene engineered into the mouse genome in the livers of such mice. Further, stable levels of human factor IX expression sufficient to normalize clotting times was achieved.

Example 33

Viral Transfer Vector with a Meganuclease Transgene (Prophetic)

Any one of the viral vectors described herein, such as in the above Examples, may be used to produce a viral transfer vector with a gene editing transgene that encodes a meganuclease. Alternatively, and as an example, the following describes a general methodology for producing such a viral transfer vector with a gene editing transgene. The meganuclease may be any one of the meganucleases provided in U.S. Publication Nos. 20110033935 and 20130224863.

In some embodiments, particular viral genes are inactivated to prevent reproduction of the virus. Preferably, in some embodiments, a virus is altered so that it is capable only of delivery and maintenance within a target cell, but does not retain the ability to replicate within the target cell or tissue. One or more DNA sequences encoding a meganuclease can be introduced to the altered viral genome, so as to produce a viral genome that acts like a vector. In some embodiments, the viral vector is a retroviral vector such as, but not limited to, the MFG or pLJ vectors. An MFG vector is a simplified Moloney murine leukemia virus vector (MoMLV) in which the DNA sequences encoding the pol and env proteins are deleted to render it replication defective. A pll retroviral vector is also a form of the MoMLV (see, e.g., Korman et al. (1987), Proc. Nat'l Acad. Sci., 84:2150-2154). In other embodiments, a recombinant adenovirus or adeno-associated virus can be used to produce a viral vector.

Example 34

Viral Transfer Vector with an Exon Skipping Transgene (Prophetic)

Any one of the viral vectors described herein, such as in the above Examples, may be used to produce a viral transfer vector with an exon skipping transgene. Alternatively, and as an example, the following provides a method for producing a viral transfer vector with a specific exon skipping transgene.

A three-plasmid transfection protocol can be used with pAAV(U7smOPT-SD23/BP22) and pAAV(U7smOPT-scr) plasmids for generation of single-strand AAV1-U7ex235 and AAV1-U7scr; and scAAV-U7ex23 plasmid for self-complementary scAAV9-U7ex239. pAAV(U7smOPT-scr) plasmid can contain the non specific sequence GGTGTAT-TGCATGATATGT (SEQ ID NO: 3) that does not match to any murine cDNAs.

Use of a viral transfer vector produced according to the above, as described in Le Hir et al., Molecular Therapy vol. 21 no. 8, 1551-1558 August 2013 showed that such a vector can be used to restore dystrophin. However, the restoration decreased significantly between 3 and 12 months, which was correlated with viral genome loss. Accordingly, the compositions and methods provided herein can help maintain the effect of such a treatment.

Example 35

Viral Transfer Vector with an Exon Skipping Transgene (Prophetic)

Clone U1#23 can be obtained by inverse PCR on the human U1 snRNA gene, with oligos mU1 anti5 (5'-CGAAATTTCAGGTAAGCCGAGGTTATGAGATCT-TGGGCCTCTGC-3' (SEQ ID NO: 4)) and mU1anti3 (5'-GAACTTTGCAGAGCCTCAAAATTAAATAGGGCA-GGGGAGATACCATGATC-3' (SEQ ID NO: 5)). The antisense-containing insert can be amplified from corresponding plasmid with oligos U1cas-up-NheI (5'-CTAGCTAGCGG-TAAGGACCAGCTTCTTTG-3' (SEQ ID NO:6)) and U1cas-down-NheI (5'-CTAGCTAGCGGTTAGCGTACA-GTCTAC-3' (SEQ ID NO: 7)). The resulting fragment can be NheI-digested and cloned in the forward orientation of the pAAV2.1-CMV-EGFP plasmid.

AAV-U1#23 vector can be produced by triple transfection of 293 cells, purified by CsCl2 ultracentrifugation and titered by using both real-time PCR-based and dot-blot assays. The number of green-forming units can be assessed by serial dilution on 293 cells. AAV vector can be produced by the AAV TIGEM Vector Core.

Six-week-old mdx mice can be administered with 3-4× $10^{12}$ genome copies of AAV vector via tail vein. Six and 12 weeks after virus administration, animals can be killed, and muscles from different districts can be harvested. EGFP analysis and dissections can be performed under a fluorescent stereomicroscope (Leica MZ16FA).

Use of a viral transfer vector produced according to the above, as described in Denti et al., 3758-3763, PNAS, Mar. 7, 2006, vol. 103, no. 10, resulted in persistent exon skipping in mdx mice by tail vein injection. Systemic delivery of the vector resulted in effective body-wide colonization, significant recovery of functional properties in vivo, and lower creatine kinase serum levels. The results suggest that there was a decrease in muscle wasting.

Example 36

Viral Transfer Vector with an Exon Skipping Transgene (Prophetic)

Different U7snRNA constructs specific to certain exons can be engineered, such as from U7smOPT-SD23/BP22 (modified murine U7snRNA gene). Antisense sequences targeting certain exons can be replaced by antisense sequences targeting exons of dystrophin mRNA that induce exon skipping as antisense oligonucleotides. Sequences can be inserted into U7snRNA constructs. Resulting U7snRNA fragments can then be introduced either in a lentiviral vector construct for further lentiviral production or into an AAV vector construct for AAV production.

Lentiviral vectors can be based on pRRLcPPT-hPGK-eGFP-WPRE constructs where the hPGK-GFP cassette is removed and replaced with the U7snRNA construct. Lentiviral vectors can be generated by transfection into 293T cells of a packaging construct, pCMVΔR8.74, a plasmid producing the vesicular stomatosis virus-G envelope (pMD.G) and the vector itself as previously described. Viral titers (infectious particles) can be determined by transduction of NIH3T3 cells with serial dilutions of the vector preparation in a 12-well plate. Seventy-two hours later, genomic DNA from transduced cells can be extracted using a genomic DNA purification kit (Qiagen, Crawley, UK). The infectious particles titer (infectious particle/ml) can be determined by quantitative real-time PCR as described elsewhere.

For subsequent AAV vector production, different U7snRNA fragments can be introduced at the XbaI site of the pSMD2 AAV2 vector. AAV2/1 pseudotyped vectors can be prepared by cotransfection in 293 cells of pAAV2-U7snRNA, pXX6 encoding adenovirus helper functions and pAAV1pITRCO2 that contains the AAV2 rep and AAV1 cap genes. Vector particles can be purified on Iodixanol gradients from cell lysates obtained 48 hours after transfection and titers can be measured by quantitative real time PCR.

As described in Goyenvalle, et al. The American Society of Gene & Cell Therapy, Vol. 20 No. 6, 1212-1221 June 2012, viral transfer vectors such as those produced and encoding U7 small-nuclear RNAs with the above methods can induce efficient exon skipping both in vitro and in vivo.

Example 37

Viral Transfer Vector with an Exon Skipping Transgene (Prophetic)

An HSV transfer vector can prepared according the methods of U.S. Publication No. 20090186003 and Example 28 above except that the methodology can be altered so that the transgene is instead an exon skipping transgene. The exon skipping transgene may be any one of such transgenes as described herein or otherwise known in the art.

Example 38

Viral Transfer Vector with an Exon Skipping Transgene (Prophetic)

An HIV lentiviral transfer vector is prepared according the methods of U.S. Publication No. 20150056696 and Example 26 above except that the methodology can be altered so that the transgene is instead an exon skipping transgene. The exon skipping transgene may be any one of such transgenes as described herein or otherwise known in the art.

Example 39

Viral Transfer Vector with a Gene Expression Modulating Transgene (Prophetic)

Any one of the viral vectors described herein, such as in the above Examples, may be used to produce a viral transfer vector with a gene expression modulating transgene. Alternatively, and as an example, the following provides a method for producing a viral transfer vector with a specific gene expression modulating transgene.

A viral transfer vector is produced according to the methods described in Brown et al., Nat Med. 2006 May; 12(5):585-91. Briefly, a plasmid is constructed using reverse transcription of RNA, quantitative PCR analysis to quantify the concentration of mRNA, and GAPDH expression for normalization. VSV-pseudotyped third-generation lentiviral vectors (LVs) are produced by transient four-plasmid cotransfection into 293T cells and purified by ultracentrifugation. Vector particles can be measured by HIV-1 gag p24 antigen immunocapture.

As described in Brown et al., Nat Med. 2006 May; 12(5):585-91, such lentiviral vectors encoding target sequences of endogenous miRNAs were shown to result in the production of miRNAs that could segregate gene expression in different tissues. Evidence of miRNA regulation was provided and demonstrates that such vectors may be used in therapeutic applications.

Example 40

Viral Transfer Vector with a Gene Expression Modulating Transgene (Prophetic)

To produce an AAV2/1 serotype vector encoding an miRNA-based hairpin against a gene (e.g., huntingtin gene; AAV2/1-miRNA-Htt), the cDNA for the specified gene (e.g., human HTT), can be cloned into a shuttle plasmid containing the AAV2 inverted terminal repeats (ITRs) and a 1.6-kb cytomegalovirus enhancer/chicken b-actin (CBA) promoter. Control vectors can also be developed and contain either an empty vector backbone (e.g., AAV2/1-Null) or express a reporter such as enhanced green fluorescent protein under the control of the same promoter (AAV2/1-eGFP). Viral transfer vectors can be generated by triple-plasmid cotransfection of a cell line, such as human 293 cells, and the recombinant virions can then be column-purified as previously described in Stanek et al., Human Gene Therapy. 2014; 25:461-474. The resulting titer of AAV2/1-miRNA-Htt can then be determined using quantitative PCR.

Data generated using such viral transfer vectors, as described in Stanek et al., Human Gene Therapy. 2014; 25:461-474, demonstrated that AAV-mediated RNAi can be effective at transducing cells in the striatum and can partially reduce the levels of both wild-type and mutant Htt in this region.

Example 41

Viral Transfer Vector with a Gene Expression Modulating Transgene (Prophetic)

The CD81 gene can be amplified by reverse transcription. cDNA can be PCR amplified with appropriate primers. The forward primer can contain a BamHI (Biolabs, Allschwill, Switzerland) restriction site followed by a 5' CD81 cDNA-specific sequence; the reverse primer can contain a 3' CD81 cDNA-specific sequence, a 6 His-tag, a stop codon and an Xho I (Biolabs) restriction site. The PCR product can be digested and cloned into similar sites in pTK431. The pTK431 is a self-inactivating HIV-1 vector which contains the entire tet-off-inducible system, the central polypurine tract (cPPT) and the woodchuck hepatitis virus post-transcriptional regulatory element. Plasmids can be $CsCl_2$ purified.

Targets can be designed according to the CD81 mRNA sequence based on Hannon's design criterion (katandin.c-shl.org:9331/RNAi/html/rnai.html). Using the pSilencer 1.0-U6 (Ambion) as a template and a U6 promoter-specific forward primer containing a restriction site, each shRNA target can be added to the mouse U6 promoter by PCR. The PCR product can be digested, cloned into similar sites in pTK431 and sequenced to verify the integrity of each construct.

The vector plasmids, together with a packaging construct plasmid pANRF and the envelope plasmid pMDG-VSVG, can be cotransfected into HEK293T cells to produce viral particles. The viral titres can be determined by p24 antigen measurements (KPL, Lausanne, Switzerland).

As shown in Bahi, et al. J. Neurochem. (2005) 92, 1243-1255, lentiviruses expressing short hairpin RNA (shRNA) targeted against CD81 (Lenti-CD81-shRNAs) resulted in gene silencing after infection of HEK293T cells in vitro. In addition, in vivo delivery of Lenti-CD81-shRNA resulted in silencing of endogenous CD81.

Example 42

Viral Transfer Vector with a Gene Expression Modulating Transgene (Prophetic)

Any one of the viral vectors described herein, such as in the above Examples, may be used to produce a viral transfer vector with a gene expression modulating transgene that encodes a RNAi agent. An example of a RNAi agent that can be encoded by a gene expression modulating transgene as provided herein is described below.

An expression construct can include a promoter driving the expression of three or more individual shRNA species. The synthesis of small nuclear RNAs and transfer RNAs can be directed by RNA polymerase III (pol III) under the control of pol III-specific promoters. Because of the relatively high abundance of transcripts directed by these regulatory elements, pol III promoters, including those derived from the U6 and H1 genes, can be used to drive the expression of 1-×RNAi (see, e.g., Domitrovich and Kunkel. Nucl. Acids Res. 31(9): 2344-52 (2003); Boden, et al. Nucl. Acids Res. 31(17): 5033-38 (2003a); and Kawasaki, et al. Nucleic Acids Res. 31(2): 700-7 (2003)). RNAi expression constructs using the U6 promoter can comprise three RNAi agents targeting three different regions of the HCV genome. Further examples of RNAi agents that may be encoded by a gene expression modulating transgene include any one of the RNAi agents described herein.

Example 43

Viral Transfer Vector with a Gene Expression Modulating Transgene (Prophetic)

Any one of the viral vectors described herein, such as in the above Examples, may be used to produce a viral transfer vector with a gene expression modulating transgene that encodes a Serpinal RNAi agent, such as one of such agents described in U.S. Patent Publication No. 20140350071. A viral transfer vector with such a transgene can be produced following similar methodology as provided herein or otherwise known in the art.

For example, adeno-associated virus (AAV) vectors may be used (Walsh et al., Proc. Soc. Exp. Biol. Med. 204:289-300 (1993); U.S. Pat. No. 5,436,146). The iRNA can be expressed as two separate, complementary single-stranded RNA molecules from a recombinant AAV vector having, for example, either the U6 or H1 RNA promoters, or the cytomegalovirus (CMV) promoter. Suitable AAV vectors for expressing the dsRNA featured in the invention, methods for constructing the recombinant AV vector, and methods for delivering the vectors into target cells are described in Samulski R et al. (1987), J. Virol. 61: 3096-3101; Fisher K J et al. (1996), J. Virol. 70: 520-532; Samulski R et al. (1989), J. Virol. 63: 3822-3826; U.S. Pat. No. 5,252,479; U.S. Pat. No. 5,139,941; International Patent Application No. WO 94/13788; and International Patent Application No. WO 93/24641, the entire disclosures of such information are herein incorporated by reference.

Example 44

Establishing an Anti-Viral Transfer Vector Attenuated Response in a Subject (Prophetic)

Any one of the viral transfer vectors provided herein, such as any one of the Examples, is administered concomitantly, such as simultaneously i.v., i.m., s.c. or i.p., with any one of the antigen-presenting cell targeted immunosuppressants as provided herein, such as any one of the Examples, that is also administered i.v., i.m., s.c. or i.p., respectively. The administration occurs according to a protocol, including at least the frequency and dose of the viral transfer vector and antigen-presenting cell targeted immunosuppressant, that establishes an anti-viral transfer vector attenuated response in the subject. The subject may be any one of the subjects described herein, such as one that does not have a pre-existing immunity to the viral transfer vector or one in which repeated administration of the viral transfer vector is desired.

In some embodiments, when the anti-viral transfer vector attenuated response is a T cell response against the viral transfer vector, the viral transfer vector is administered to the subject without an antigen-presenting cell targeted immunosuppressant prior to the concomitant administration of the antigen-presenting cell targeted immunosuppressant and viral transfer vector. In such embodiments, one or more repeat doses of the viral transfer vector is administered to the subject subsequent to both the concomitant administration and the administration of the viral transfer vector prior thereto.

In some embodiments, when the anti-viral transfer vector attenuated response is a B cell response against the viral transfer vector, the subject is not administered the viral transfer vector prior to the concomitant administration of the viral transfer vector and antigen-presenting cell targeted immunosuppressant. In such embodiments, one or more repeat doses of the viral transfer vector is administered to the subject and each repeat dose is concomitantly administered with the antigen-presenting cell targeted immunosuppressant.

In other embodiments, when the anti-viral transfer vector attenuated response is an anti-viral transfer vector antibody response, the subject is not administered the viral transfer vector prior to the concomitant administration of the viral transfer vector and antigen-presenting cell targeted immunosuppressant. In such embodiments, one or more repeat doses of the viral transfer vector is administered to the subject and each repeat dose is concomitantly administered with the antigen-presenting cell targeted immunosuppressant.

The method for determining the level of antibodies may be with the use of an ELISA assay. Assays for antigen-specific B cell or T cell recall responses include, but are not limited to, ELISpot, intracellular cytokine staining, cell proliferation, and cytokine production assays. In any one of the embodiments, the anti-viral transfer vector attenuated response is evaluated after the concomitant administration of the viral transfer vector and the antigen-presenting cell targeted immunosuppressant.

In any one of the embodiments, a protocol for establishing the anti-viral transfer vector attenuated response may be determined. In such an embodiment, the protocol is determined in another subject, such as a test subject. The protocol so determined can be used to treat other subjects in need of treatment with the viral transfer vector.

Example 45

Determining a Level of Pre-Existing Immunity in a Subject Prior to Administration of a Viral Transfer Vector (Prophetic)

A sample, such as a blood sample, may be obtained from a subject that is in need of treatment with a viral transfer vector as provided herein, such as the viral transfer vector of any one of the viral transfer vectors provided herein, such as in any one of the Examples.

With the sample from the subject, the level of antibodies, such as neutralizing antibodies or antigen recall responses of immune cells, such as T cells or B cells, can be determined. The method for determining the level of antibodies may be with the use of an ELISA assay. Assays for antigen-specific B cell or T cell recall responses include, but are not limited to, ELISpot, intracellular cytokine staining, cell proliferation, and cytokine production assays. The recall response can be assessed by contacting the sample with the viral transfer vector or an antigen thereof. Alternatively, the recall response can also be assessed by taking the sample from the subject after administration of the viral transfer vector or an antigen thereof to the subject and then determining the level of antibodies or a B cell or T cell recall response that was generated.

In some embodiments, where the subject does not have a pre-existing immunity to the viral transfer vector, determined by the measurement of a level of anti-viral transfer vector antibodies in the subject (or a B cell response), the subject is administered, i.v., i.m., s.c. or i.p., any one of the viral transfer vectors provided herein, such as in any one of the Examples, concomitantly, such as simultaneously, with any one of the antigen-presenting cell targeted immunosuppressants provided herein, such as in any one of the Examples. The antigen-presenting cell targeted immunosuppressant is administered by the same route.

In other embodiments, where the subject does not have a pre-existing immunity to the viral transfer vector, determined by the level of a T cell response against the viral transfer vector in the subject, the antigen-presenting cell targeted immunosuppressant and viral transfer vector are concomitantly, such as simultaneously, administered, i.v., i.m., s.c. or i.p., to the subject after the subject is administered a dose of the viral transfer vector without concomitant administration of the antigen-presenting cell targeted immunosuppressant.

In any one of the embodiments, one or more repeat doses of the viral transfer vector is/are administered to the subject. These repeat doses may be concomitantly administered with the antigen-presenting cell targeted immunosuppressant.

Example 46

Escalating Transgene Expression of a Viral Transfer Vector in a Subject (Prophetic)

Any one of the viral transfer vectors provided herein, such as in any one of the Examples, is administered concomitantly, such as simultaneously, i.v., i.m., s.c. or i.p., with any one of the antigen-presenting cell targeted immunosuppressants as provided herein, such as in any one of the Examples, according to a frequency and dosing that escalates transgene expression (the transgene being delivered by the viral transfer vector). This can be determined by measuring transgene protein concentrations in various tissues or systems of interest in the subject. Whether or not transgene expression is escalated can be determined according to a method, such as that described in the Examples above. The administration occurs according to the frequency and dose of the viral transfer vector and antigen-presenting cell targeted immunosuppressant, that escalates transgene expression in the subject. The subject may be any one of the subjects described herein, such as one that does not have a pre-existing immunity to the viral transfer vector or one in which repeated administration of the viral transfer vector is desired.

In any one of the embodiments, the frequency and dose that achieves escalating transgene expression is determined in another subject, such as a test subject. This can also be determined by measuring transgene protein concentrations in various tissues or systems of interest in the other subject, such as with a method as described above. If the frequency and dose achieves escalated transgene expression, as determined by the measured transgene protein concentrations, in the other subject, the concomitant, such as simultaneous, administration of the viral transfer vector and antigen-presenting cell targeted immunosuppressant according to the frequency and dose can be used to treat other subjects in need of treatment with the viral transfer vector.

Example 47

Repeated, Concomitant Administration with Lower Doses (Prophetic)

As provided herein, a subject can be evaluated for the level of a pre-existing immunity to any one of the viral transfer vectors provided herein, such as any one of the viral transfer vectors any one of the Examples. Alternatively, a clinician may evaluate a subject and determine whether or not, if administered the viral transfer vector, the subject is expected to develop an anti-viral transfer vector immune response if the viral transfer vector is repeatedly administered to the subject. This determination may be made based on the likelihood that the viral transfer vector will produce such a result and may be based on such a result in other subjects, such as test subjects, information about the virus that was used to generate the viral transfer vector, information about the subject, etc. Generally, if the expectation is that an anti-viral transfer vector immune response is the likely result, the clinician selects a certain dose of the viral transfer vector as a result of the expectation. However, in light of the inventor's findings, a clinician may now select and use lower doses of the viral transfer vector than would have been selected for the subject. Benefits of lower doses can include reduced toxicity associated with dosing of the viral transfer vector, and reduction of other off-target effects.

Accordingly, any one of the subjects provided herein can be treated with repeated, concomitant, such as simultaneous, administration of any one of the viral transfer vectors provided herein and any one of the antigen-presenting cell targeted immunosuppressants provided herein where the doses of the viral transfer vector are selected to be less than the dose of the viral transfer vector that would have been selected for the subject if the subject were expected to develop anti-viral transfer vector immune responses due to repeated dosing of the viral transfer vector. Each dose of the viral transfer vector of the repeated, concomitant administration may be less than what would have otherwise been selected.

What is claimed is:

1. A method comprising:

attenuating an anti-gene expression modulating viral transfer vector response, wherein the anti-gene expression modulating viral transfer vector response is a T cell response, by first administering to a subject a gene expression modulating viral transfer vector without an antigen-presenting cell targeted immunosuppressant, and subsequently concomitantly administering the gene expression modulating viral transfer vector and an antigen-presenting cell targeted immunosuppressant to the subject.

2. The method of claim 1, further comprising administering to the subject one or more repeat doses of the viral transfer vector subsequent to the concomitant administration of the viral transfer vector and the antigen-presenting cell targeted immunosuppressant to the subject.

3. A method comprising:

repeatedly, concomitantly administering to a subject an antigen-presenting cell targeted immunosuppressant and gene expression modulating transfer vector, and selecting one or more doses of the gene expression modulating viral transfer vector to be less than the dose of the gene expression modulating viral transfer vector that would be selected for the subject if the subject were expected to develop anti-gene expression modulating viral transfer vector immune responses due to the repeated administration of the gene expression modulating viral transfer vector.

4. The method of claim 1, wherein the concomitant administration is simultaneous administration.

5. The method of claim 1, wherein the subject is one to which the viral transfer vector has not been previously administered.

6. The method of claim 1, wherein the viral transfer vector is a retroviral transfer vector, an adenoviral transfer vector, a lentiviral transfer vector or an adeno-associated viral transfer vector.

7. The method of claim 1, wherein the gene expression modulating transgene encodes a DNA-binding protein or a therapeutic RNA.

8. The method of claim 1, wherein the antigen-presenting cell targeted immunosuppressant comprises an erythrocyte-binding therapeutic.

9. The method of claim 1, wherein the antigen-presenting cell targeted immunosuppressant comprises a negatively-charged particle.

10. The method of claim 1, wherein the antigen-presenting cell targeted immunosuppressant comprises an apoptotic-body mimic and one or more viral transfer vector antigens.

11. The method of claim 1, wherein the antigen-presenting cell targeted immunosuppressant comprises synthetic nanocarriers comprising an immunosuppressant.

12. The method of claim 1, wherein the immunosuppressant is an inhibitor of the NF-kB pathway.

13. The method of claim 1, wherein the immunosuppressant is rapamycin.

14. A method comprising:

repeatedly, concomitantly administering to a subject an antigen-presenting cell targeted immunosuppressant and gene expression modulating transfer vector, and selecting one or more doses of the gene expression modulating viral transfer vector to be at least equal to the dose of the gene expression modulating viral transfer vector that would be selected for the subject if the subject were expected to develop anti-gene expression modulating viral transfer vector immune responses due to the repeated administration of the gene expression modulating viral transfer vector.

* * * * *

SEQUENCE LISTING

```
<160> NUMBER OF SEQ ID NOS: 7

<210> SEQ ID NO 1
<211> LENGTH: 9
<212> TYPE: PRT
<213> ORGANISM: Artificial Sequence
<220> FEATURE:
```

```
<223> OTHER INFORMATION: Synthetic Polypeptide

<400> SEQUENCE: 1

Asn Ser Leu Ala Asn Pro Gly Ile Ala
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 2

His Tyr Leu Ser Thr Gln Ser Ala Leu
1               5

<210> SEQ ID NO 3
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 3
ggtgtattgc atgatatgt                                                  19

<210> SEQ ID NO 4
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 4
cgaaatttca ggtaagccga ggttatgaga tcttgggcct ctgc                      44

<210> SEQ ID NO 5
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 5
gaactttgca gagcctcaaa attaaatagg gcaggggaga taccatgatc                50

<210> SEQ ID NO 6
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 6
ctagctagcg gtaaggacca gcttctttg                                       29

<210> SEQ ID NO 7
<211> LENGTH: 27
<212> TYPE: DNA
```

-continued

```
<213> ORGANISM: Artificial Sequence
<220> FEATURE:
<223> OTHER INFORMATION: Synthetic Polynucleotide

<400> SEQUENCE: 7
ctagctagcg gttagcgtac agtctac                                    27
```